(12) United States Patent
Gibson et al.

(10) Patent No.: US 12,083,281 B2
(45) Date of Patent: *Sep. 10, 2024

(54) HEADGEAR FOR A RESPIRATORY MASK AND A METHOD FOR DONNING A RESPIRATORY MASK

(71) Applicant: ResMed Pty Ltd, Bella Vista (AU)

(72) Inventors: Joel Edward Gibson, Sydney (AU); Anthony Paul Barbara, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 0 days.

This patent is subject to a terminal disclaimer.

(21) Appl. No.: 17/868,190

(22) Filed: Jul. 19, 2022

(65) Prior Publication Data
US 2022/0347419 A1    Nov. 3, 2022

Related U.S. Application Data

(63) Continuation of application No. 16/660,999, filed on Oct. 23, 2019, now Pat. No. 11,395,895, which is a
(Continued)

(30) Foreign Application Priority Data

Nov. 5, 2007 (AU) ............................... 2007906083
Nov. 12, 2007 (AU) ............................... 2007906172

(51) Int. Cl.
*A61M 16/06* (2006.01)

(52) U.S. Cl.
CPC .... *A61M 16/0683* (2013.01); *A61M 16/0666* (2013.01); *Y10T 24/3427* (2015.01); *Y10T 24/3449* (2015.01); *Y10T 24/45262* (2015.01)

(58) Field of Classification Search
CPC .... A61M 16/06; A61M 16/0683–0694; A62B 18/00; A62B 18/02; A62B 18/025;
(Continued)

(56) References Cited

U.S. PATENT DOCUMENTS 1,837,775 A    12/1931  Howard
3,776,244 A *  12/1973  Morgan ............... A61F 13/122
                                                    132/273
(Continued)

FOREIGN PATENT DOCUMENTS

AU    199746837    7/1998
EP    1356841      10/2003
(Continued)

OTHER PUBLICATIONS

U.S. Office Action mailed Sep. 28, 2021 in corrsponding U.S. Appl. No. 17/191,791 (26 pages).
(Continued)

*Primary Examiner* — Valerie L Woodward
(74) *Attorney, Agent, or Firm* — Nixon & Vanderhye P.C.

(57) ABSTRACT

Headgear for a respiratory mask includes a strap arrangement including front strap portions adapted to be disposed over a patient's cheeks and having front ends adapted for attachment to an airway interfacing portion, top strap portions connected to respective front strap portions and adapted to be disposed over the top of a patient's head and to connect to each other, and a back strap extending rearwardly from and connecting respective junctions of the front strap portions and top strap portions or regions adjacent these junctions and adapted to locate underneath a patient's occiput. In use with a patient having long hair, the back strap is adapted to extend under the patient's hair and urge upwardly on the patient's hair and against the patient's head beneath the occiput. In use with a patient having short hair, the back strap is adapted to urge against the patient's head beneath the occiput. In an embodiment, front strap portions of the headgear may be provided with a sleeve or cover (e.g., constructed of a fleece material) to enhance comfort in use.

20 Claims, 68 Drawing Sheets

Related U.S. Application Data continuation of application No. 15/464,663, filed on Mar. 21, 2017, now Pat. No. 10,478,581, which is a continuation of application No. 14/318,869, filed on Jun. 30, 2014, now Pat. No. 9,629,974, which is a continuation of application No. 12/734,498, filed as application No. PCT/AU2008/001591 on Oct. 28, 2008, now Pat. No. 8,800,563.

(60) Provisional application No. 61/136,757, filed on Sep. 30, 2008, provisional application No. 61/129,682, filed on Jul. 11, 2008.

(58) Field of Classification Search
CPC ......... A62B 18/06; A62B 18/084; A42B 3/08; A42B 3/085; B63C 11/12; A41F 15/00–02
See application file for complete search history.

(56) References Cited

U.S. PATENT DOCUMENTS

| | | | |
|---|---|---|---|
| 4,414,973 A | 11/1983 | Matheson et al. | |
| 4,472,838 A | 9/1984 | Pompa | |
| 4,575,874 A | 3/1986 | Johnson | |
| 4,836,200 A | 6/1989 | Clark | |
| 4,884,301 A | 12/1989 | Aileo | |
| 5,388,743 A | 2/1995 | Silagy | |
| 5,445,858 A * | 8/1995 | Nwoko | F16F 9/006 428/318.6 |
| 5,546,605 A | 8/1996 | Mallardi | |
| 5,558,556 A | 9/1996 | Froehlich | |
| 5,687,425 A | 11/1997 | Blosser | |
| 5,687,743 A | 11/1997 | Goodwin | |
| 5,930,842 A | 8/1999 | Burruss | |
| 6,026,811 A | 2/2000 | Settle | |
| 6,070,579 A * | 6/2000 | Bryant | A41D 13/1161 128/207.11 |
| 6,119,694 A * | 9/2000 | Correa | A61M 16/0694 128/207.18 |
| 6,418,929 B1 | 7/2002 | Norfleet | |
| 6,615,834 B2 * | 9/2003 | Gradon | A61M 16/0666 128/207.11 |
| 6,802,109 B2 | 10/2004 | Hede et al. | |
| 6,820,615 B1 | 11/2004 | Feng | |
| 7,103,943 B2 | 9/2006 | Lambert | |
| 7,201,169 B2 | 4/2007 | Wilkie et al. | |
| 7,562,658 B2 | 7/2009 | Madaus et al. | |
| 7,624,735 B2 | 12/2009 | Ho et al. | |
| 7,877,817 B1 * | 2/2011 | Ho | A61M 16/0633 2/452 |
| 8,757,157 B2 | 6/2014 | Price et al. | |
| 8,800,563 B2 * | 8/2014 | Doherty | A61M 16/0683 128/206.28 |
| 9,629,974 B2 | 4/2017 | Gibson et al. | |
| 10,478,581 B2 | 11/2019 | Gibson et al. | |
| 11,369,767 B2 | 6/2022 | Gibson et al. | |
| 2003/0172936 A1 * | 9/2003 | Wilkie | A61M 16/0633 128/207.18 |
| 2004/0025882 A1 | 2/2004 | Madaus | |
| 2004/0067333 A1 | 4/2004 | Amarasinghe | |
| 2004/0134602 A1 | 7/2004 | Falla | |
| 2004/0221850 A1 | 11/2004 | Ging et al. | |
| 2004/0226566 A1 * | 11/2004 | Gunaratnam | A61M 16/0611 128/207.18 |
| 2005/0241644 A1 * | 11/2005 | Gunaratnam | A61M 16/0825 128/207.18 |
| 2006/0032504 A1 | 2/2006 | Burton et al. | |
| 2007/0186931 A1 | 8/2007 | Zollinger | |
| 2007/0226967 A1 | 10/2007 | Woods | |
| 2007/0250977 A1 | 11/2007 | Brown et al. | |
| 2008/0032599 A1 | 2/2008 | Kaye | |
| 2008/0190432 A1 * | 8/2008 | Blochlinger | A61M 16/0616 128/207.18 |
| 2009/0044808 A1 | 2/2009 | Guney et al. | |
| 2010/0258132 A1 * | 10/2010 | Moore | A61M 16/0683 128/207.11 |
| 2010/0258136 A1 | 10/2010 | Doherty et al. | |
| 2014/0311494 A1 | 10/2014 | Gibson et al. | |
| 2017/0189636 A1 | 7/2017 | Gibson et al. | |
| 2020/0289776 A1 | 9/2020 | Gibson et al. | |

FOREIGN PATENT DOCUMENTS

| | | | | |
|---|---|---|---|---|
| WO | WO-2005063328 A1 * | 7/2005 | ........ | A61M 16/0057 |
| WO | WO 2007/041786 A1 | 4/2007 | | |

OTHER PUBLICATIONS

U.S. Office Action mailed May 27, 2021 in corresponding U.S. Appl. No. 17/191,761 (26 pages).
International Search Report issued in Appln. No. PCT/AU2008/001591 dated Feb. 16, 2009.
International Preliminary Report on Patentability issued in Appln. No. PCT/AU2008/001591 dated May 11, 2010.
U.S. Appl. No. 14/288,831, filed May 28, 2014.

* cited by examiner

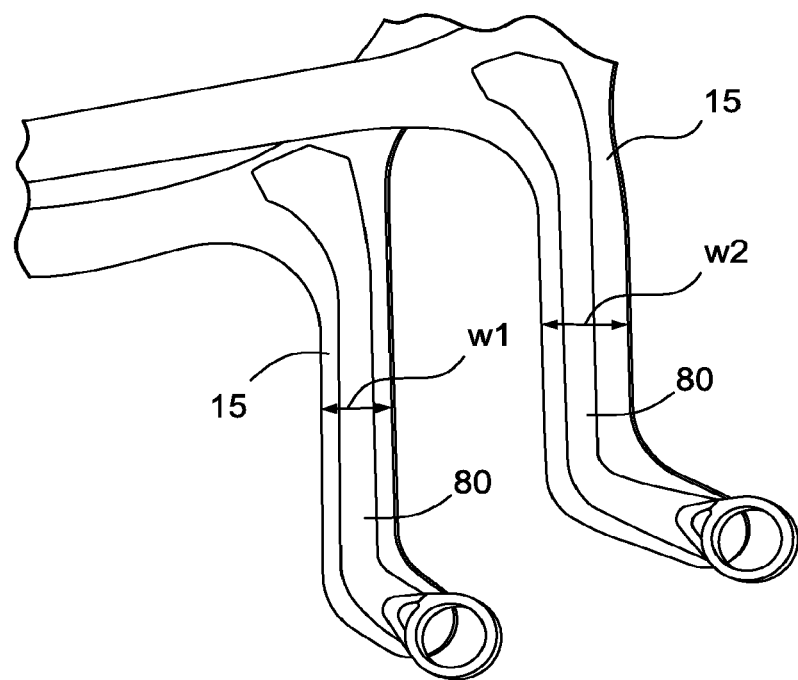
Fig. 17
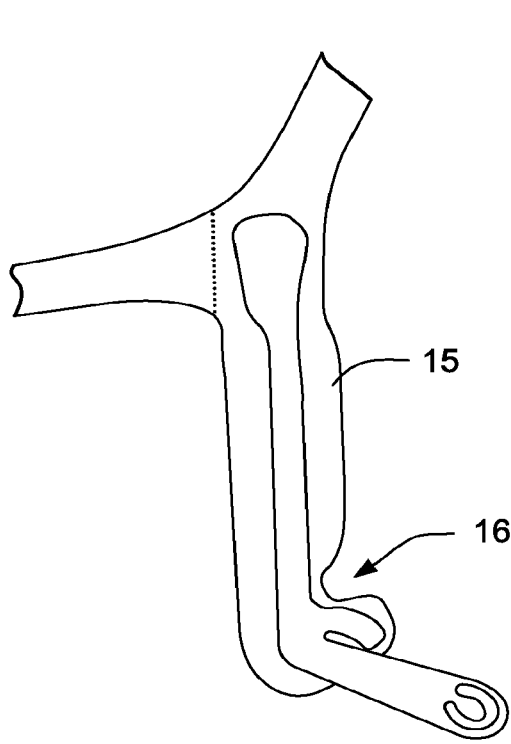 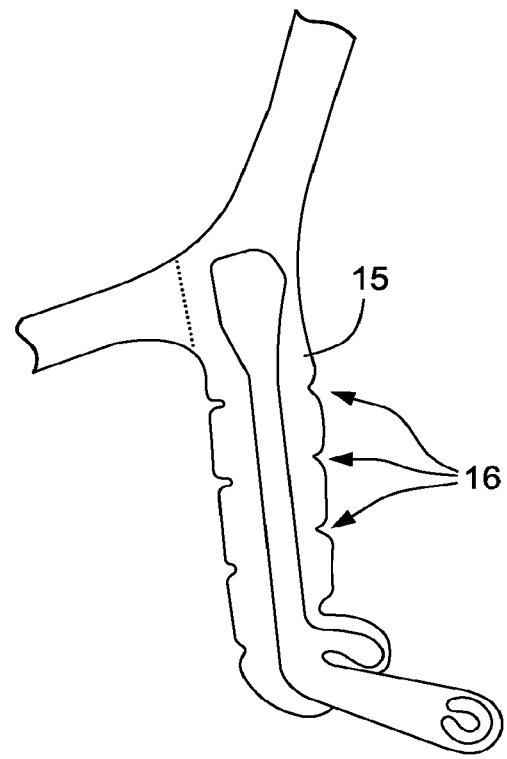
Fig. 18   Fig. 19

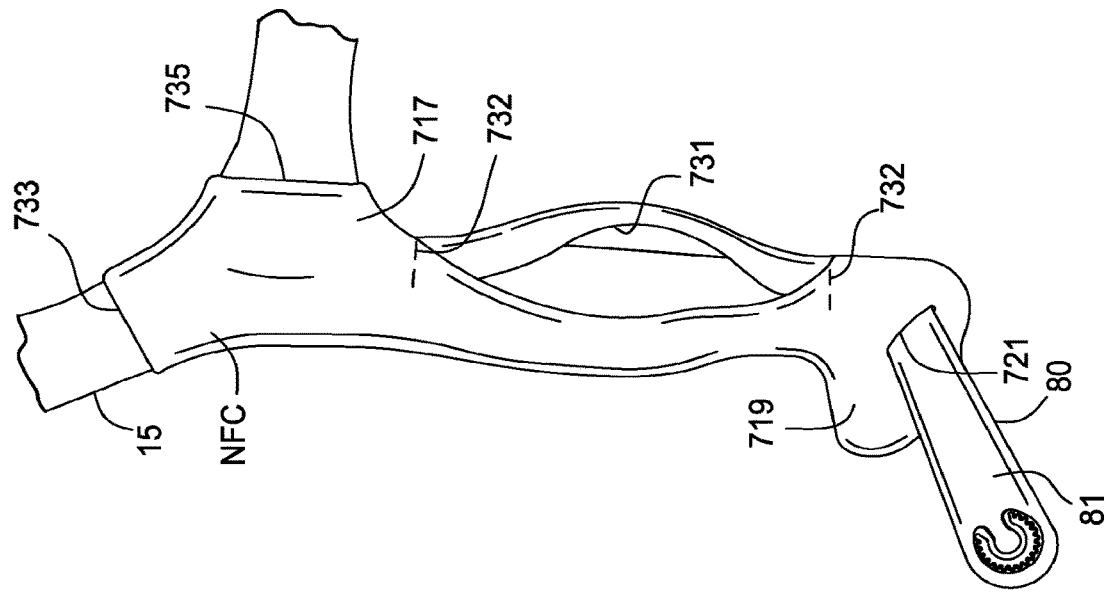
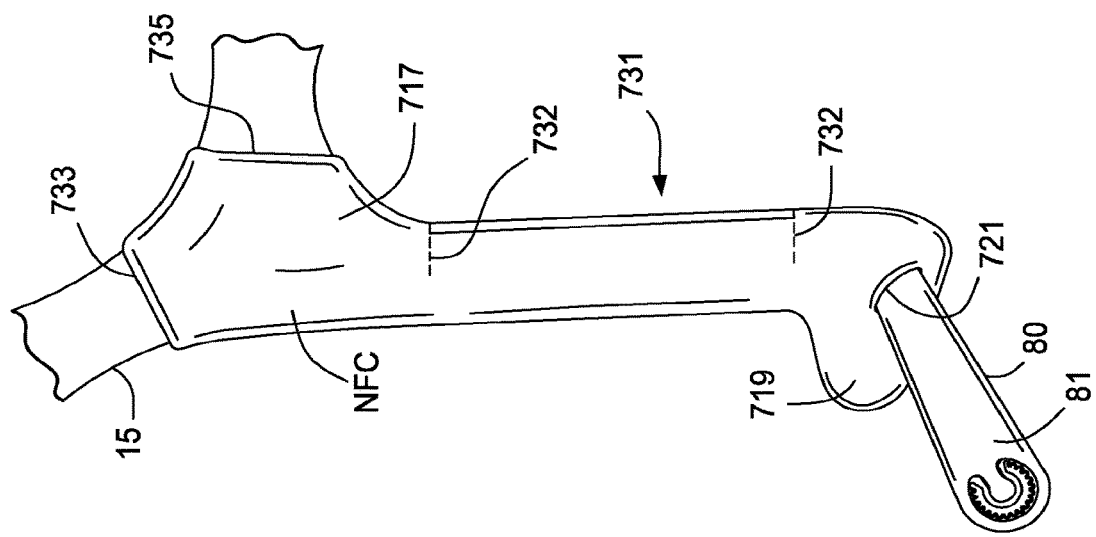
Fig. 27
Fig. 26

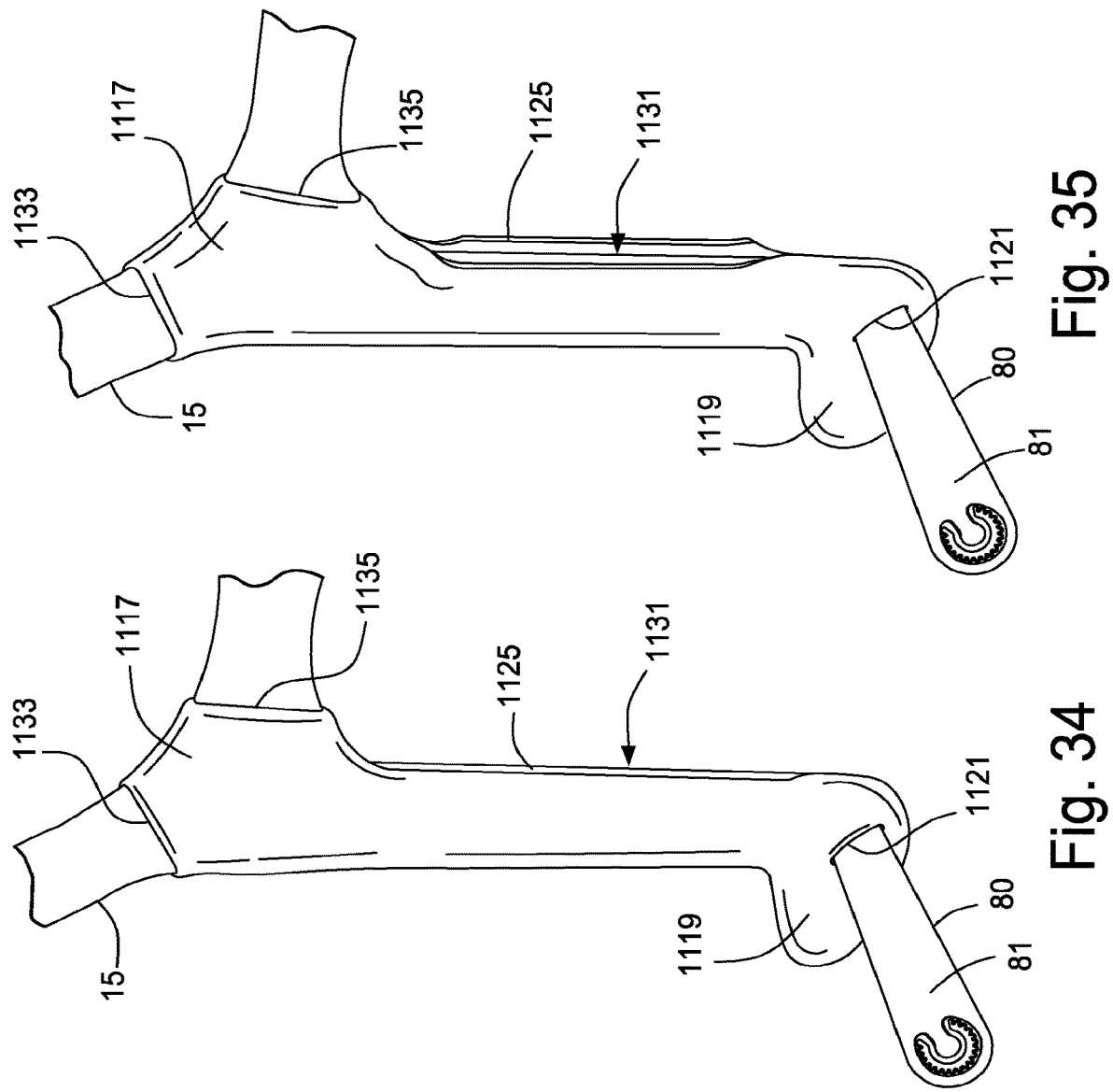

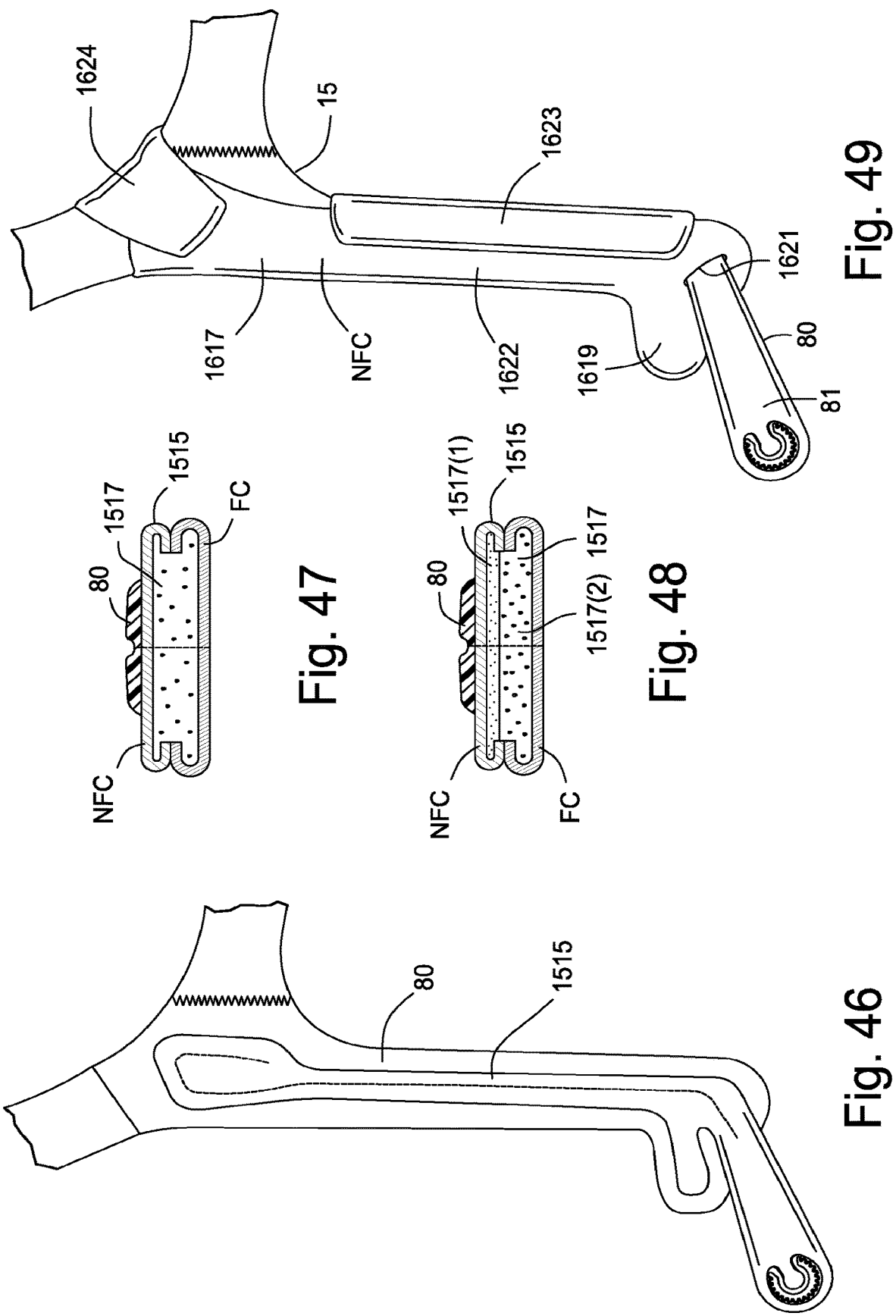

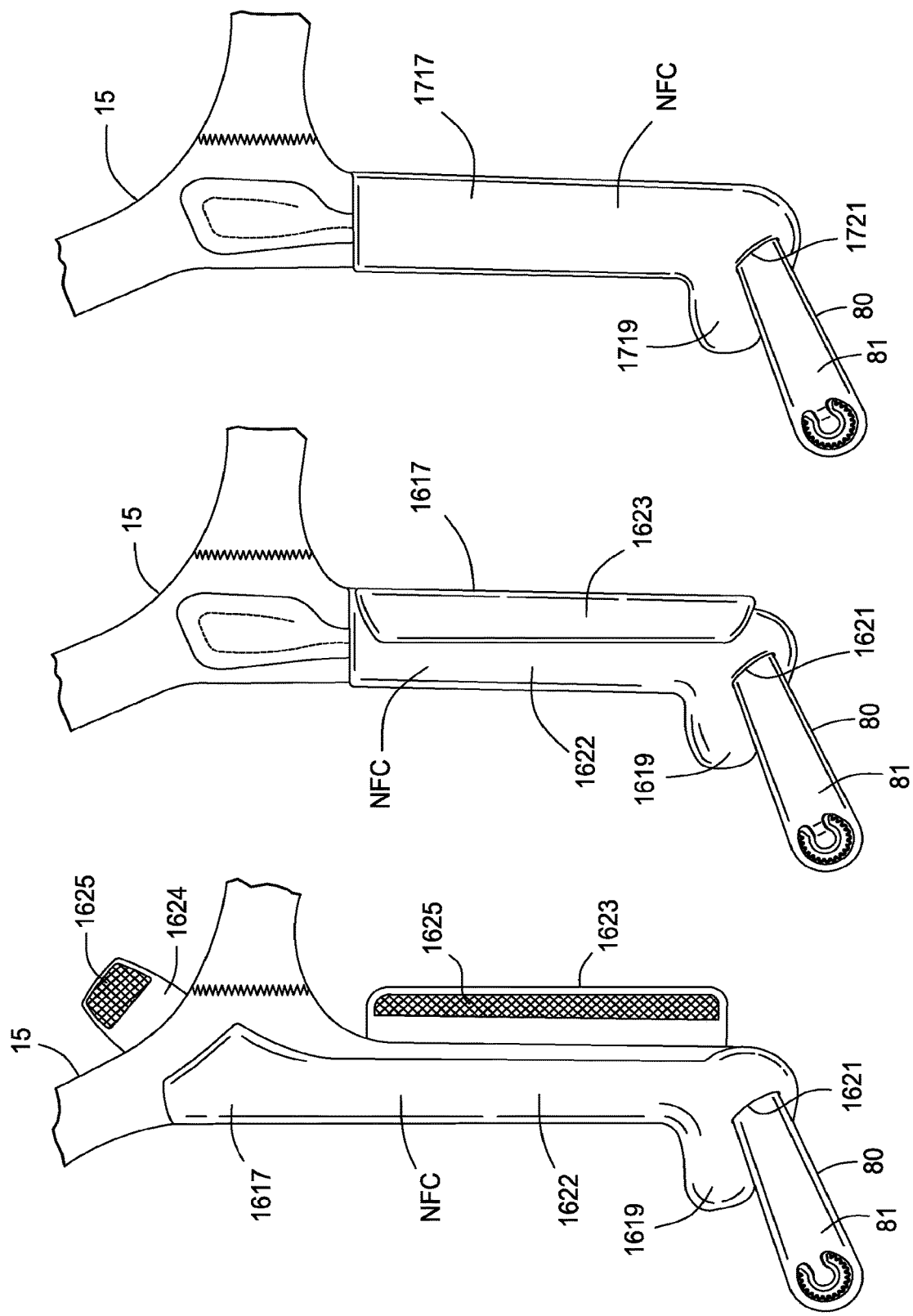

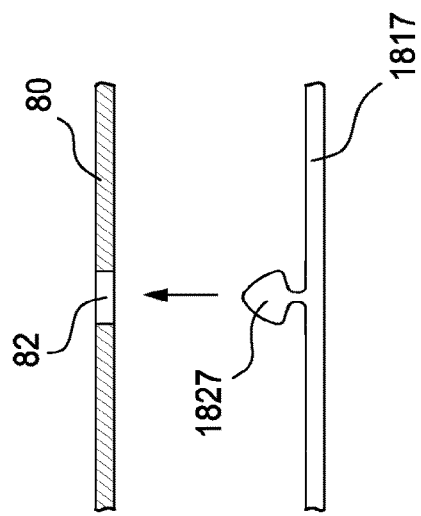
Fig. 55
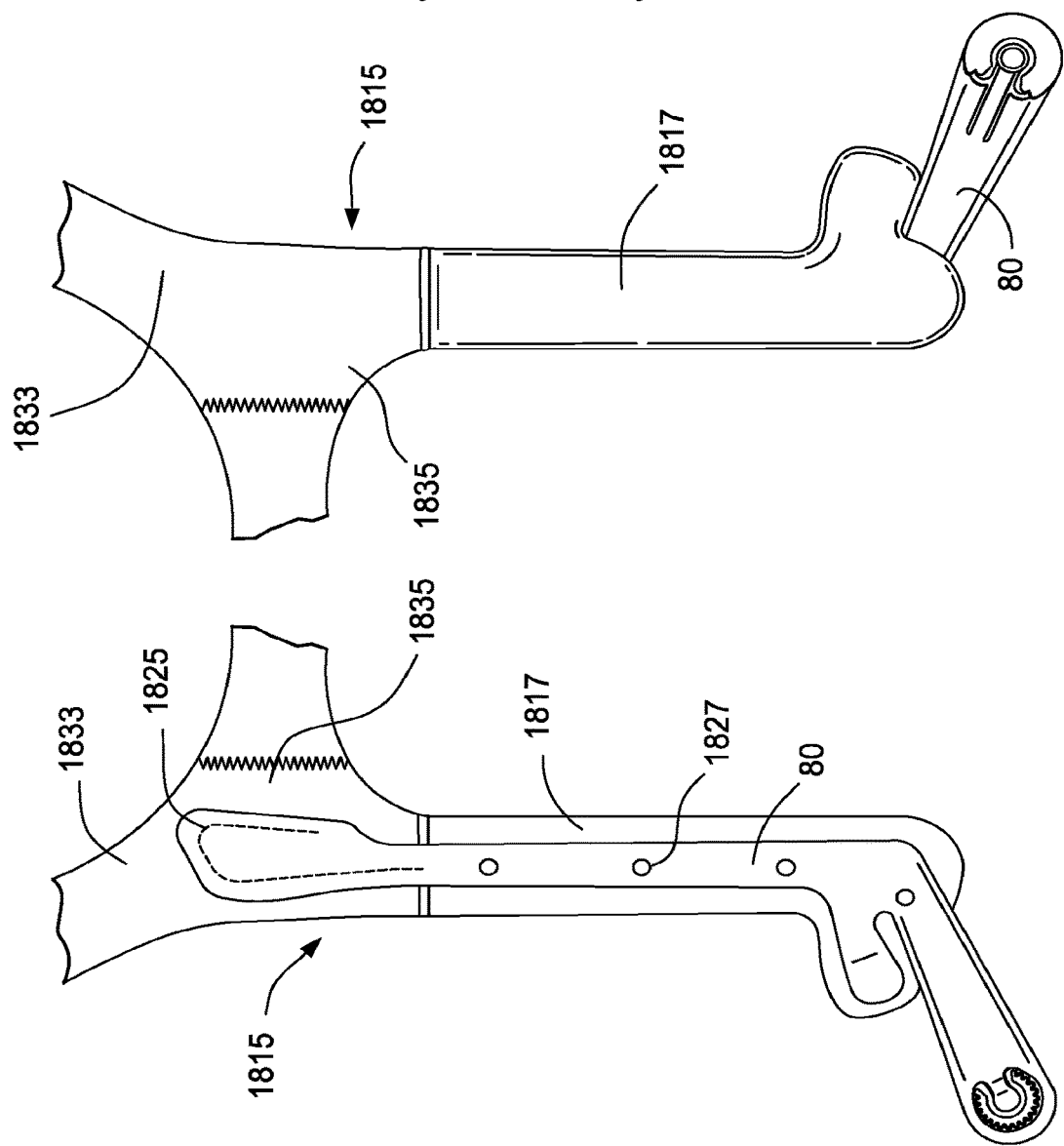
Fig. 54
Fig. 53

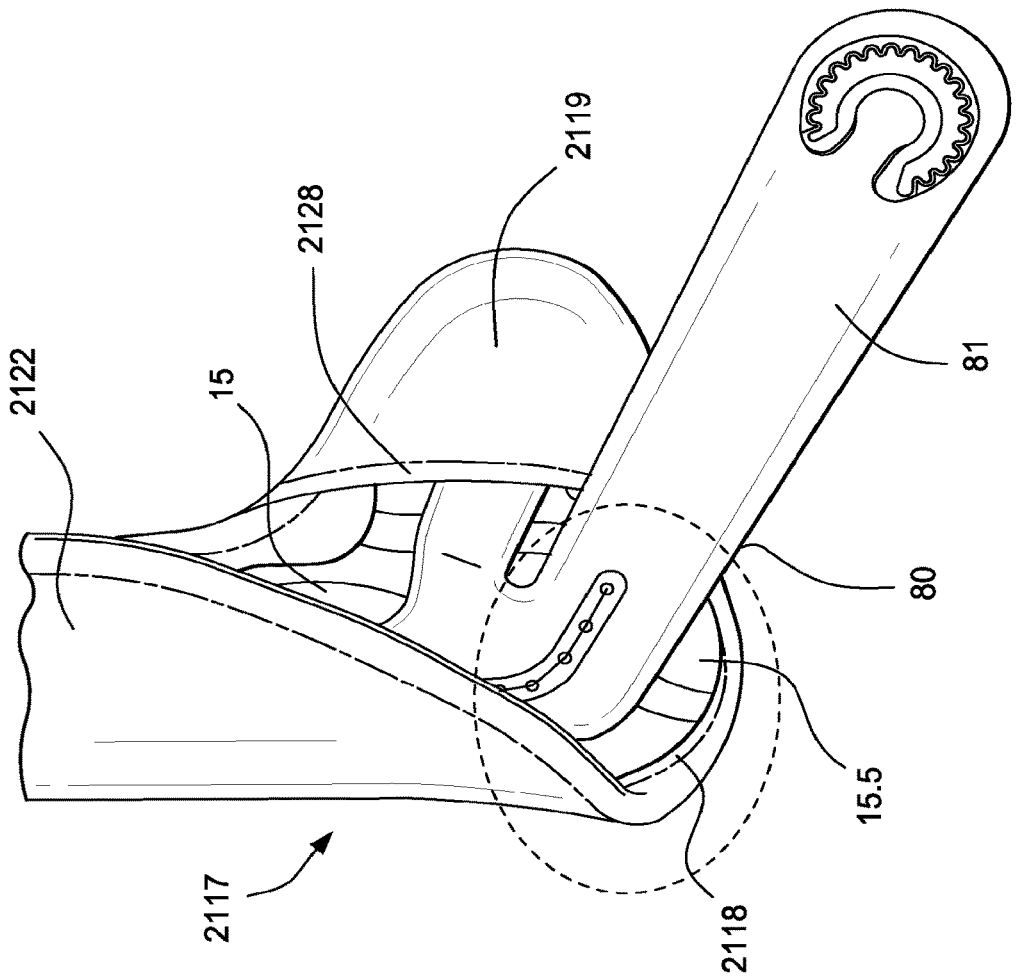
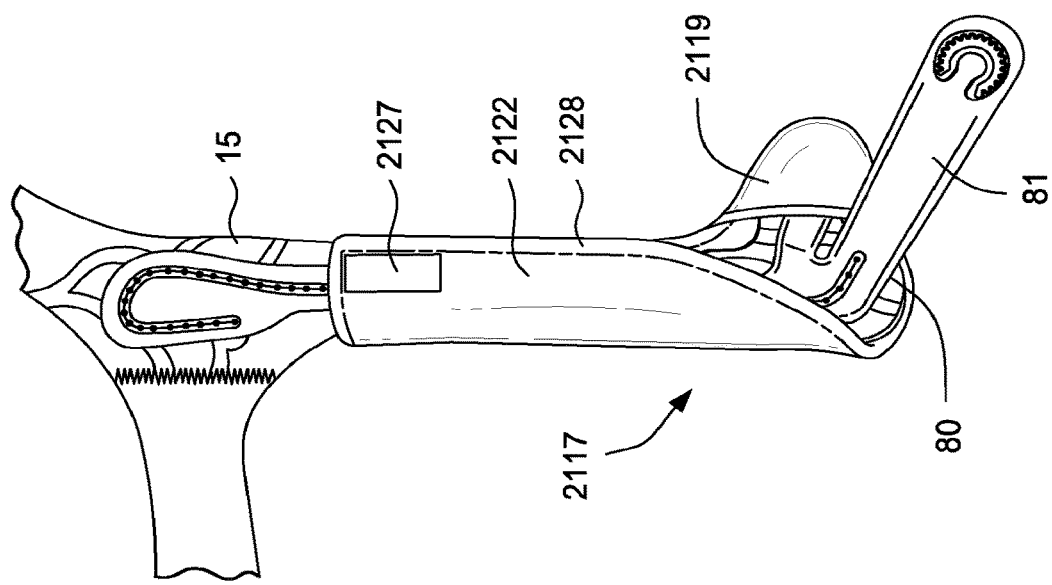

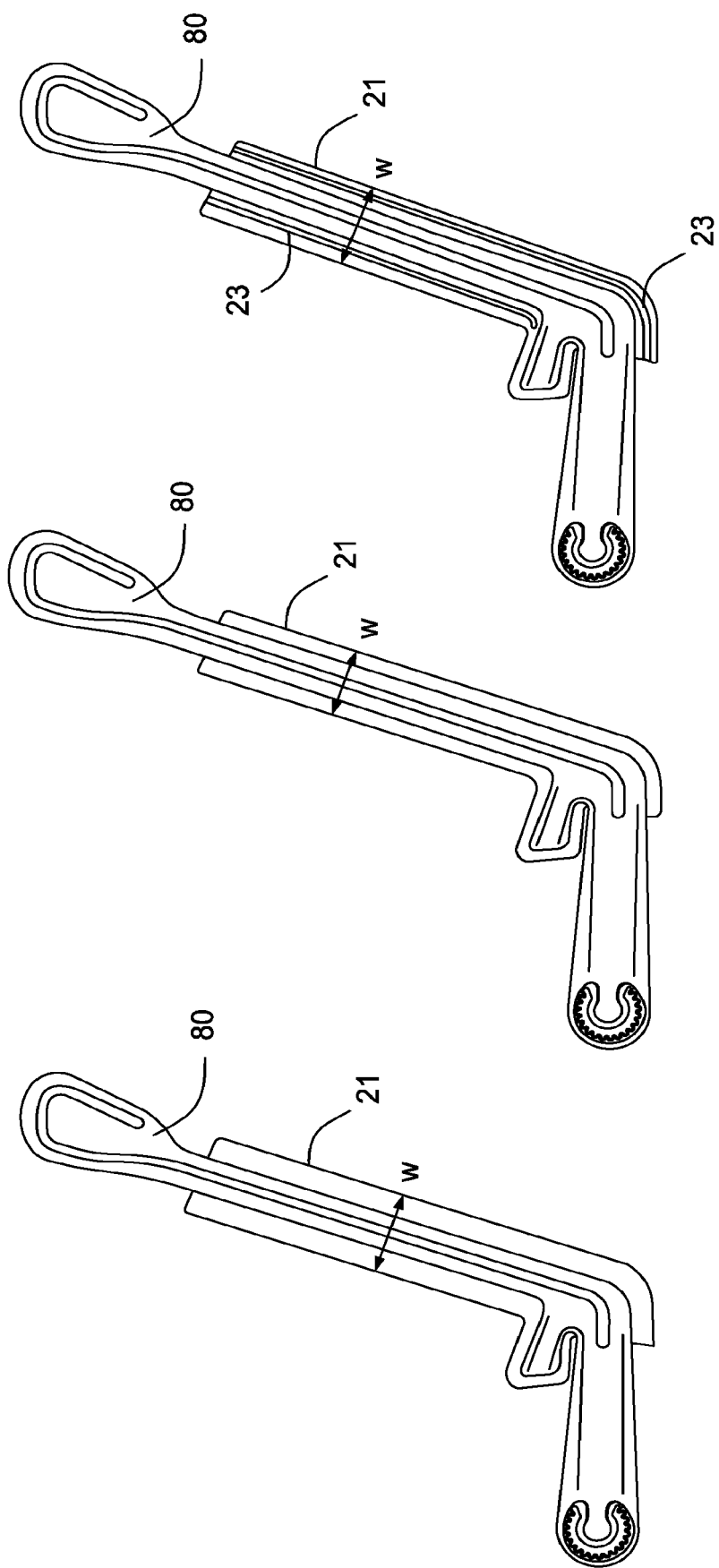

HEADGEAR FOR A RESPIRATORY MASK AND A METHOD FOR DONNING A RESPIRATORY MASK

CROSS-REFERENCE TO APPLICATIONS

This application is a continuation of U.S. patent application Ser. No. 16/660,999, filed Oct. 23, 2019, which is a continuation of U.S. patent application Ser. No. 15/464,663, filed Mar. 21, 2017, now U.S. Pat. No. 10,478,581, which is a continuation of U.S. patent application Ser. No. 14/318,869, filed Jun. 30, 2014, now U.S. Pat. No. 9,629,974, which is a continuation of U.S. patent application Ser. No. 12/734,498, filed May 5, 2010, now U.S. Pat. No. 8,800,563, which is the U.S. National Phase of International Application No. PCT/AU2008/001591, filed Oct. 28, 2008, which designated the U.S. and claims the benefit of U.S. Provisional Application Nos. 61/129,682, filed Jul. 11, 2008, and 61/136,757, filed Sep. 30, 2008, and Australian Provisional Application Nos. AU 2007906083, filed Nov. 5, 2007, and AU 2007906172, filed Nov. 12, 2007, each of which is incorporated herein by reference in its entirety.

FIELD OF THE INVENTION

The present invention relates to headgear for a respiratory mask, e.g., used in treating sleep disordered breathing (e.g., sleep apnea).

BACKGROUND OF THE INVENTION

Many different types of respiratory masks exist providing a variety of different headgear arrangements. Headgear arrangements are used to stabilise an airway interfacing portion and sometimes an air delivery conduit with respect to a patient's face.

One problem encountered by some patients who have long hair is the tendency of the headgear, which sits over the top of the long hair, to slide around over the patient's hair or to displace an outer layer or layers of the patients hair over inner layers. This can compress, move and/or destabilise the airway interfacing portion and mess up and/or tangle the patient's hair. Additionally, current headgear is designed to slide over the head and hair of the patient in order to position it, which can also cause hair to be displaced.

SUMMARY OF THE INVENTION

One aspect of the invention relates to a mask that is especially adapted to be worn by a person having long hair and to stabilise properly on their head.

Another aspect of the invention relates to the provision of a back strap that is adapted to locate underneath a patient's long hair. In one embodiment, the back strap may press against a lower region of a patient's occiput or their upper neck in use. In one embodiment, the back strap may urge upwardly against the patient's long hair from underneath in use.

Advantageously, the headgear is able to be properly stabilised on a patient having long hair and so is able to hold the airway interfacing portion more stably on the patient's face in use.

According to another aspect of the present invention, headgear for a respiratory mask includes a strap arrangement comprising front strap portions adapted to be disposed over a patient's cheeks and having front ends adapted for attachment to an airway interfacing portion, top strap portions connected to respective front strap portions and adapted to be disposed over the top of a patient's head and to connect to each other, and a back strap extending rearwardly from and connecting respective junctions of the front strap portions and top strap portions or regions adjacent these junctions and adapted to locate underneath a patient's occiput. In use with a patient having long hair, the back strap is adapted to extend under the patient's hair and urge upwardly on the patient's hair and against the patient's head beneath the occiput. In use with a patient having short hair, the back strap is adapted to urge against the patient's head beneath the occiput.

According to another aspect of the present invention, headgear for a respiratory mask includes a strap arrangement comprising front strap portions adapted to be disposed over a patient's cheeks and having front ends adapted for attachment to an airway interfacing portion, top strap portions connected to respective front strap portions and adapted to be disposed over the top of a patient's head and to connect to each other, and a back strap extending rearwardly from and connecting respective junctions of the front strap portions and top strap portions or regions adjacent these junctions and adapted to locate underneath a patient's occiput. The top strap portions are connected at or near the crown of the patient's head.

According to another aspect of the present invention, headgear for a respiratory mask includes a strap arrangement comprising front strap portions adapted to be disposed over a patient's cheeks and having front ends adapted for attachment to an airway interfacing portion, top strap portions connected to respective front strap portions and adapted to be disposed over the top of a patient's head and to connect to each other, and a back strap extending rearwardly from and connecting respective junctions of the front strap portions and top strap portions or regions adjacent these junctions and adapted to locate underneath a patient's occiput. The top strap comprises a headband.

According to another aspect of the present invention, a method for donning a respiratory mask includes inserting a patient's head between a headband and back strap of the respiratory mask, sliding the headband across the front of the patient's face and up their forehead to a position between the forehead and a crown of the patient's head, and locating an airway interfacing portion of the respiratory mask in an interfacing location for delivery of a gas.

According to another aspect of the present invention, a method for donning a respiratory mask includes inserting a patient's head between front headgear straps and a back strap of the mask, if the patient has long hair, pulling the patients hair out and over the top of the back strap, pulling the rear ends of the front headgear straps up and over the ears, and connecting top straps of the respiratory mask adjacent the crown of the patient's head.

According to another aspect of the present invention, a clasp for connecting a pair of headgear straps includes a male clasp portion including a first portion adapted to engage one of the straps and a second portion that provides a hook portion, and a female clasp portion including a first portion adapted to engage the other of the straps and a second portion that provides an aperture portion. The hook portion is releasably engagable within the aperture portion to connect the male and female clasp portions to one another.

Advantageously, the mask is pulled into place by an upward movement that serves to slide the patient's hair off their face, keeping the patient's hair neater and managing their hair around their ears. This serves to increase patient comfort. A further advantage of this method is that once the front headgear straps are positioned over the ears, the mask is held in place while the patient connects the top straps. Thus, the top straps can be held and connected without the patient having to support the weight of the rest of the mask at the same time.

In an embodiment of the present invention, headgear for a mask system may have a back strap, where the back strap may be made from elastic with a spring constant of between 0.001 N/mm and 1 N/mm, e.g., between 0.007 N/mm and 0.07 N/mm (e.g., about 0.02 N/mm). The back strap may provide the only adjustment for the mask system or headgear. Alternatively, the back strap may not provide the only adjustment for the mask system or headgear, e.g., the top strap of the headgear may allow for adjustment.

In another embodiment, headgear for a mask system may include a back strap that extends relative to the top and front straps within a certain angular range, e.g., at about 70 to 110 degrees to the angle of the front straps and at about 160 to 180 degrees to the angle of the top straps.

In another embodiment, headgear for a mask system may include a back strap that extends relative to the horizontal datum plane of the patient's head within a certain angular range, e.g., at about 30 to 60 degrees.

In another embodiment, headgear for a mask system may include a top and/or front strap material that extends over top of ears to direct angle of back strap. In another form, the top and/or front strap material may touch the ears with low force.

In another embodiment, headgear for a mask system may include a back strap that joins front/top strap at an angle other than perpendicular to the direction of the back strap to provide more even force distribution on head. The back strap may be arranged so that when the mask is held off one's head it adopts an in-use shape allowing it to be more easily donned.

In another embodiment, the back strap may urge upwardly against hair at the back of the head as well as against the back of the head/neck when located on a person with long hair.

In another embodiment, the back strap may locate under the occiput when located on a person with short hair.

Another aspect of the invention relates to the provision of a clasp and/or clip to bring top straps together located at crown of head so patient can sleep on either side. This may also include a single clasp so connection is independent of adjustment. Additionally, adjustment may be on one side or on both sides of the clasp connection. Adjustment may be performed by Velcro®, hook and loop, or any other reasonable method of adjustment. In one form, the clasp may have a lateral fixed angle. The clasp may be a hook and loop.

In another embodiment, thin rigidisers having a width of between 2 mm and 25 mm, e.g., between 2 mm and 9 mm, may be provided to the strap of the headgear.

In another embodiment, headgear may include thin top straps having a width of between 5 mm and 100 mm to minimise visual impact and impact on hair styling. In an embodiment, the top straps may have a width of between 10 mm and 20 mm, e.g., about 14 mm.

In another embodiment, headgear may include thin front straps having a width of between 2 mm and 30 mm to minimise visual impact and impact on hair styling. In an embodiment, the width of the front straps may be about 19 mm wide. In another embodiment, the width of the front straps may be about 20 mm. In another embodiment, the width of the front straps may be about 25 mm. In an embodiment, the thin front straps may not be wider than the rigidisers.

In another embodiment, the headgear may be adapted to camouflage by color selection, e.g., matching hair or skin color. It is possible to have headgear suited to women, e.g., made from colors traditionally associated with women (e.g., pink, purple).

In another embodiment, the headgear may be adapted to camouflage by pattern selection, e.g., matching facial shape of women.

In another embodiment, the headgear material pattern may be such that fabric can be die-cut with the headgear shape in any orientation while still ensuring the patterned headgear is aesthetically suitable, e.g., the left hand side and right hand side parts of the headgear can be nested, i.e., cut out of an adjacent portion of material and still be aesthetically suitable.

In another embodiment, the top strap of the headgear may take the form of a hair band or head band, e.g., a sock or sliding band over the top strap such that the top strap is substantially covered. The top strap may be the hand band or the head band may be integrally formed with the top strap. The head band may be made from elastic.

In another embodiment, fabric loops may tie down loose ends of headgear straps.

Another embodiment of the invention relates to a method for donning a head band with mask system attached, where the head of the patient goes between the head band and the back strap, and the head band then slides over the front of the face of the user to an in use position.

Another embodiment of the invention relates to a method for donning a head band mask without a mask system attached, where the head of the patient goes between the head band and back strap, and the head band then slides over the front of the face of the user to an in use position. The mask system is then connected to the headgear.

Another embodiment of the invention relates to a method for donning headgear for person with long hair, where the patient puts their head through the loop between the front headgear straps and the back headgear straps, hair is pulled out and over the top of the back strap, the top headgear straps are pulled up the patient's face until and in use position.

Another embodiment of the invention relates to headgear for a respiratory mask including a strap arrangement and a cover. The strap arrangement includes front strap portions adapted to be disposed over a patient's cheeks and having front ends adapted for attachment to an airway interfacing portion, top strap portions connected to respective front strap portions and adapted to be disposed over the top of a patient's head and to connect to each other, and a back strap extending rearwardly from and connecting respective junctions of the front strap portions and top strap portions or regions adjacent these junctions and adapted to locate underneath a patient's occiput. Each front strap portion includes a front strap and a rigidizer provided to the front strap. The cover extends along at least a portion of each front strap portion. The cover includes a pocket to receive a cheek support of each front strap portion and a slot to allow an end of the rigidizer to extend therethrough.

Another embodiment of the invention relates to headgear for a respiratory mask including a strap arrangement comprising front strap portions adapted to be disposed over a patient's cheeks and each front strap portion having a cheek support adapted to rest on the patient's cheek in use, and a cover provided to each front strap portion and structured to at least partially encapsulate the cheek support.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of the invention. In such drawings:

FIG. 17 are side views of front headgear straps with different widths according to an embodiment of the present invention;

FIG. 18 is a side view of a front headgear strap with a single deep notch according to an embodiment of the present invention;

FIG. 19 is a side view of a front headgear strap with multiple notches according to an embodiment of the present invention;

FIG. 26 is a side view of a front headgear strap and sleeve according to another embodiment of the present invention;

FIG. 27 is a side view of the front headgear strap and sleeve of FIG. 26 with the sleeve partially opened;

FIG. 34 is a side view of a front headgear strap and sleeve according to another embodiment of the present invention;

FIG. 35 is a side view of the front headgear strap and sleeve of FIG. 34 with the sleeve opening unlocked;

FIG. 36 is a schematic view of the snap lock fastener of the sleeve of FIG. 34;

FIG. 46 is a side view of a front headgear strap with a foam core according to another embodiment of the present invention;

FIG. 47 is a cross-sectional view showing an exemplary arrangement for the foam core of FIG. 46;

FIG. 48 is a cross-sectional view showing another exemplary arrangement for the foam core of FIG. 46;

FIG. 49 is a side view of a front headgear strap and sleeve according to another embodiment of the present invention;

FIG. 50 is a side view of the front headgear strap and sleeve of FIG. 49 with the sides of the sleeve detached;

FIG. 51 is a side view showing an alternative arrangement for the front headgear strap and sleeve of FIG. 49;

FIG. 52 is a side view of a front headgear strap and sock according to another embodiment of the present invention;

FIG. 53 is a side view of a front headgear strap with a silicone strap portion according to another embodiment of the present invention;

FIG. 54 is an opposing side view of the front headgear strap with silicone strap portion of FIG. 53;

FIG. 55 is a schematic view of the snap fit tab arrangement of the silicone strap portion of FIG. 53;

FIG. 67 is a side view of a sock attached to a front headgear strap according to an embodiment of the present invention;

FIG. 68 is an enlarged view of the sock of FIG. 67;

FIGS. 78-80 are perspective views of headgear including silicone cheek pad provided to a rigidiser according to embodiments of the present invention;

FIGS. 91-1 to 91-5 are various views of a clasp for headgear according to another embodiment of the present invention;

FIGS. 92-1 to 92-5 are various views of a clasp for headgear according to another embodiment of the present invention;

FIGS. 93-1 to 93-2 are perspective views of a female clasp portion common to the clasps shown in FIGS. 91-1 to 91-5 and 92-1 to 92-5;

FIG. 98b is a perspective view of a female clasp portion of the clasp of FIG. 98a;

FIG. 104b is a side view of the clasp of FIG. 104a;

FIG. 115b is a side view of the clasp of FIG. 115a;

FIG. 117 is a perspective view of a clasp for headgear according to another embodiment of the present invention;

FIG. 118a is a perspective view of a clasp for headgear according to another embodiment of the present invention;

FIG. 118b is a side view of a male clasp portion of the clasp of FIG. 118a;

FIG. 119a is a perspective view of a clasp for headgear according to another embodiment of the present invention;

FIG. 119b is a perspective view showing an alternative male clasp portion for the clasp of FIG. 119a;

FIG. 120a is a perspective view of a clasp for headgear according to another embodiment of the present invention;

FIG. 120b is a side view of the clasp of FIG. 120a;

FIG. 121 is a perspective view of a clasp for headgear according to another embodiment of the present invention;

FIG. 122 is a perspective view of a clasp for headgear according to another embodiment of the present invention;

FIG. 123 is a perspective view of a clasp for headgear according to another embodiment of the present invention;

FIG. 124 is a perspective view of a clasp for headgear according to another embodiment of the present invention;

FIG. 125 is a perspective view of a clasp for headgear according to another embodiment of the present invention;

Figure 126:
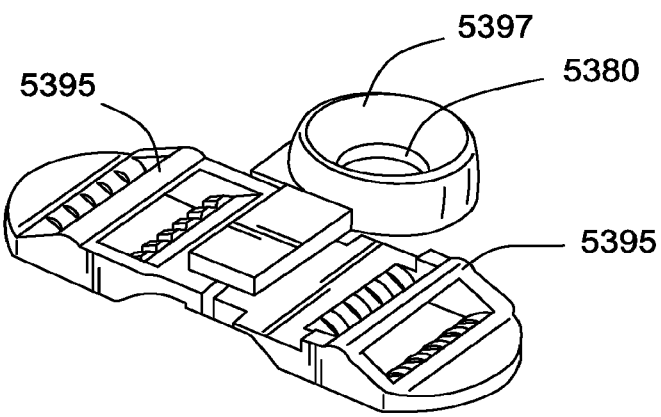
Figure 127:
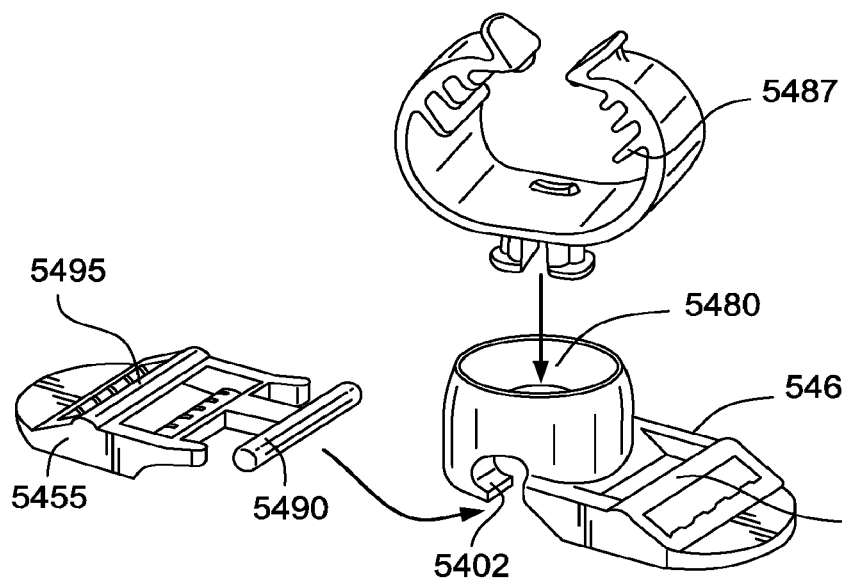
Figure 128:
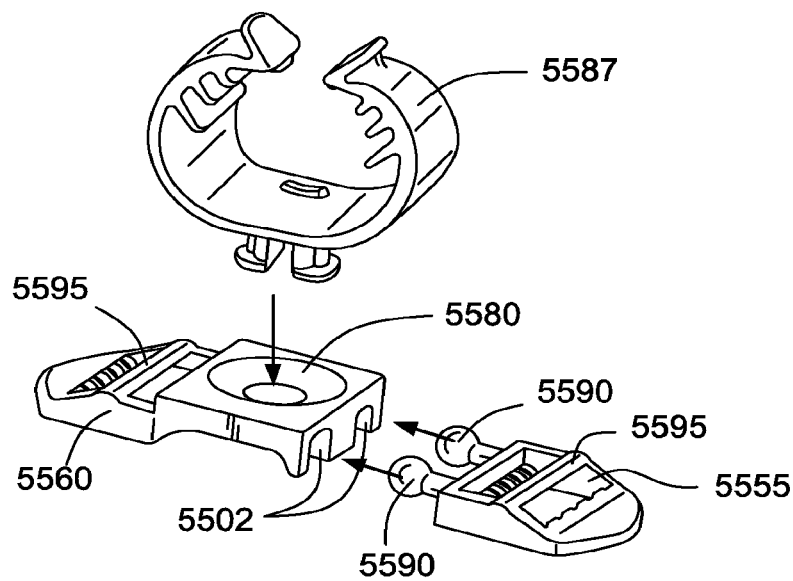
Figure 129:
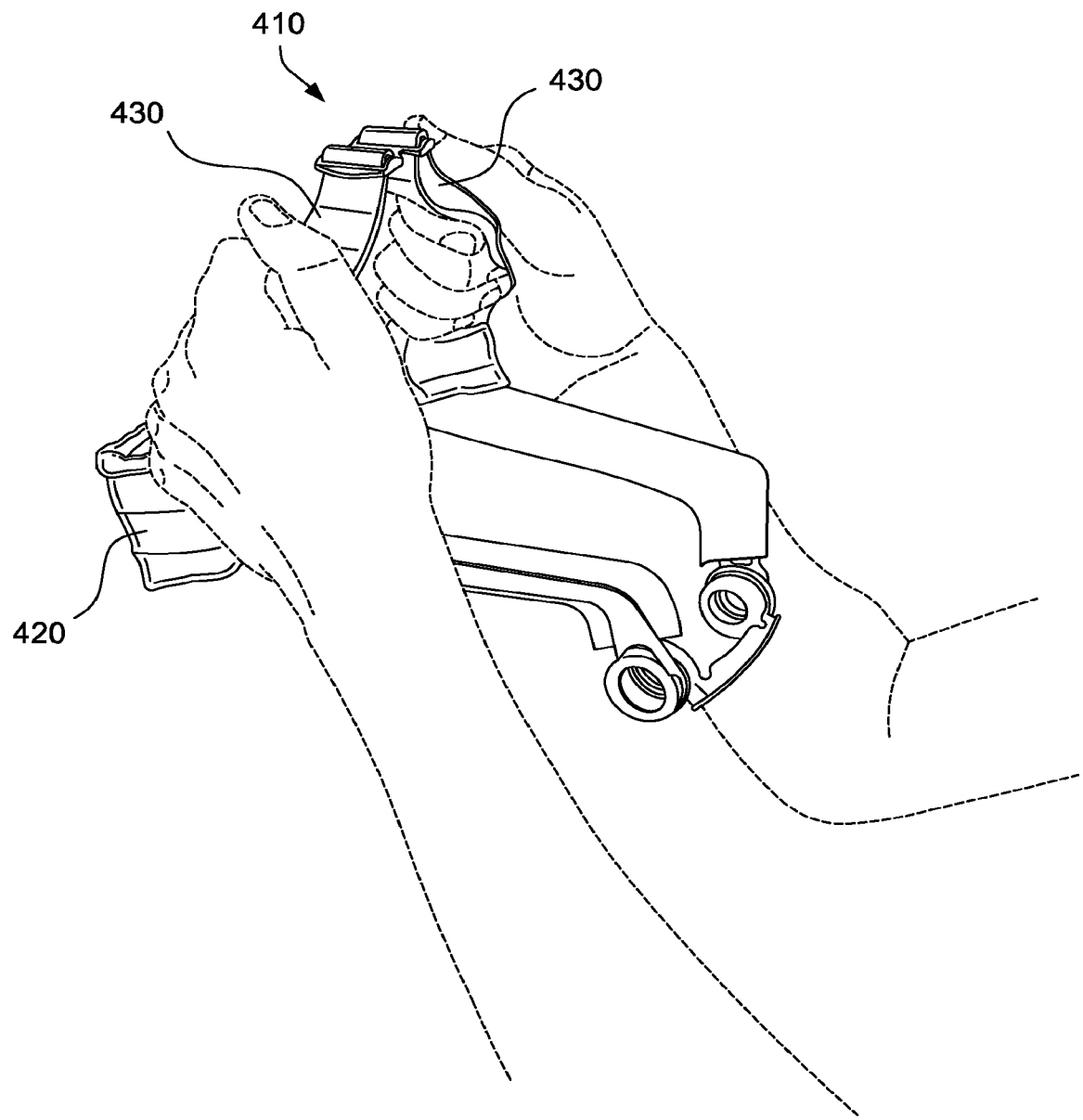
Figure 130:
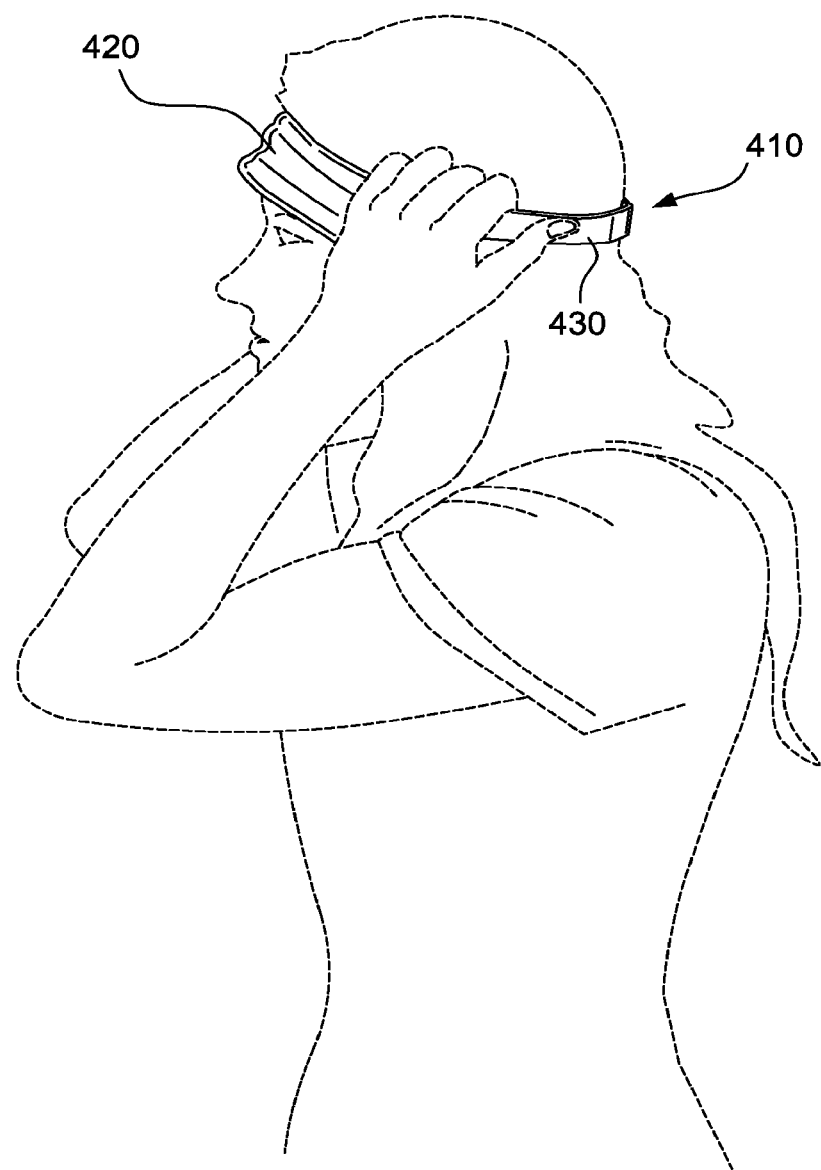
Figure 131:
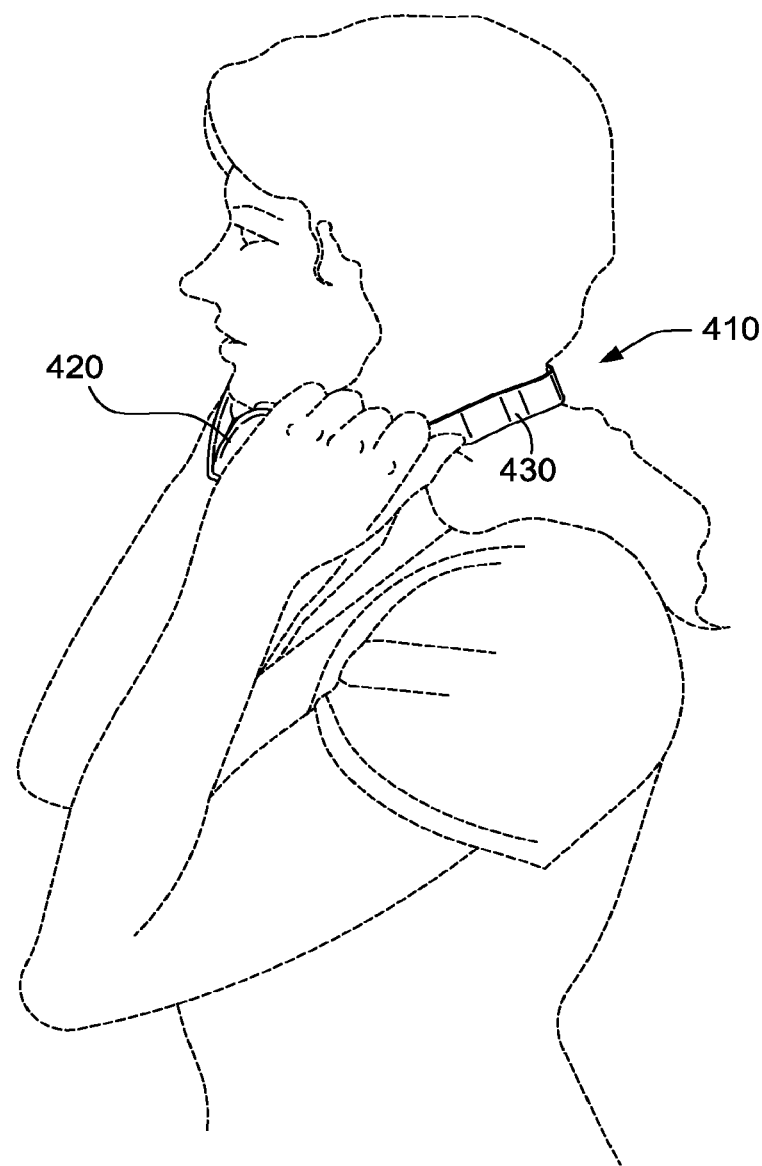
Figure 132:
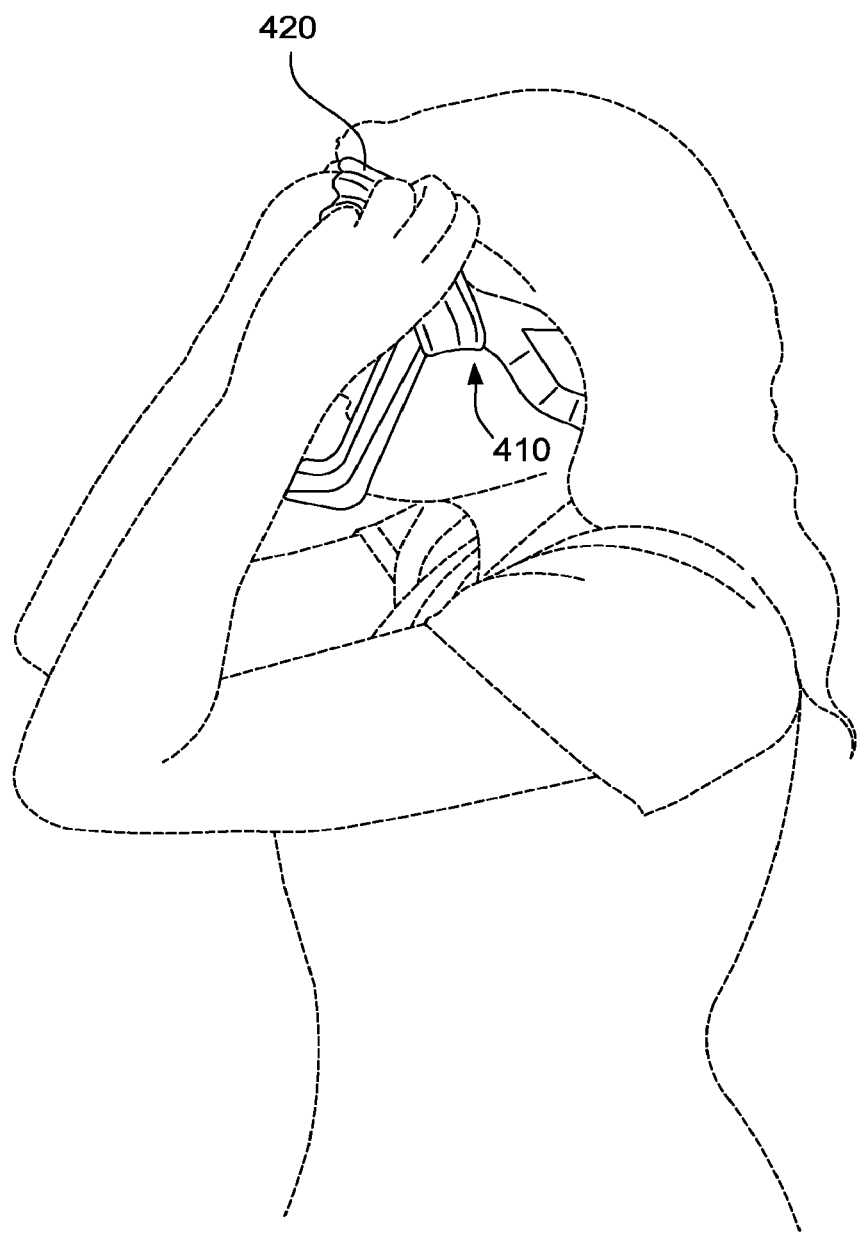
Figure 133:
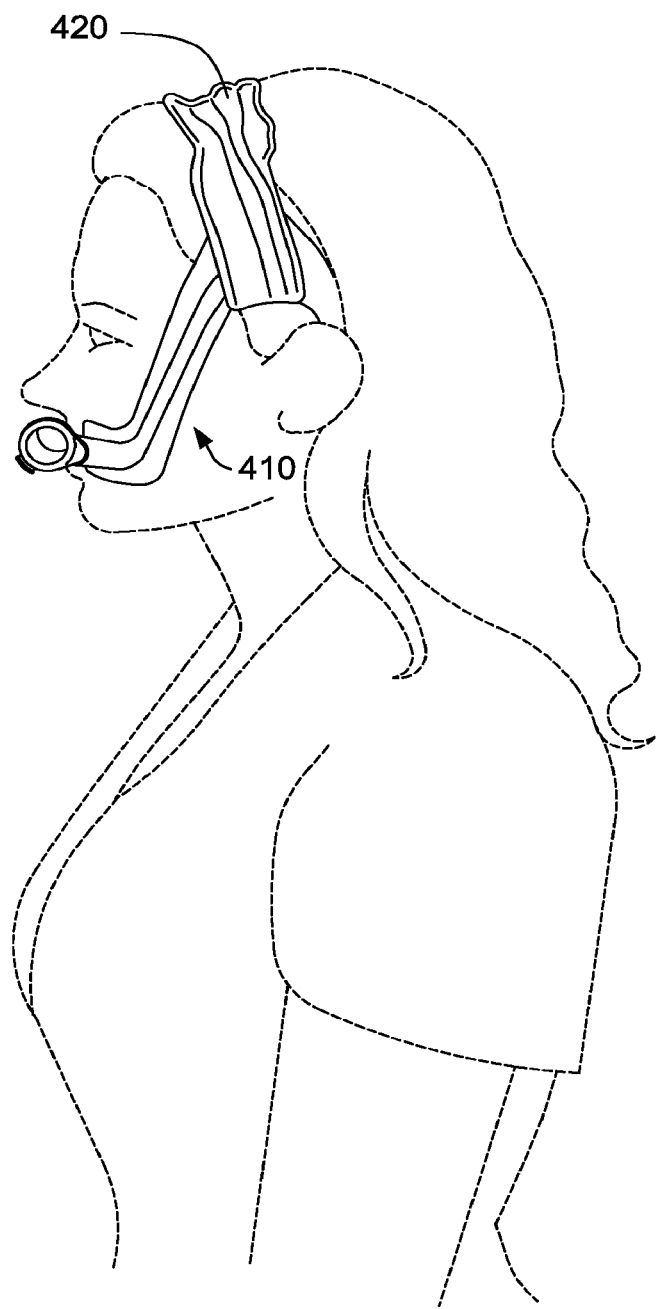
Figure 134:
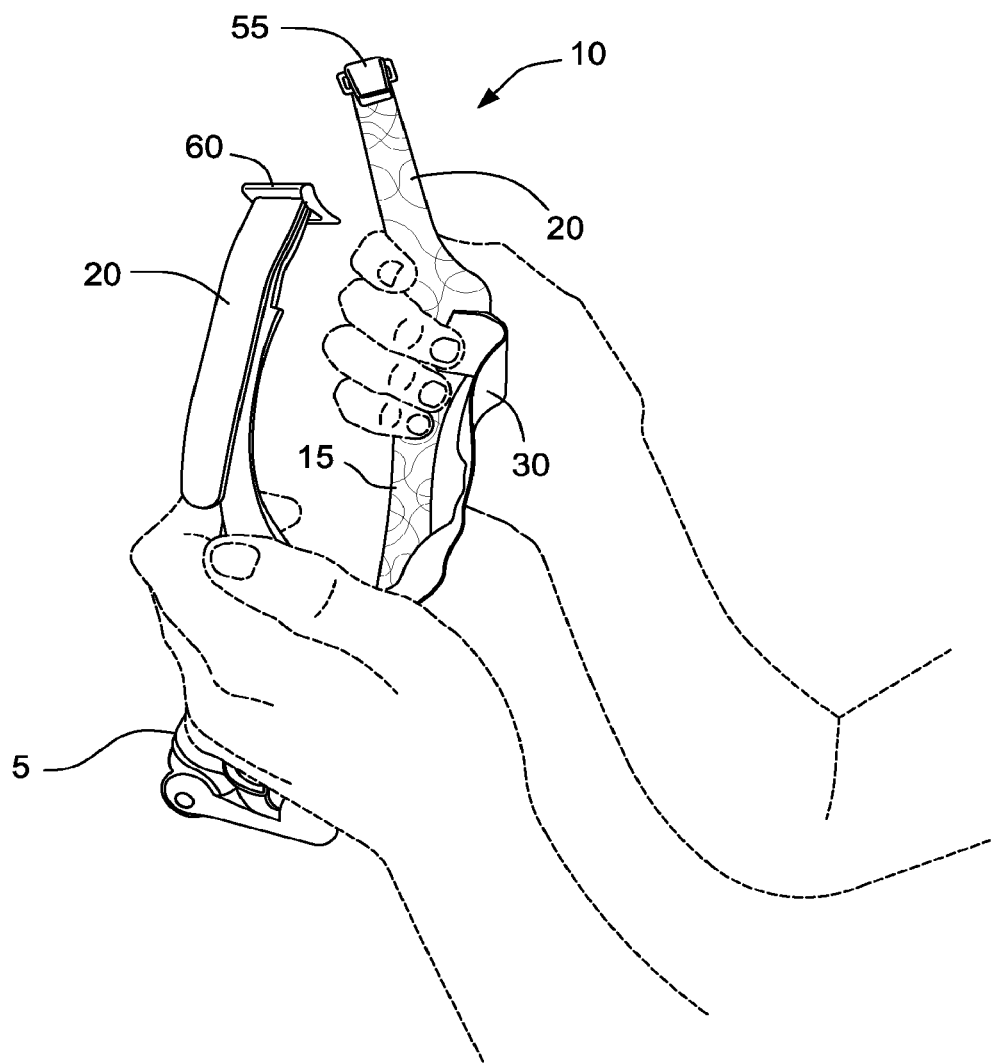
Figure 135:
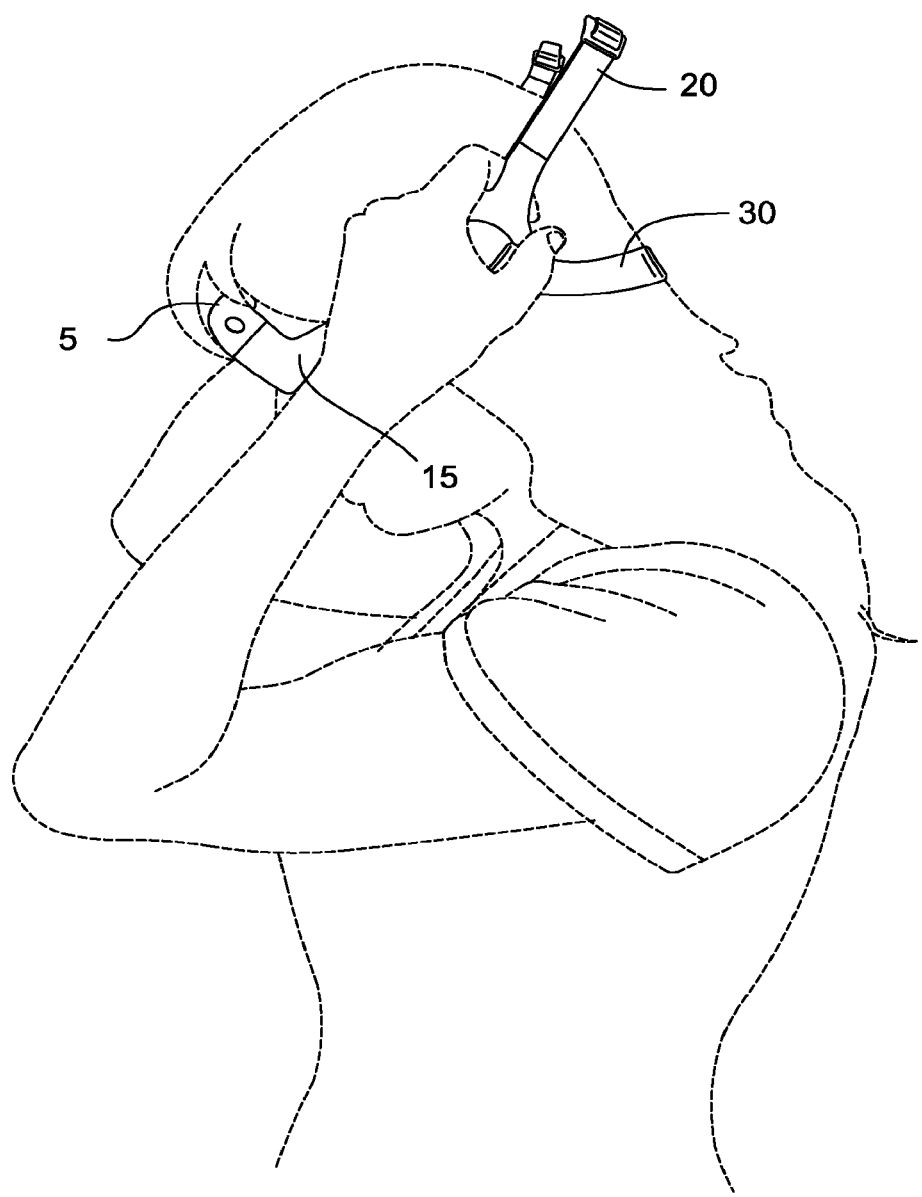
Figure 136:
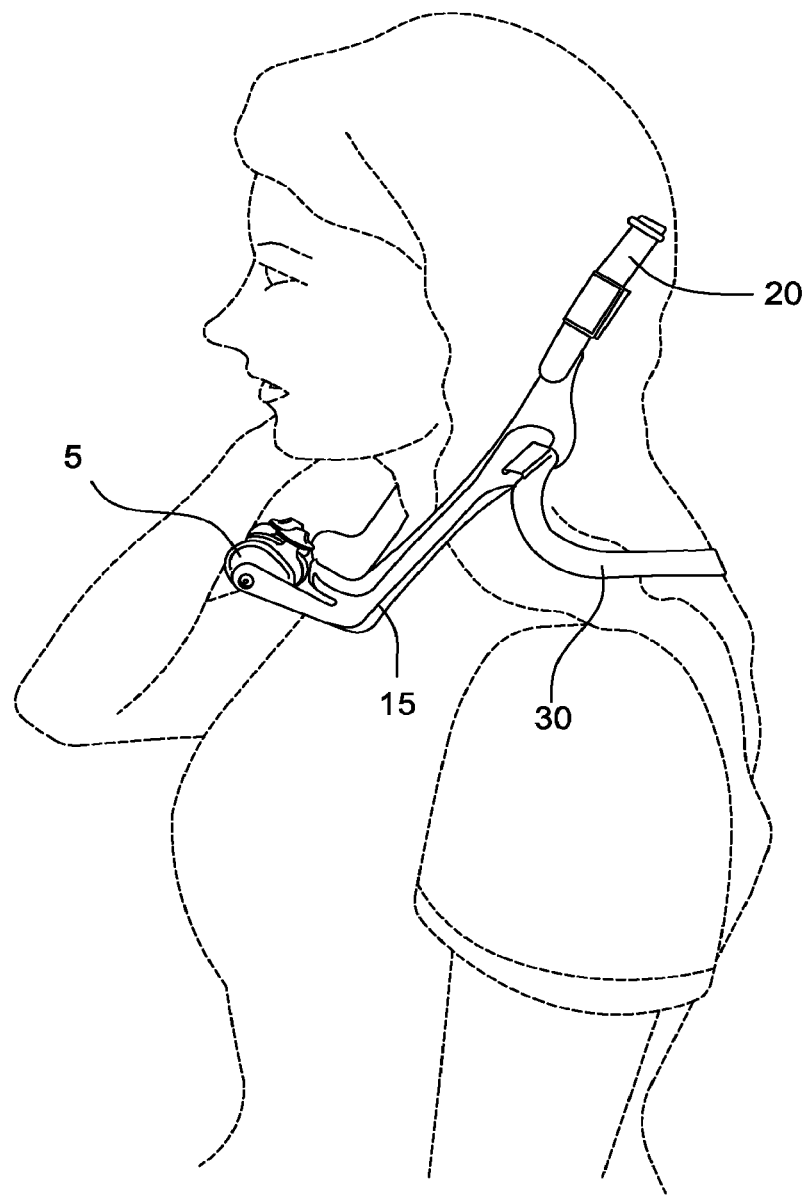
Figure 137:
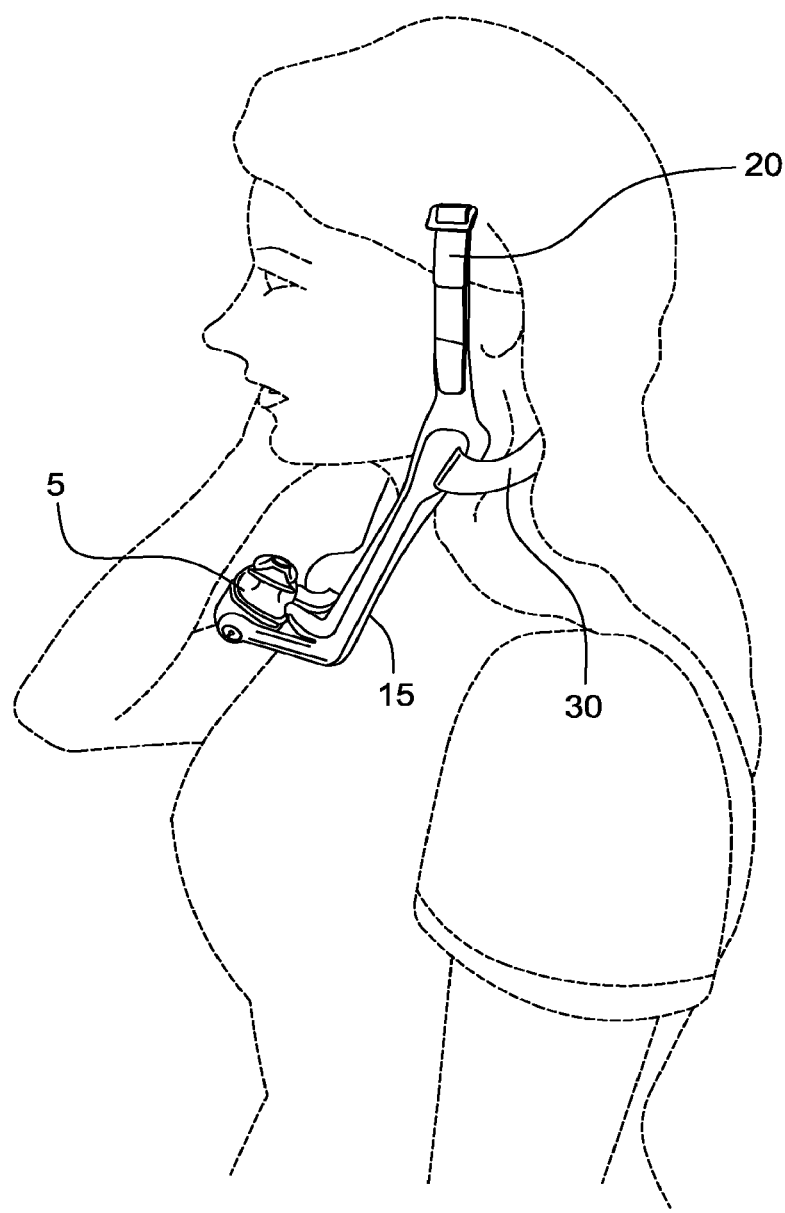
Figure 138:
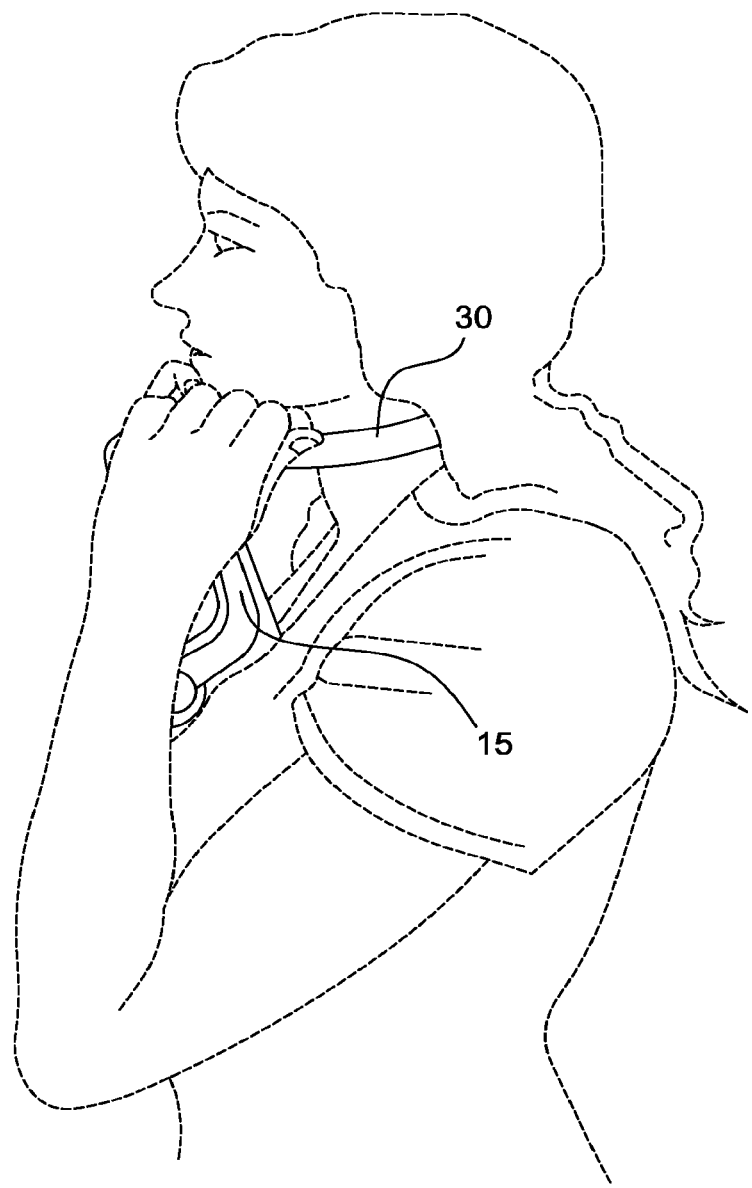
Figure 139:
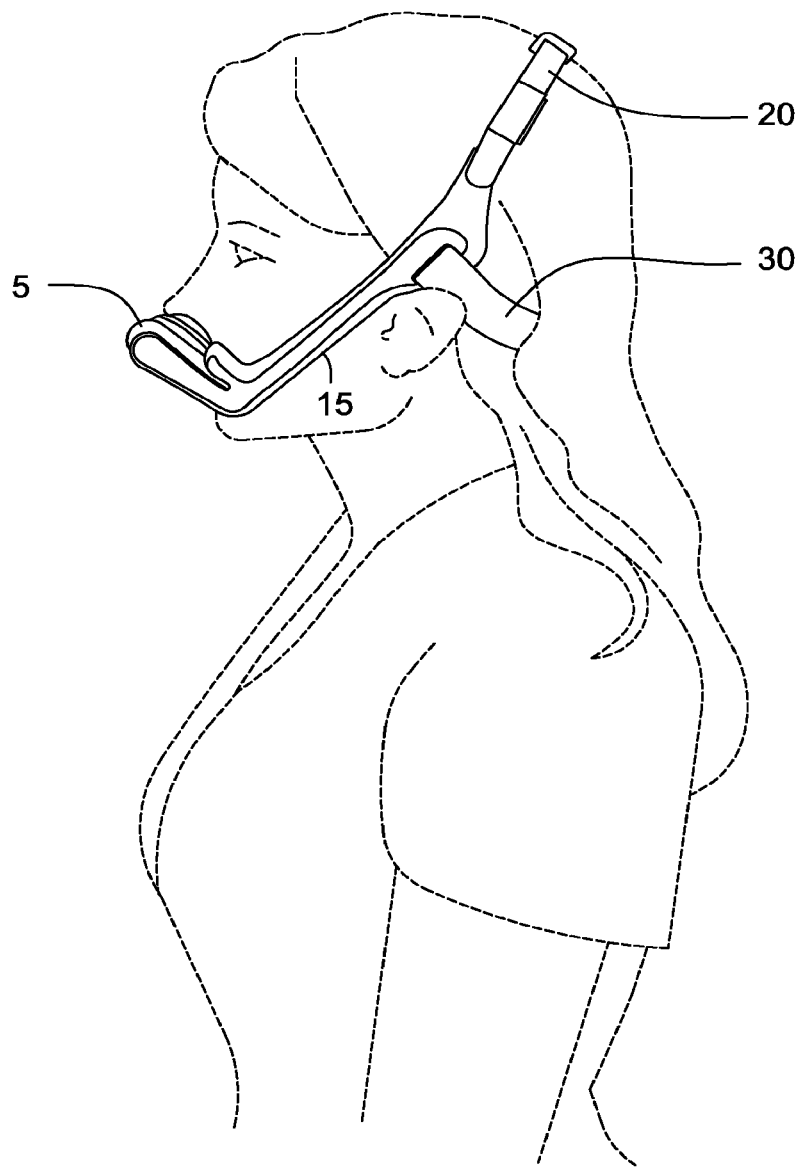
Figure 140:
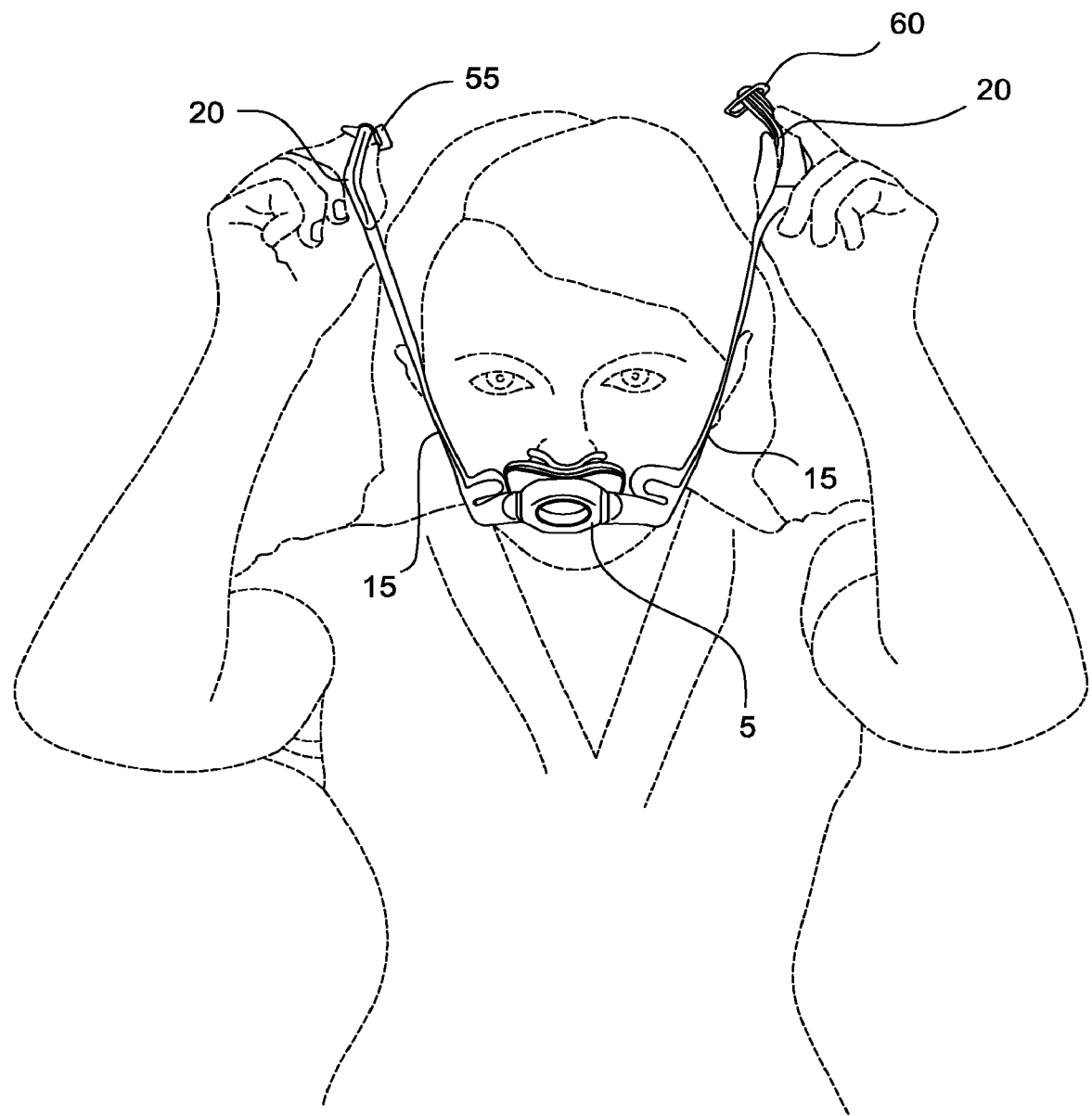
Figure 141:
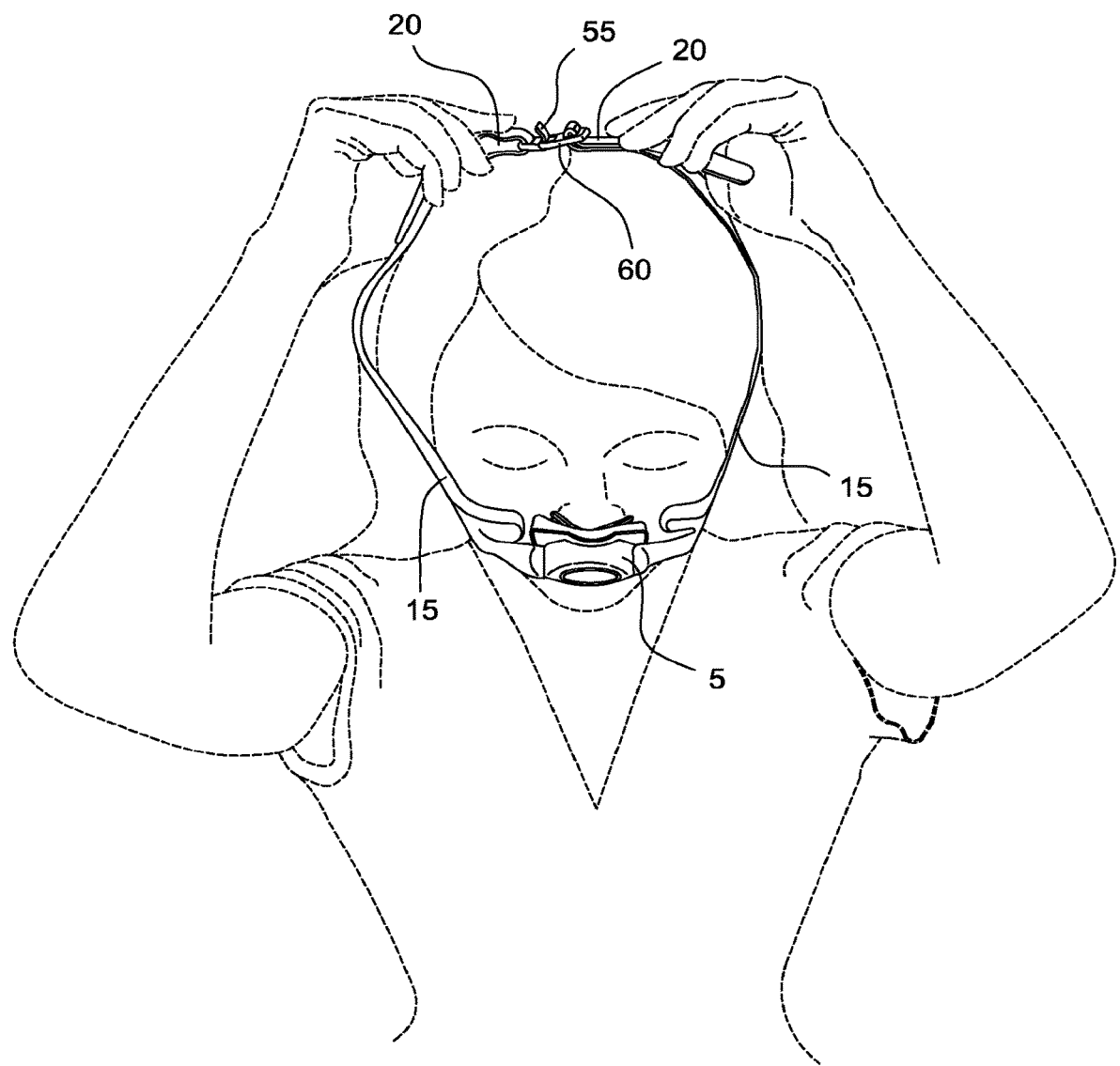
Figure 142:
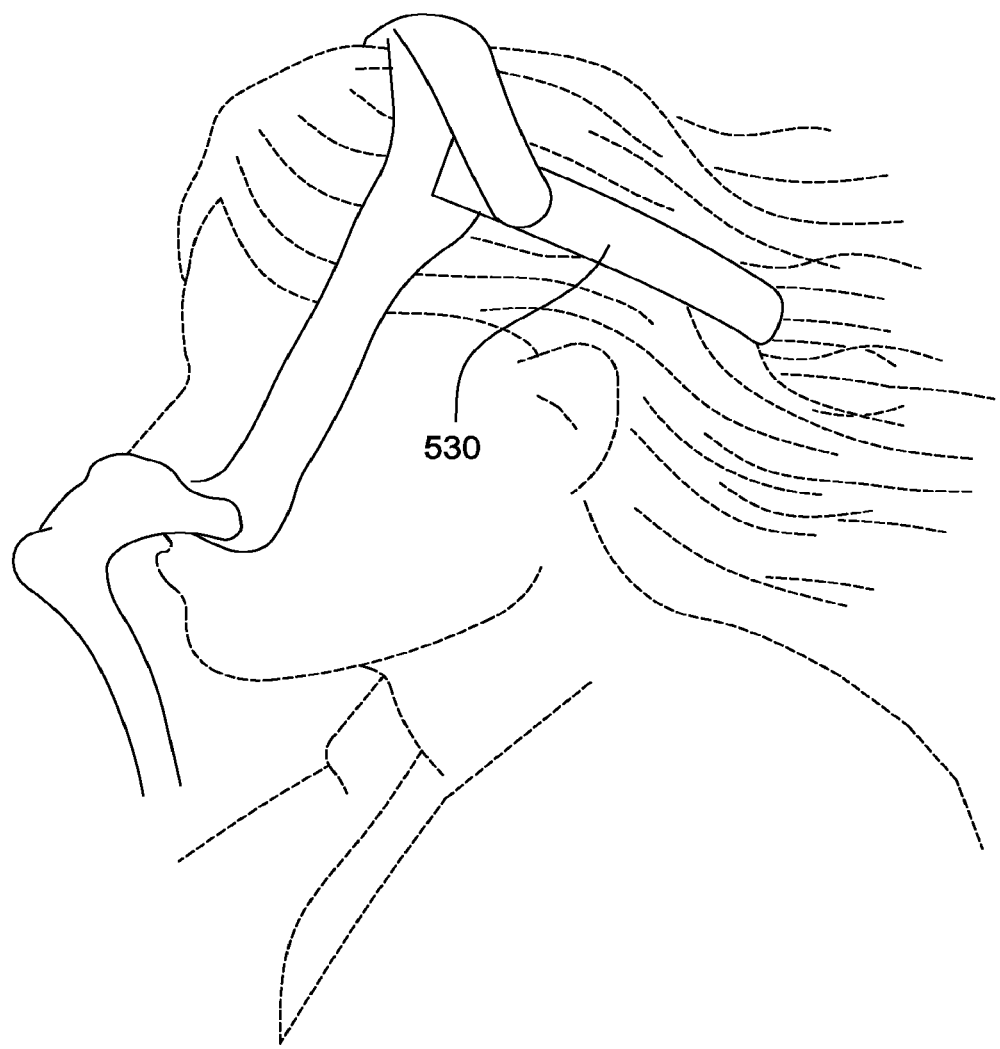

FIG. 126 is a perspective view of a buckle for headgear according to another embodiment of the present invention;

FIG. 127 is a perspective view of a clasp for headgear according to another embodiment of the present invention;

FIG. 128 is a perspective view of a clasp for headgear according to another embodiment of the present invention;

FIG. 129 illustrates a first step of a method for donning headgear of a respiratory mask according to an embodiment of the invention, the headgear comprising a hair band top strap where the patient holds the respiratory mask by the back strap(s) in front of them;

FIG. 130 illustrates a second step of the method of FIG. 129 where the patient inserts their head through the loop created by the hair band and the back strap(s);

FIG. 131 illustrates a third step of the method of FIG. 129 where the patient pulls the headgear down over their head;

FIG. 132 illustrates a fourth step of the method of FIG. 129 where the patient slides the hair band up over their face and forehead;

FIG. 133 illustrates a fifth step of the method of FIG. 129 where the headgear is located in an in-use position;

FIG. 134 illustrates a first step of a method for donning headgear of a respiratory mask according to another embodiment of the present invention, the headgear comprising top straps that clip together where the patient holds the respiratory mask in front of them;

FIG. 135 illustrates a second step of the method of FIG. 134 where the patient is inserting their head through the loop formed by the back strap, front straps and airway interfacing portion;

FIG. 136 illustrates a third step of the method of FIG. 134 where the patient has pulled the respiratory mask over their head;

FIG. 137 illustrates a fourth step of the method of FIG. 134 where the patient has pulled her hair up and over the top of the back strap;

FIG. 138 illustrates a fifth step of the method of FIG. 134 where the patient is holding the front strap and starting to lift the respiratory mask upwards by the front strap;

FIG. 139 illustrates a sixth step of the method of FIG. 134 where the respiratory mask is temporarily located over the patient's ears without the patient needing to hold it there;

FIG. 140 illustrates a seventh step of the method of FIG. 134 where the patient is holding one of the top straps in each hand above her head and moving them towards each other;

FIG. 141 illustrates an eighth step of the method of FIG. 134 where the patient is moved the top straps to a position adjacent each other near the crown of their head and has just connected the clip; and FIG. 142 illustrates a mask and the problematic displacement of the hair by a typically positioned back strap.

DETAILED DESCRIPTION OF ILLUSTRATED EMBODIMENTS

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

Referring to FIGS. 1 to 6, headgear 10 for a respiratory mask is shown according to an embodiment of the present invention. The headgear 10 is especially adapted to be worn by a person having long hair and to properly stabilise the respiratory mask on the person's head. The particular type of headgear depicted is of a type used with respiratory masks for treating sleep disordered breathing.

While the headgear is described as being especially adapted for people having long hair, it should be appreciated that the headgear may be used by people having any suitable hair length and/or hair style (e.g., person having short hair or even no or minimal hair). Also, it should be appreciated that the headgear may be adapted for use with any suitable mask, e.g., full-face, nasal, pillows, etc.

As described in greater detail below, the following provides headgear embodiments that are constructed and arranged to reduce facial marking, facilitate fitting, and provide hair management.

1. General Structure

As shown in FIGS. 1-6, the headgear 10 comprises two front straps 15, two top straps 20, a clasp or clip 25, and a back strap 30. Each of the front straps 15 has a front end 35 that connects to or is integral with a frame or cushion (e.g., airway interfacing portion) of the respiratory mask and a rear end 40 that connects to or is integral with a lower end 45 of the respective top strap 20. Each of the top straps 20 also has an upper end 50. The upper end 50 of the one of the top straps 20 passes through a male clasp portion 55 of clasp 25 while the upper end 50 of the other of the top straps 20 passes through a female clasp portion 60 of clasp 25. The male and female clasp portions 55, 60 are adapted to releasably connect to each other to form the clasp 25 as described in greater detail below.

The back strap 30 has ends 70 that are connected to respective rear ends 40 of the front straps 15. In other embodiments, the back strap 30 may be connected to respective lower ends 45 of the top straps 20. In yet another alternative, the front straps, top straps, and/or back strap may be integrally formed in one piece.

The front straps 15 are adapted to extend from near the patient's nose or mouth, over the patient's cheeks to a location at or adjacent the patient's ears. In the illustrated embodiment, each of the rear ends 40 of the front straps 15 includes a depending portion or tail portion 75 that extends over the top of the patient's ear and at an angle rearwardly and downwardly behind the patient's ears. The tail portion 75 is located at or near the junction of the front straps 15 and the top straps 20. The ends 70 of the back strap 30 connect to the tail portions 75 such that the back strap is disposed at about 70 to 110 degrees to the angle of the front straps 15, at about 160 to 180 degrees to the angle of the top straps 20 and/or at about 30 to 60 degrees to a horizontal plane of the patient's head (i.e., the transverse plane).

In one embodiment, the tail portions 75 are relatively thicker or stiffer than the back straps 30 in use. This helps the tail portions 75 direct the back straps 30 into their correct position.

1.1 Back Strap

In the illustrated embodiment, the back strap 30 is made from a flexible, elastic material and is adapted to locate underneath a patient's long hair and press against a lower region of a patient's occiput or their upper neck and/or urge upwardly against the patient's hair itself from underneath in use. When used on a person who has short hair or who is bald, the back strap 30 is adapted to urge against the patient's head beneath their occiput.

In the illustrated embodiment, the tail portions 75 are not tensioned against the patient's ears in use to avoid discomfort.

The join lines between the ends 70 of the back strap 30 and respective tail portions 75 are disposed at an angle other than substantially perpendicular to the general axial direction of the back strap 30. That is, the back strap 30 may be co-linear with the tail portions 75 when viewed from the side (e.g., refer to FIG. 3) but the join line is preferably disposed at an angle closer to the vertical plane of the patient's head (i.e., the frontal plane). This allows the back strap 30 to better conform to the generally spherical shape of the human head and so provide a more even force distribution on the patient's head. Another benefit of this arrangement is that when the mask is held off one's head it adopts an in-use shape allowing it to be more easily donned.

Embodiments of the invention may have a back strap 30 with a spring constant of between 0.001 N/mm and 1 N/mm, e.g., between 0.007 N/mm and 0.07 N/mm (e.g., about 0.02 N/mm).

In one embodiment, the elasticity of the back strap 30 provides the only adjustment for allowing the mask to fit differently sized/shaped heads.

The back strap 30 helps the headgear 10 to properly stabilise on a patient having long hair and so is able to hold the airway interfacing portion more stably on the patient's face in use.

Figure 1:
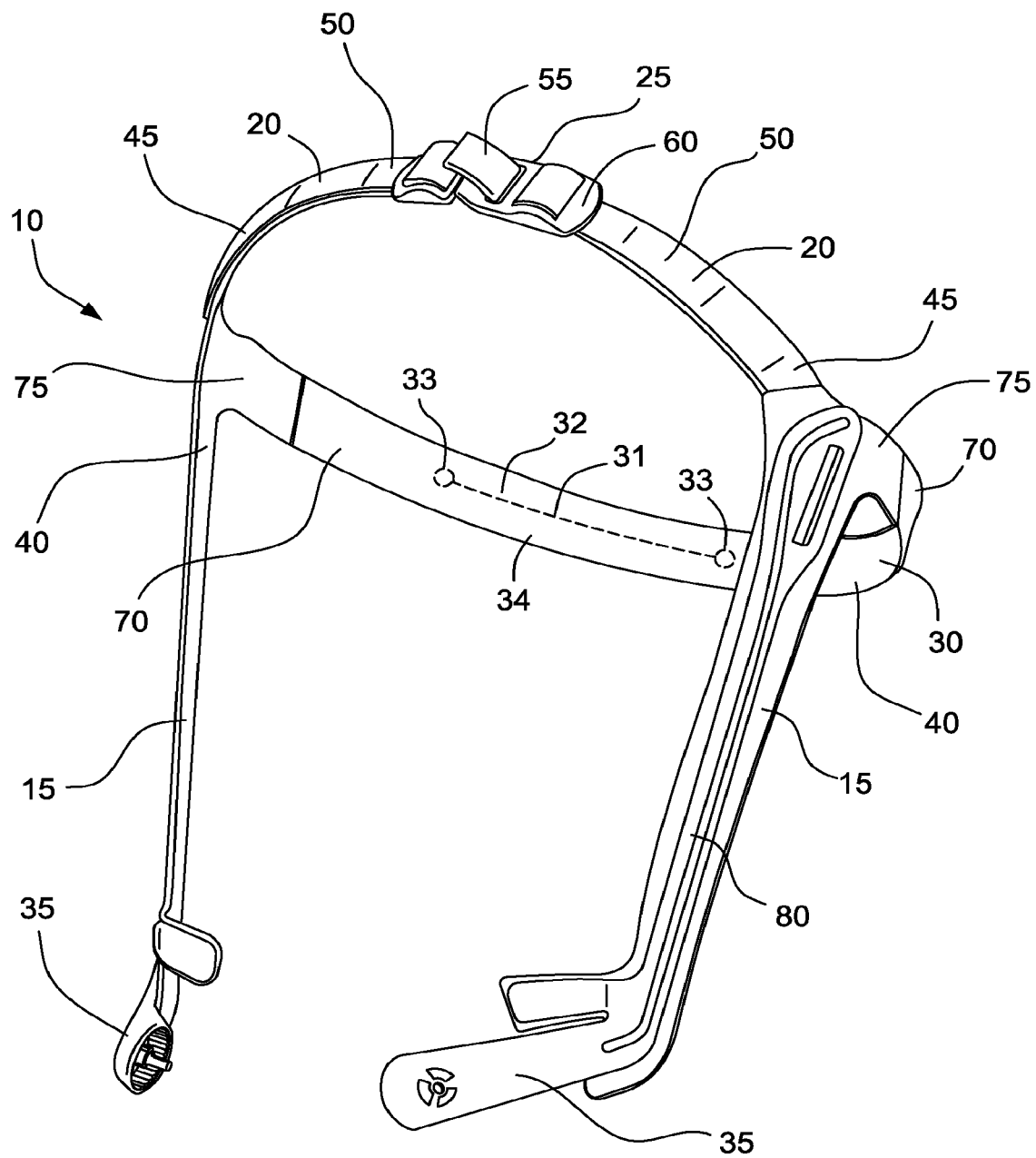
FIG. 1 shows a left-side perspective view of headgear for a respiratory mask in accordance with an embodiment of the invention.

In one embodiment, as shown in dashed lines in FIG. 1, the back strap 30 may include a middle portion having a longitudinal slit 31 therealong defining an upper back strap portion 32 and a lower back strap portion 34 which splay apart in use such that the back strap grips the head and/or hair better to stabilise the headgear. The slit 31 may comprise key-hole shaped enlarged radii 33 at its ends.

In one embodiment, the back strap subtends an angle of between 60 and 100 degrees with respect to the front strap. In an exemplary embodiment, this angle is about 80 degrees. In another embodiment, the back strap subtends an angle of between 110 and 180 degrees with respect to the top strap. In an exemplary embodiment, this angle is about 150 degrees.

Figure 7:
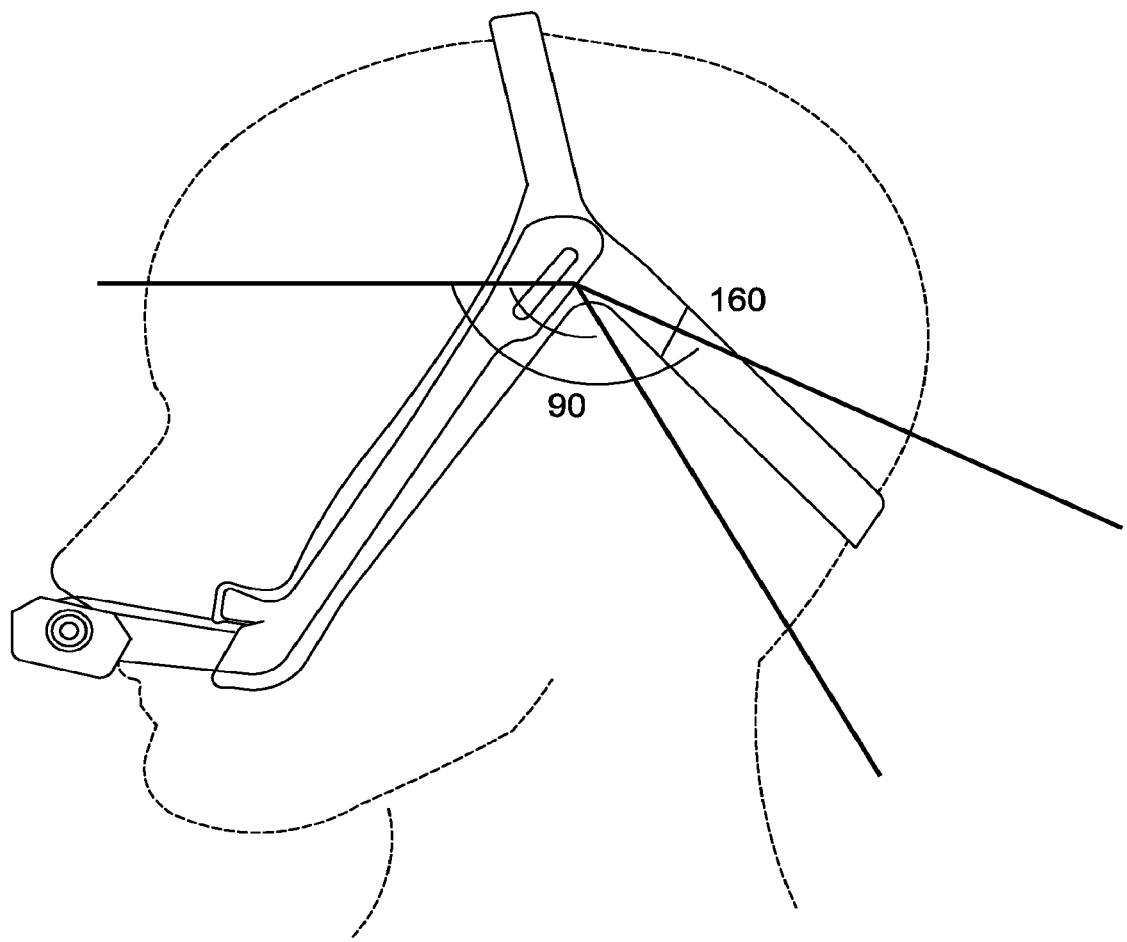
FIG. 7 shows a side view of the headgear of FIG. 1 and in particular a range of angles the back strap may subtend with respect to a horizontal plane through the patient's head in accordance with embodiments of the invention.

Referring to FIG. 7, the back strap subtends an angle of between 90 and 160 degrees with respect to the horizontal datum for the human head (i.e., the transverse plane).

In one embodiment, the back straps 30 are made from a material that obeys Hooke's Law. In other embodiments, the back straps 30 are simply made from a readily stretchable material. In an embodiment, the back straps 30 do not reduce in width as they are pulled.

1.2 Rigidisers

In the illustrated embodiment, thin rigidisers 80 are attached to respective front straps 15 for stiffening, stabilising, locating and/or curving the front straps 15. The rigidisers 80 help hold the headgear in an open form when it is not in use to make it easier for a patient to don the mask.

The rigidisers 80 have a thin width of between 2 mm and 25 mm, e.g., between 2 mm and 9 mm. The shape of the rigidisers 80 may also take a curved form to provide feminine aesthetics.

In the illustrated embodiment, the rigidisers have a slot or aperture for connection with a back strap. In an alternative embodiment, this slot may not be included in the rigidizer.

2. Headgear Strap Embodiments

The following illustrates alternative embodiments of headgear straps (e.g., material combinations, socks/covers, etc.) to enhance comfort and reduce facial marking in use. For example, the strap material and/or sock/cover provided to the strap may be constructed of a relatively soft material configured to more evenly distribute load across the patient's face and prevent facial marking in use.

2.1 Strap Materials

FIGS. 8-16 show alternative materials that may be used to construct the front straps of the headgear in order to provide more comfort to the patient. Equally, these materials could be used for any part of the headgear or mask system.

Figure 8:
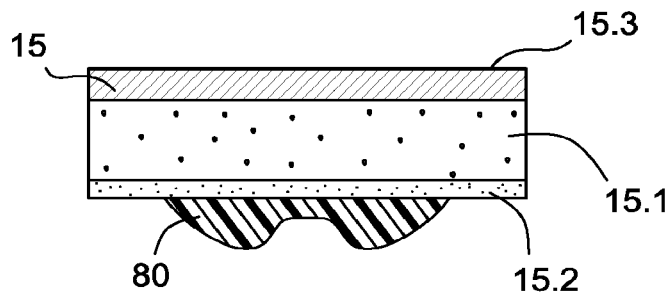
FIG. 8 is a cross-sectional view of a front headgear strap and rigidiser according to an embodiment of the present invention.

FIG. 8 shows a front strap 15 constructed of Breath-O-Prene™ with an inner layer 15.1 of Breath-O-Prene™ foam, an outwardly facing layer 15.2 of Breath-O-Prene™ Lycra, and a face contacting layer 15.3 of fleece, deep pile textile, brushed Lycra, or unbroken loop (UBL) laminated material that forms the skin contacting face of the Breath-O-Prene™. These materials may provide more comfort to the patient.

Figure 9:
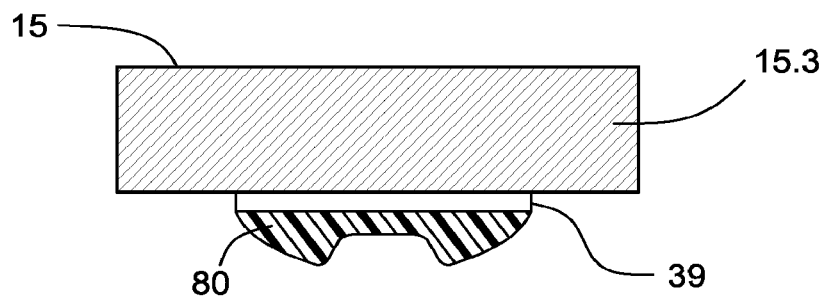
FIG. 9 is a cross-sectional view of a front headgear strap and rigidiser according to another embodiment of the present invention.

FIG. 9 shows a front strap 15 with a face contacting side 15.3 constructed of thick fleece or a deep pile textile for comfort. The rigidizer 80 may be adhered to the strap 15, e.g., by double sided tape 39.

Figure 10:
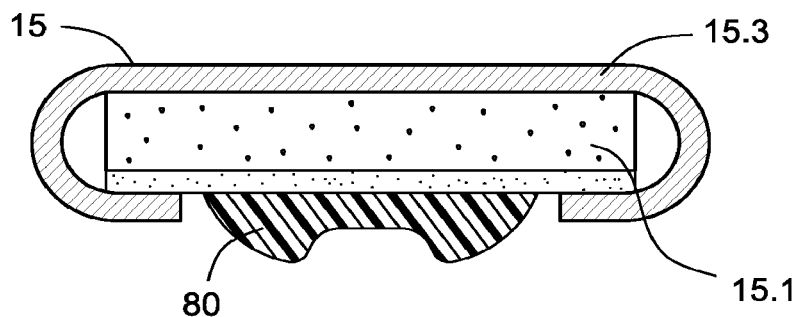
FIG. 10 is a cross-sectional view of a front headgear strap and rigidiser according to another embodiment of the present invention.

FIG. 10 shows a front strap 15 including Breath-O-Prene™ foam 15.1 and an outer face contacting layer 15.3 of Lycra material wrapped around the Breath-O-Prene™ foam 15.1 (e.g., Lycra layer laminated to Breath-O-Prene™ foam and rolled around the edge). The rigidizer 80 may be secured to the strap 15 by stitching.

Figure 11:
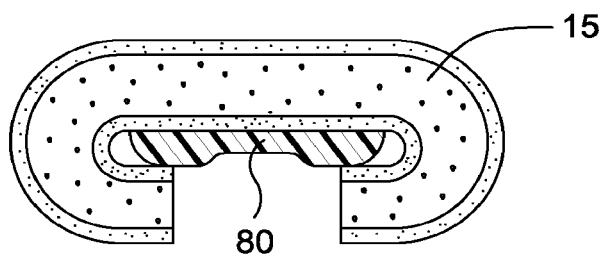
FIG. 11 is a cross-sectional view of a front headgear strap and rigidiser according to another embodiment of the present invention.

FIG. 11 shows a front strap 15 constructed of standard Breath-O-Prene™ and at least partially wrapped or rolled around the edges of the rigidizer 80. The front strap 15 may be adhered to the rigidizer 80 by an adhesive/tape or may be stitched to the rigidizer 80.

Figure 12:
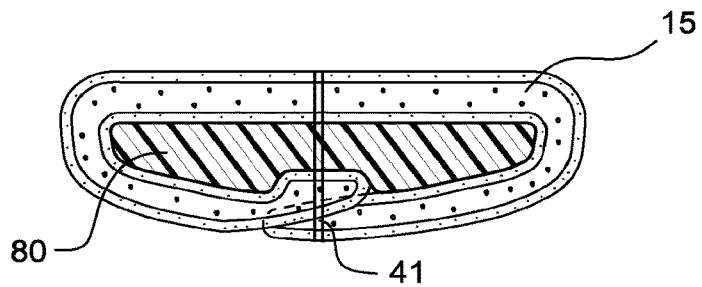
FIG. 12 is a cross-sectional view of a front headgear strap and rigidiser according to another embodiment of the present invention.

FIG. 12 shows a similar concept to FIG. 11, however the Breath-O-Prene™ is entirely wrapped or rolled around the rigidizer 80. In addition, the Breath-O-Prene™ is stitched to the rigidizer 80 at the center by a single stitch 41 that extends through the rigidizer 80 and all the layers of the Breath-O-Prene™. However, the Breath-O-Prene™ and rigidizer 80 may be secured by any other suitable means, e.g., gluing.

Figure 13:
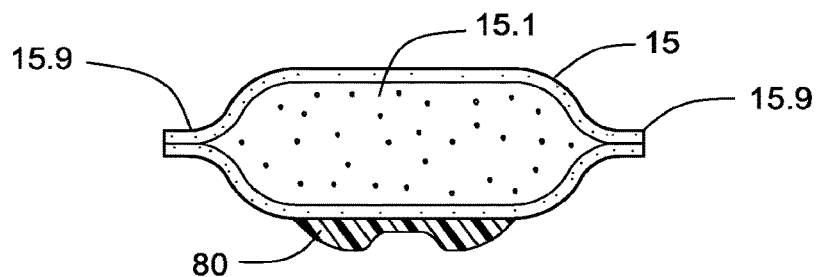
FIG. 13 is a cross-sectional view of a front headgear strap and rigidiser according to another embodiment of the present invention.
Figure 14:
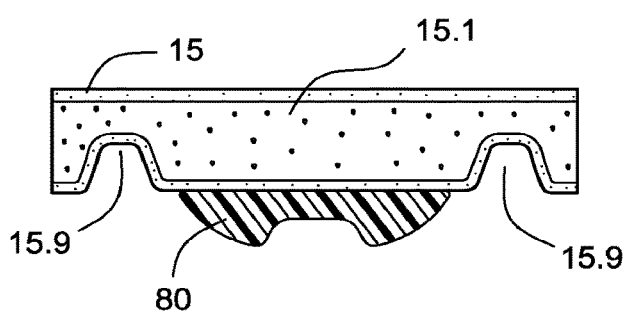
FIG. 14 is a cross-sectional view of a front headgear strap and rigidiser according to another embodiment of the present invention.

FIGS. 13 and 14 show a front strap 15 with thermoformed edges. For example, FIG. 13 shows Breath-O-Prene™ foam 15.1 with thermoformed edges 15.9 to elevate the edges away from the patient's face, and a rigidizer 80 secured to the Breath-O-Prene™ foam 15.1, e.g., by stitching. FIG. 14 shows Breath-O-Prene™ foam 15.1 with thermoformed edges 15.9 to create "living hinge" style stress relief and create softer edges against the patient's face, and a rigidizer 80 secured to the Breath-O-Prene™ foam 15.1, e.g., by stitching. It should be appreciated that a front strap constructed of Breath-O-Prene™ or any other suitable material may be provided with thermoformed edges.

Figure 15:
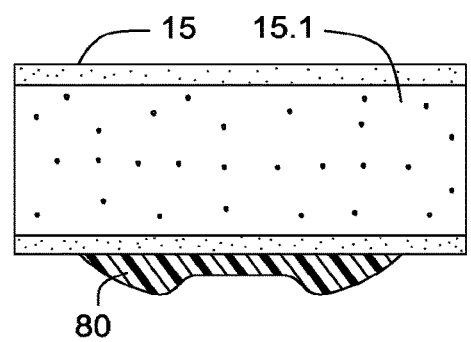
FIG. 15 is a cross-sectional view of a front headgear strap and rigidiser according to another embodiment of the present invention.

FIG. 15 shows a front strap 15 constructed of Breath-O-Prene™ foam 15.1 with a thicker foam through the center and/or a softer density foam through the center. The Breath-O-Prene™ foam 15.1 may be laminated with Lycra on either side. In an embodiment, the Breath-O-Prene™ foam 15.1 may have 3 to 7 pound density and/or 2.5 to 8 mm thickness. The rigidizer 80 secured to the Breath-O-Prene™ foam 15.1, e.g., by stitching.

Figure 16:
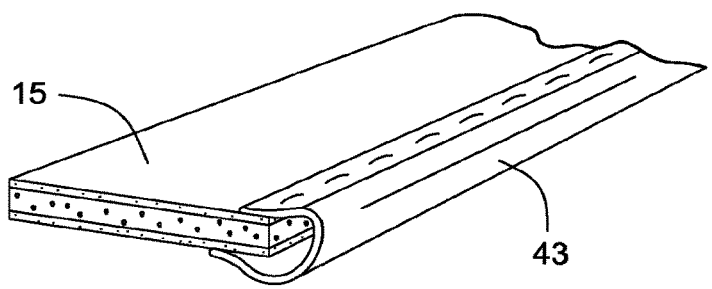
FIG. 16 is a cross-sectional view of a front headgear strap and rigidiser according to another embodiment of the present invention.

FIG. 16 shows a front strap 15 (e.g., constructed of Breath-O-Prene™) with soft piping 43 along the edges to avoid discomfort and potential red marks on the user's face.

2.2 Strap Size

In an embodiment, headgear may include thin front straps having a width of between 2 mm and 30 mm to minimise visual impact and impact on hair styling. In an exemplary embodiment, the width of the front straps is about 19 mm wide. In another embodiment, the width of the front straps is about 20 mm wide. In another embodiment, the width of the front straps is about 25 mm wide. FIG. 17 illustrates the comparison between a front strap 15 having a width w1 of about 19-20 mm and a wider front strap having a width w2 of about 25 mm. In an embodiment, the thin front straps may not be wider than the rigidisers 80, e.g., equal to or less than the rigidizer width.

2.3 Notches

In an alternative embodiment, the front straps may have notches or scalloped edges. This may alter the stresses in the headgear material and make it more comfortable for the patient in use. There may be one or more notches provided to the front straps. For example, FIG. 18 shows a front strap 15 including a single deep notch 16 cut out at the cheek support, and FIG. 19 shows multiple notches 16 at various intervals on the front strap 15. It should be noted that the notches may be regularly or irregularly spaced along the headgear straps. It should also be noted that one or more notches may be provided to any of the headgear straps.

2.4 Covers or Sleeves

Figure 20:
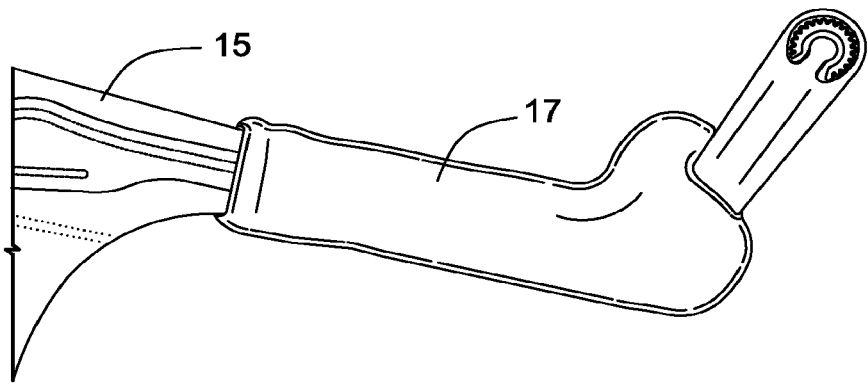
FIG. 20 is a side view of a front headgear strap with a slip-on sleeve in the facial area only according to an embodiment of the present invention.
Figure 21:
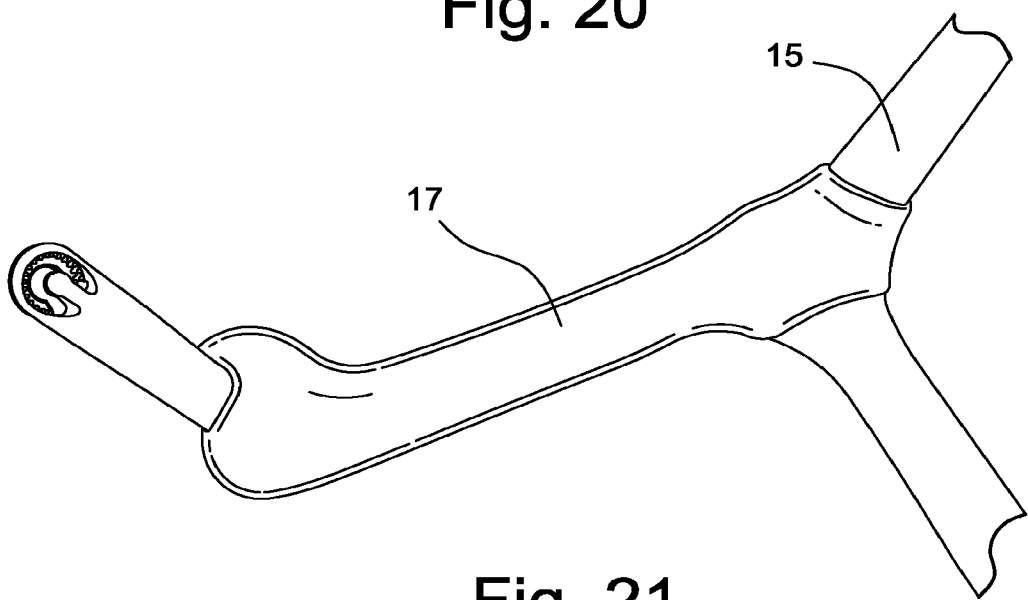
FIG. 21 is a side view of a front headgear strap with a slip-on sleeve along the full length of the rigidizer according to an embodiment of the present invention.

Covers or sleeves may be provided to the front straps to provide comfort for the patient. The covers may extend along a portion or all of the front straps. For example, FIG. 20 illustrates a slip-on sleeve 17 provided to the front strap 15 in the facial area only, and FIG. 21 illustrates a slip-on sleeve 17 provided to the front strap 15 along the full length of the rigidiser extending along the front strap. In an embodiment, the covers may be continuous with a headband provided to the top strap. The covers or sleeves may be comprised of a suitably comfortable material, e.g., gel, suede, foam, etc. In an embodiment, the front strap may not be provided, e.g., cover surrounding rigidizer. In addition, the covers or sleeves may be structured so that they can be removable, washable, and reattachable.

Figure 22:
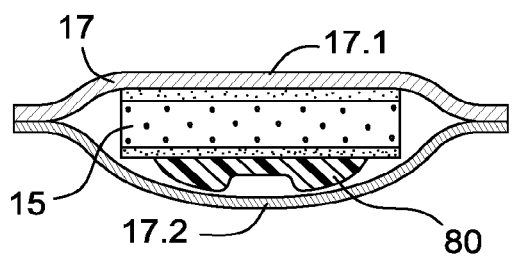
FIG. 22 is a cross-sectional view of a front headgear strap and sleeve according to an embodiment of the present invention.

FIG. 22 shows a cross-section of the possible combinations of materials that may be used for the sleeves or covers to provide comfort to the patient. In this embodiment, the sleeve 17 covering the front strap 15 (e.g., constructed of Breath-O-Prene™) and rigidiser 80 includes a skin contacting side 17.1 constructed of fleece material/deep pile textile or similar material and outwardly facing side 17.2 constructed of Lycra or similar material.

Figure 23:
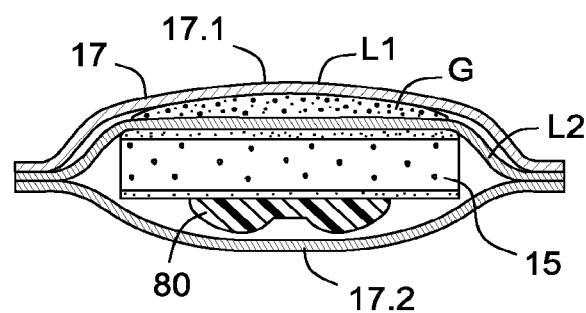
FIG. 23 is a cross-sectional view of a front headgear strap and sleeve according to another embodiment of the present invention.

FIG. 23 shows a cross-section of material combinations that may be used in the sleeve including a gel or low durometer silicone. In this embodiment, the sleeve 17 covering the front strap 15 (e.g., constructed of Breath-O-Prene™) and rigidiser 80 includes skin contacting side 17.1 with first and second layers L1, L2 constructed of Lycra or similar material that enclose a gel/low duro silicone G and an outwardly facing side 17.2 constructed of Lycra or similar material.

FIGS. 24-74 illustrate alternative front strap arrangements to provide more comfort to the patient, e.g., along the cheek region of the headgear.

Figure 25:
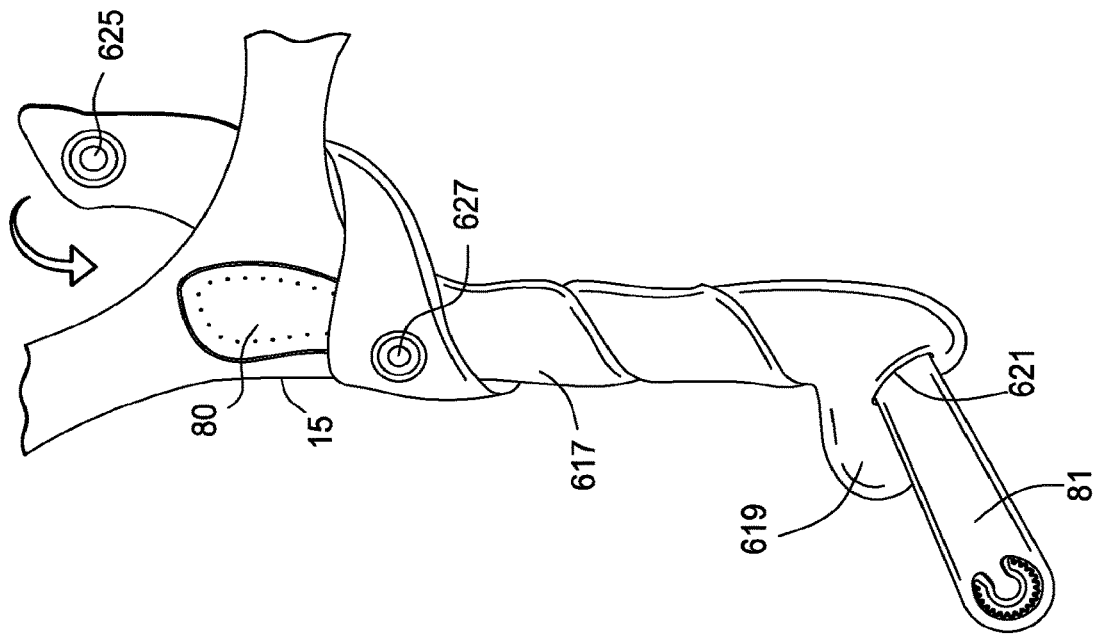
FIG. 25 is a side view of the front headgear strap and wrap of FIG. 24 with the wrap partially unwrapped.
Figure 24:
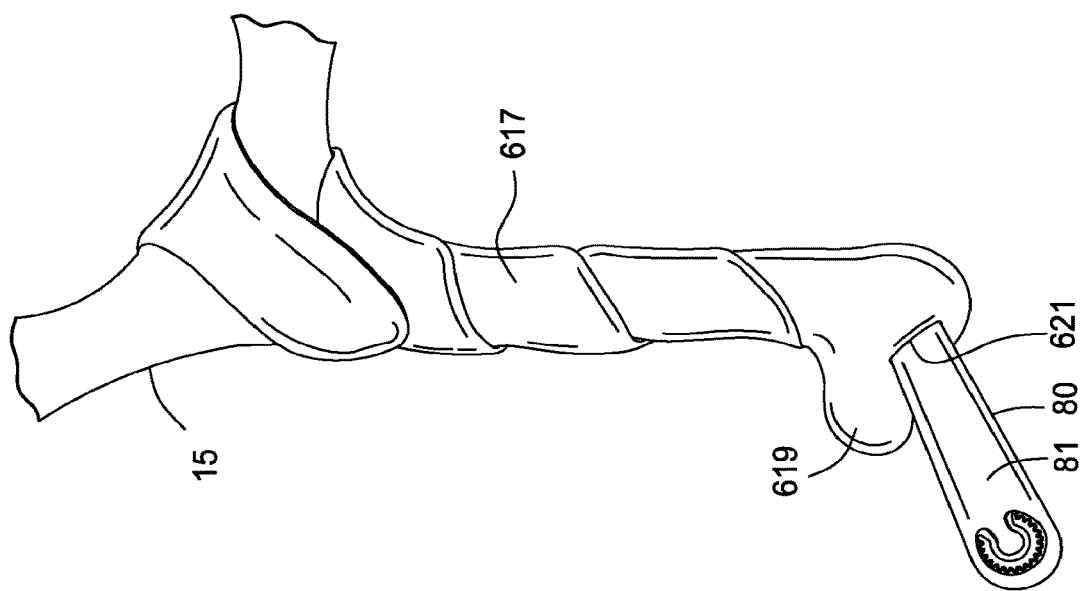
FIG. 24 is a side view of a front headgear strap and wrap according to an embodiment of the present invention.

FIGS. 24 and 25 illustrate a front strap 15 with a length of material 617 wrapped around the front strap 15, e.g., in a spiralling action. As illustrated, one end portion of the material 617 includes a pocket 619 to receive the end of the front strap and a slot 621 to allow the frame engaging end 81 of the rigidizer 80 to extend therethrough. The opposing end portion of the material 617 includes a fastener (e.g., first button fastener 625 adapted to engage a second button fastener 627 along the length of the material) to secure the wrap in position.

FIGS. 26 and 27 illustrate a front strap 15 provided within a sleeve or cover 717. The sleeve 717 provides a pillowcase type arrangement with a pillowcase type opening 731 that allows the front strap 15 to be assembled into the sleeve. As illustrated, one end portion of the sleeve 717 includes a pocket 719 to receive the end of the front strap and a slot 721 to allow the frame engaging end 81 of the rigidizer 80 to extend therethrough. The opposing end portion of the sleeve 717 includes openings 733, 735 to allow top and back strap portions to extend therethrough. Stitching 732 is provided to each end of the pillowcase type opening 731. In an embodiment, the sleeve 717 includes a face contacting side (non shown) constructed of fleece and a non-face contacting side NFC constructed of Lycra. However, other suitable materials for the sleeve are possible.

Figure 29:
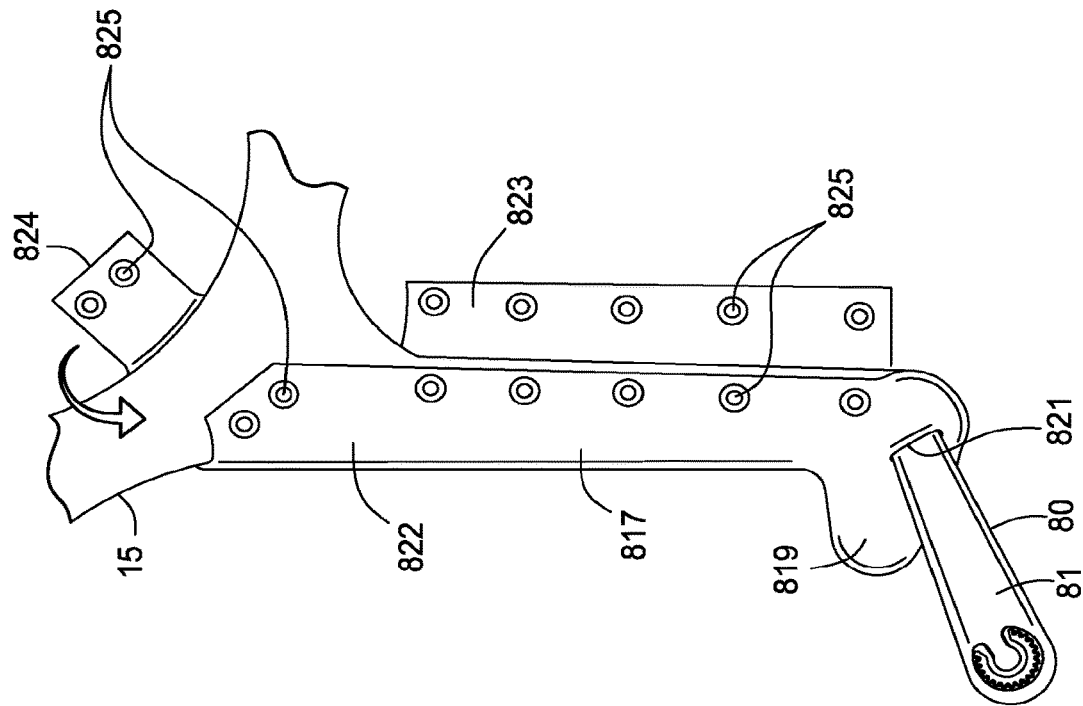
FIG. 29 is a side view of the front headgear strap and sleeve of FIG. 28 with the sleeve unbuttoned.
Figure 28:
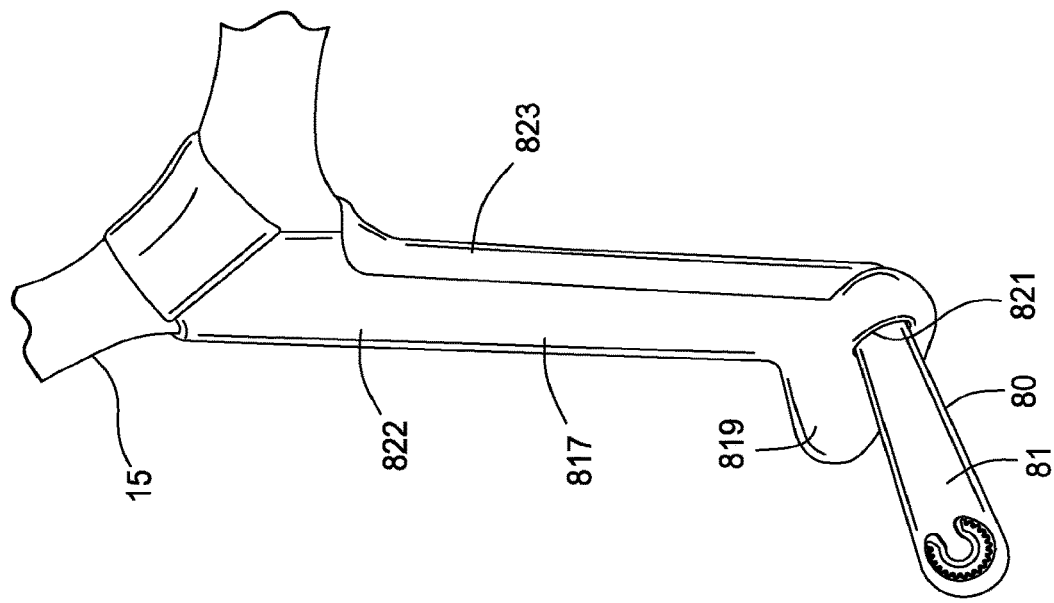
FIG. 28 is a side view of a front headgear strap and sleeve according to another embodiment of the present invention.

FIGS. 28 and 29 illustrate a front strap 15 with a sleeve 817 wrapped around the front strap. As illustrated, the sleeve 817 includes side portions 822, 823 adapted to be wrapped and fastened around the front strap portion of the front strap, e.g., by a plurality of button or snap fasteners 825, and a top portion 824 adapted to be wrapped and fastened around the top strap portion of the front strap, e.g., by a plurality of button or snap fasteners 825. The end portion of the material includes a pocket 819 to receive the end of the front strap and a slot 821 to allow the frame engaging end 81 of the rigidizer 80 to extend therethrough.

Figure 31:
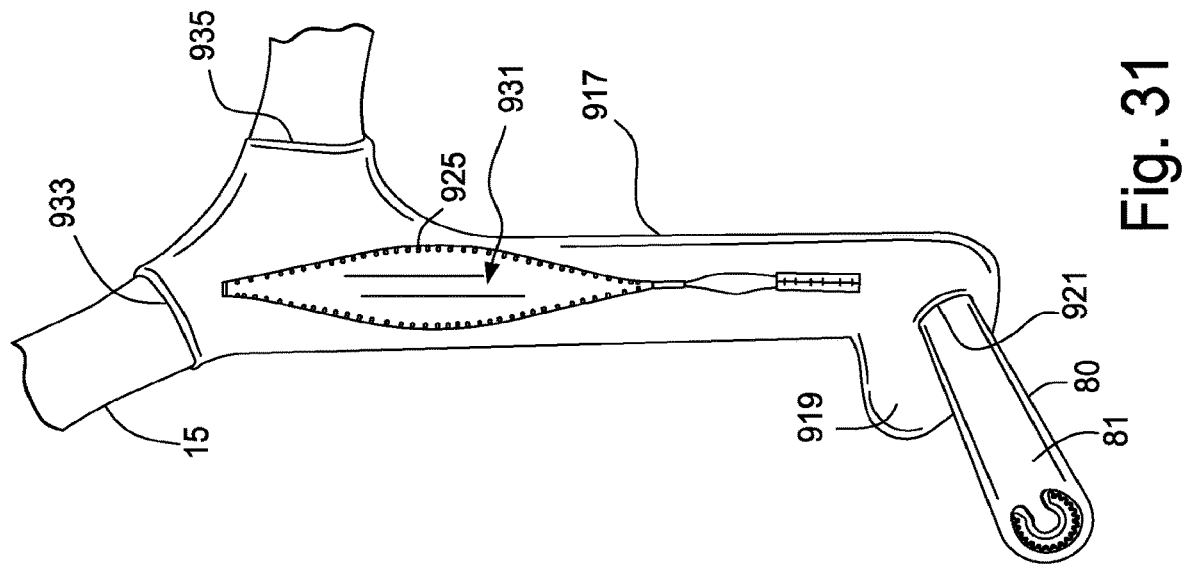
FIG. 31 is a side view of the front headgear strap and sleeve of FIG. 30 with the sleeve partially unzipped.
Figure 30:
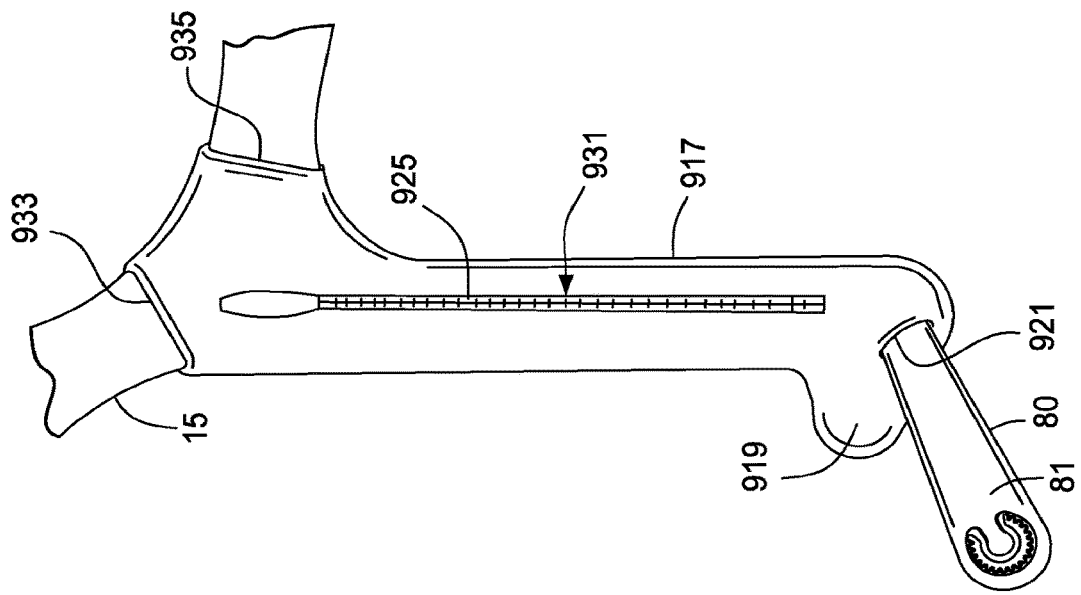
FIG. 30 is a side view of a front headgear strap and sleeve according to another embodiment of the present invention.

FIGS. 30 and 31 illustrate a front strap 15 provided within a sleeve or cover 917. The sleeve 917 provides an opening 931 that allows the front strap to be assembled into the sleeve. The opening 931 is selectively closed by a zipper 925 to secure the sleeve in position. As illustrated, one end portion of the sleeve includes a pocket 919 to receive the end of the front strap and a slot 921 to allow the frame engaging end 81 of the rigidizer 80 to extend therethrough. The opposing end portion of the sleeve includes openings 933, 935 to allow top and back strap portions to extend therethrough.

Figure 33:
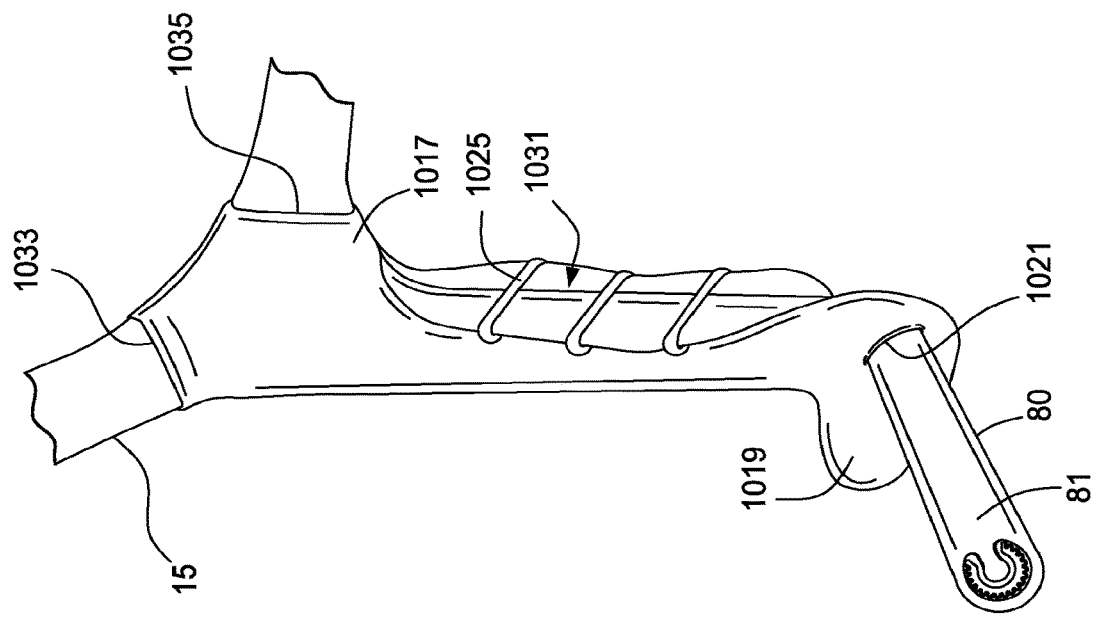
FIG. 33 is a side view of the front headgear strap and sleeve of FIG. 32 with the sleeve partially opened.
Figure 32:
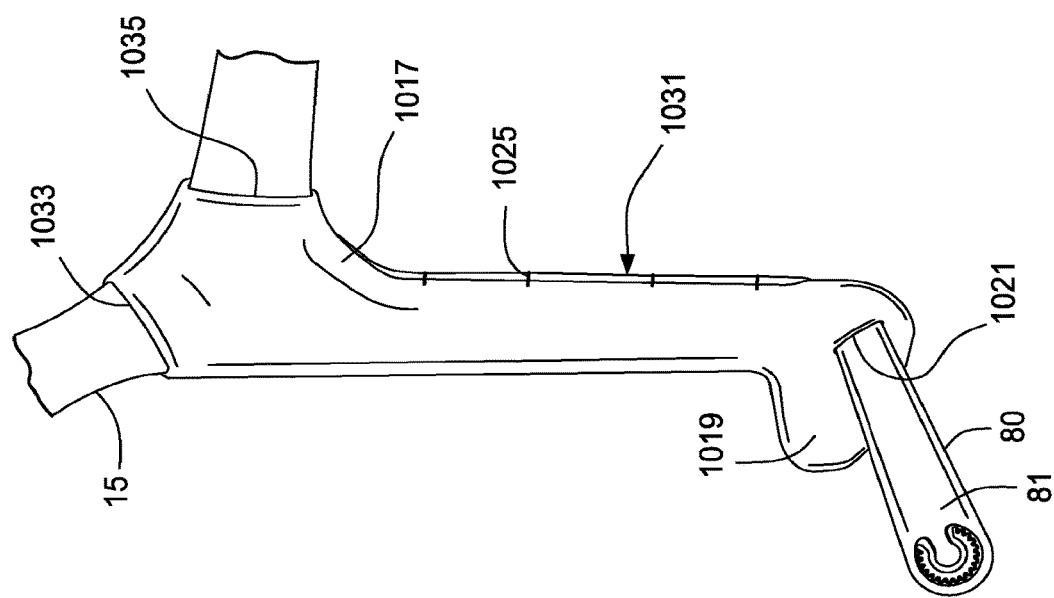
FIG. 32 is a side view of a front headgear strap and sleeve according to another embodiment of the present invention.

FIGS. 32 and 33 illustrate a front strap 15 provided within a sleeve or cover 1017. The sleeve 1017 provides a side opening 1031 that allows the front strap to be assembled into the sleeve. The opening 1031 is closed by an elastic stitch 1025 which stretches to allow assembly of the front strap into the sleeve. As illustrated, one end portion of the sleeve includes a pocket 1019 to receive the end of the front strap and a slot 1021 to allow the frame engaging end 81 of the rigidizer 80 to extend therethrough. The opposing end portion of the sleeve includes openings 1033, 1035 to allow top and back strap portions to extend therethrough.

FIGS. 34 to 36 illustrate a front strap 15 provided within a sleeve or cover 1117. The sleeve 1117 provides a side opening 1131 that allows the front strap to be assembled into the sleeve. The opening 1131 is closed by a snap lock fastener 1125. As shown in FIG. 36, the snap lock fastener 1125 includes a protrusion 1127 on one side of the sleeve that is adapted to interlock with a u-shaped clip portion 1129 on the opposing side of the sleeve. Also, one end portion of the sleeve includes a pocket 1119 to receive the end of the front strap and a slot 1121 to allow the frame engaging end 81 of the rigidizer 80 to extend therethrough. The opposing end portion of the sleeve includes openings 1133, 1135 to allow top and back strap portions to extend therethrough.

Figure 38:
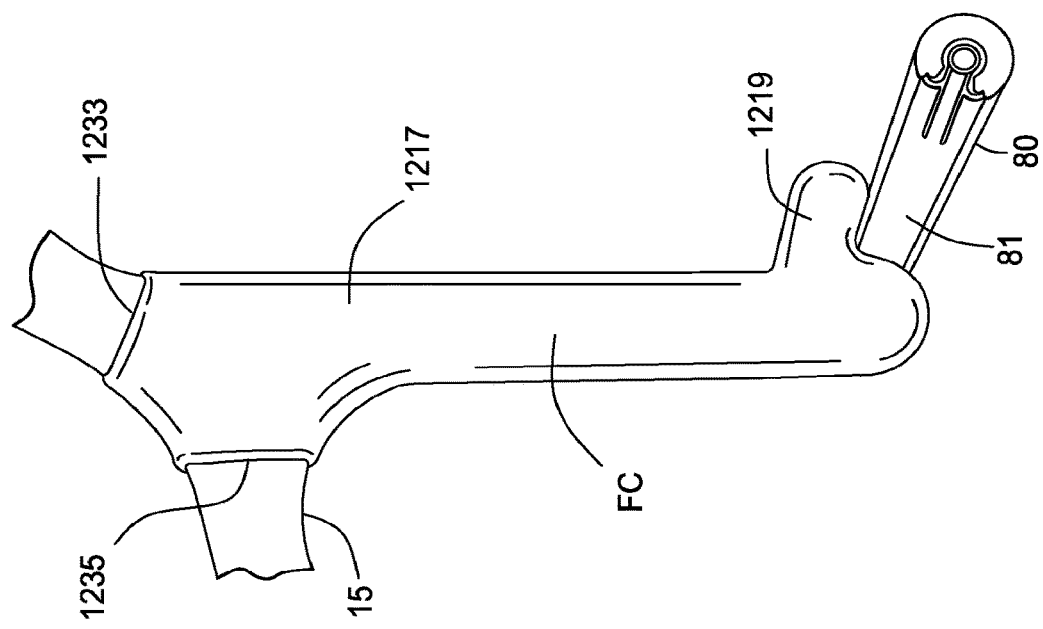
FIG. 38 is an opposing side view of the front headgear strap and sleeve of FIG. 37.
Figure 37:
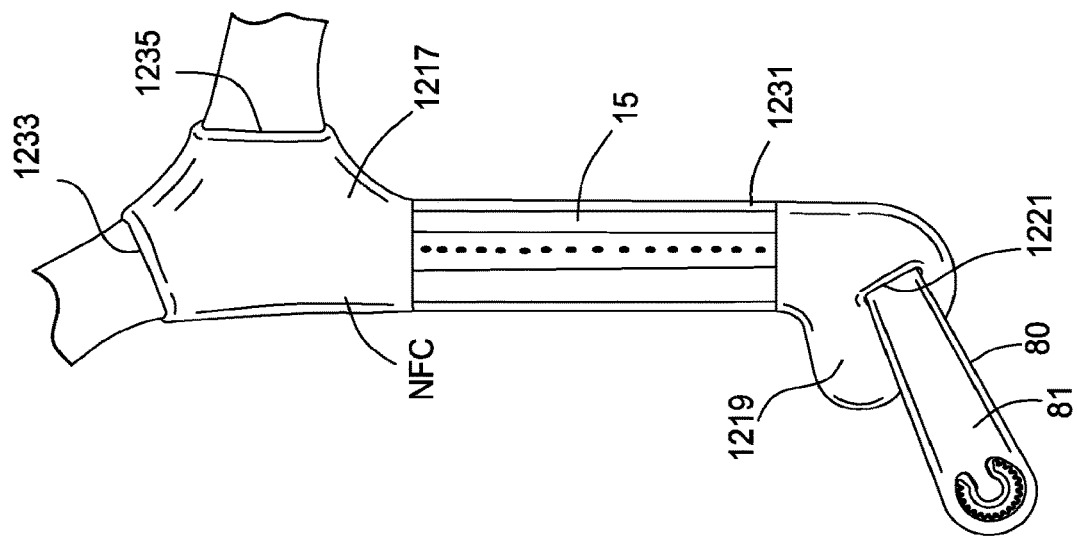
FIG. 37 is a side view of a front headgear strap and sleeve according to another embodiment of the present invention.

FIGS. 37 and 38 illustrate a front strap 15 provided within a sleeve or cover 1217. The non-face contacting side NFC of the sleeve includes a cavity or opening 1231 that allows the front strap to be assembled into the sleeve. As illustrated, one end portion of the sleeve includes a pocket 1219 to receive the end of the front strap and a slot 1221 to allow the frame engaging end 81 of the rigidizer 80 to extend therethrough. The opposing end portion of the sleeve includes openings 1233, 1235 to allow top and back strap portions to extend therethrough. In an embodiment, the face contacting side FC is constructed of fleece and the non-face contacting side NFC is constructed of Lycra or fleece. However, other suitable materials for the sleeve are possible.

Figure 39:
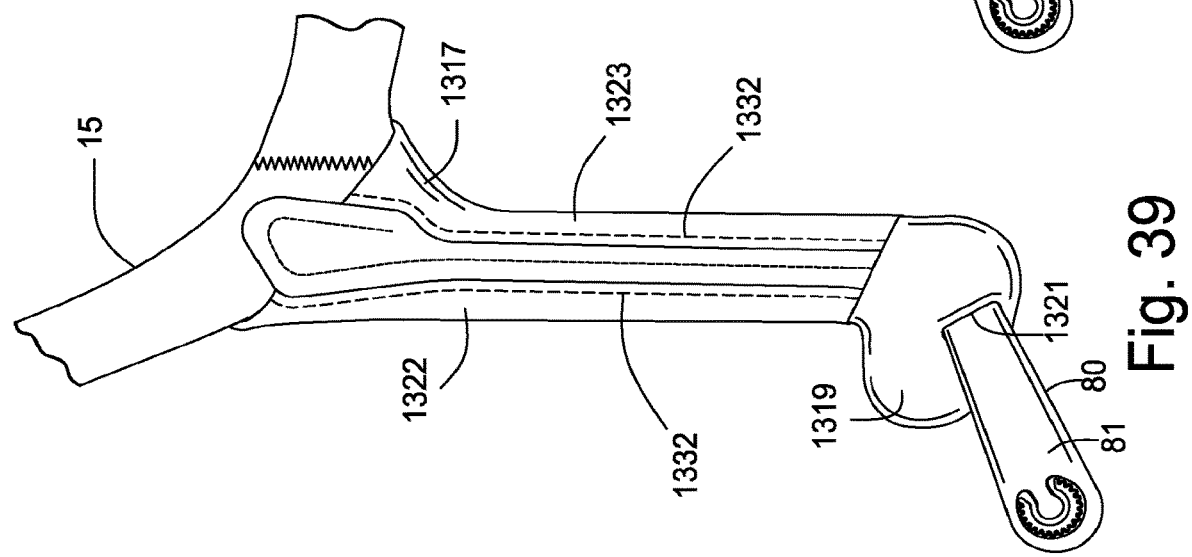
FIG. 39 is a side view of a front headgear strap and sleeve according to another embodiment of the present invention.

FIG. 39 illustrates a front strap 15 with a sleeve or cover 1317 wrapped around the front strap. As illustrated, side portions 1322, 1323 of the sleeve are secured to the front strap by stitching 1332. One end portion of the sleeve includes a pocket 1319 to receive the end of the front strap and a slot 1321 to allow the frame engaging end 81 of the rigidizer 80 to extend therethrough. Moreover, the pocket 1319 locates or aligns the sleeve with respect to the front strap to enable the sleeve to be wrapped around the front strap prior to stitching.

Figure 40:
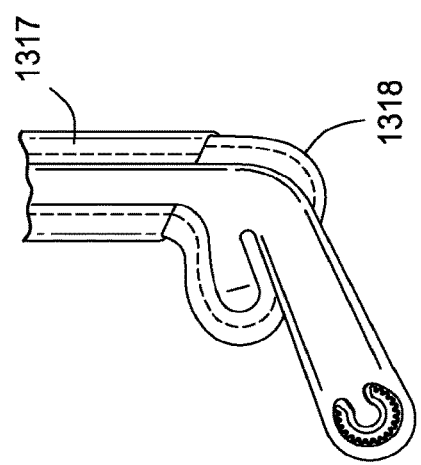
FIG. 40 is a partial side view showing an alternative separate sleeve portion for the sleeve of FIG. 39.

In an alternative embodiment, as shown in FIG. 40, the sleeve 1317 may have no pocket and a separate sleeve portion 1318 with a suitable profile may be provided to the end of the front strap and stitched in position.

Figure 41:
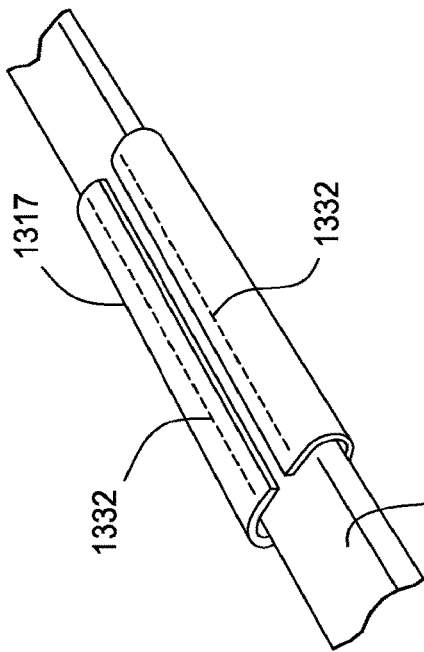
FIG. 41 is a schematic view of the front headgear strap and sleeve of FIG. 39.

As shown in FIG. 41, the sleeve 1317 (e.g., constructed of a fleece material) may be wrapped around the front strap 15 and stitched in position prior to the rigidizer 80 being assembled and stitched to the front strap. In such embodiment, the rigidizer may overlap one or more portions of the sleeve 1317.

Figure 42:
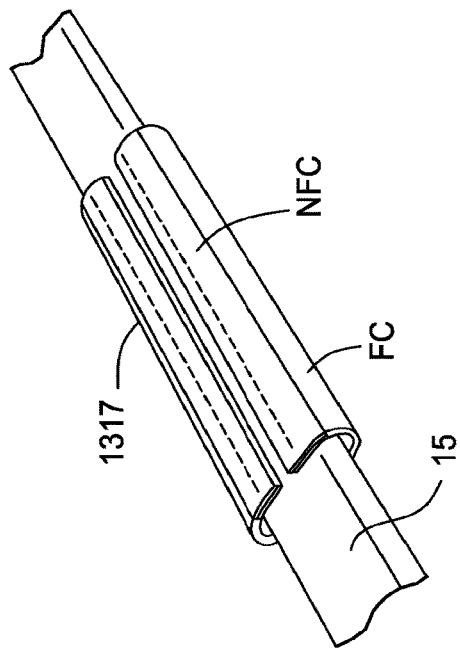
FIG. 42 is a schematic view of the front headgear strap and alternative sleeve of FIG. 39.

In another embodiment, as shown in FIG. 42, the sleeve 1317 may be constructed of two materials (e.g., face contacting side FC constructed of fleece and the non-face contacting side NFC constructed of Lycra) which may be sewn together prior to attaching the sleeve 1317 to the front strap 15.

Figure 44:
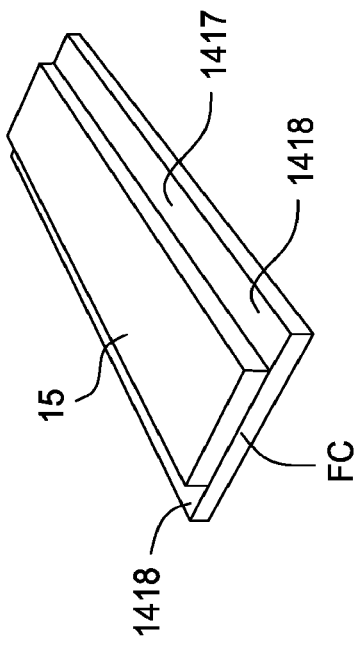
FIG. 44 is a schematic view of the front headgear strap and length of fleece material of FIG. 43.
Figure 43:
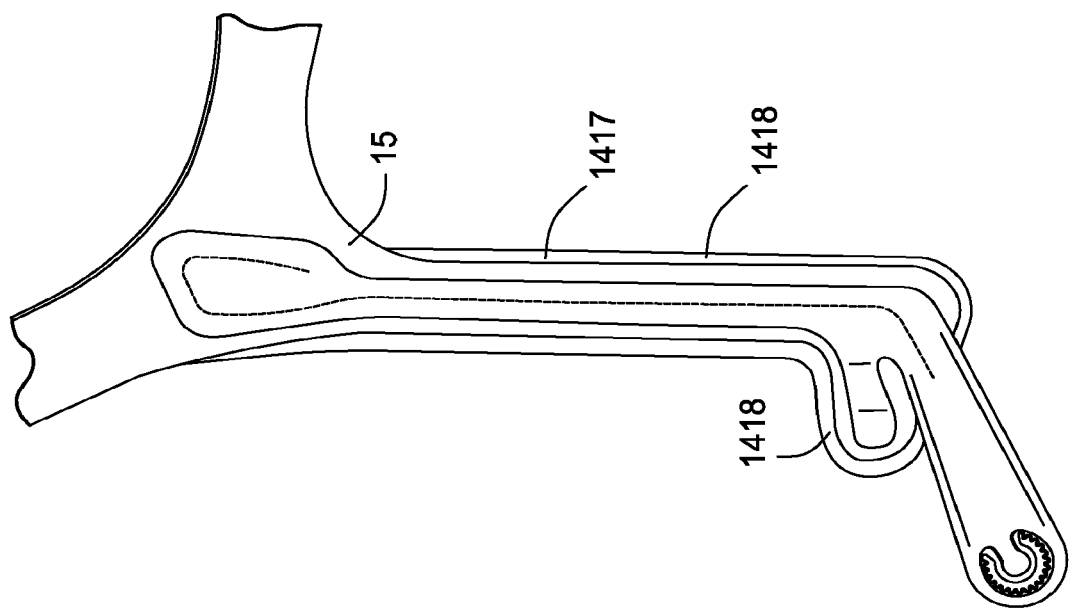
FIG. 43 is a side view of a front headgear strap and length of fleece material according to another embodiment of the present invention.

FIGS. 43 and 44 illustrate a front strap 15 and a length of fleece material 1417 provided to the face contacting side FC of the front strap. As illustrated, the front strap 15 is cut to a narrower profile and the fleece material 1417 is attached to the front strap (e.g., laminated or stitched) so that the fleece material 1417 include overhanging portions 1418 that overhang the front strap 15.

Figure 45:
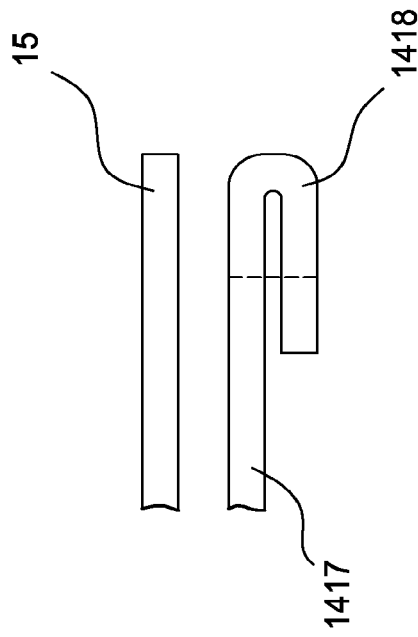
FIG. 45 is a schematic view showing an alternative arrangement for the length of fleece material of FIG. 43.

In an alternative embodiment, as shown in FIG. 45, the overhanging portion 1418 of the fleece 1417 may be folded over and stitched to itself to provide a soft, contoured edge.

FIGS. 46-48 illustrate a front strap 1515 with a foam core 1517 and a rigidizer 80 provided to the front strap 1515, e.g., via stitching. In an embodiment, as shown in FIG. 47, a face contacting side FC of the front strap is constructed of fleece and a non-face contacting side NFC of the front strap is constructed of Lycra, and the face contacting and non-face contacting sides FC, NFC define a sock that enclose a layer of foam material 1517 (e.g., memory foam or any varying density foam). To assemble, the face contacting and non-face contacting sides FC, NFC of the sock are sewn inside out and the foam material 1517 is provided within the sock as the sock is turned right-side out. The front strap 1515 is then sewn to the rigidizer 80.

In another embodiment, as shown in FIG. 48, the foam material 1517 may include dual density foam layers, e.g., higher density foam 1517(1) near the non-face contacting side NFC and a lower density foam 1517(2) near the face contacting side FC.

In each embodiment, the foam could also be a gel or other "spongy" material.

FIGS. 49 and 50 illustrate a front strap 15 with a sleeve 1617 wrapped around the front strap. In the illustrated embodiment, the face contacting side (not shown) of the sleeve is constructed of fleece and the non-face contacting side NFC of the sleeve is constructed of unbroken loop (UBL) material. As illustrated, the sleeve 1617 includes side portions 1622, 1623 adapted to be wrapped and fastened around the front strap portion of the front strap, e.g., by a Velcro® tab 1625 attachable to the UBL material, and a top portion 1624 adapted to be wrapped and fastened around the top strap portion of the front strap, e.g., by a Velcro® tab 1625 attachable to the UBL material. The end portion of the sleeve includes a pocket 1619 to receive the end of the front strap and a slot 1621 to allow the frame engaging end 81 of the rigidizer 80 to extend therethrough.

In an alternative embodiment, as shown in FIG. 51, the sleeve 1617 may be shorter, i.e., no top portion adapted to be wrapped and fastened around the top strap portion of the front strap.

FIG. 52 illustrates a front strap 15 provided within a simple sock or cover 1717. In this embodiment, the sock 1717 is simply pulled over the front strap. As illustrated, one end portion of the sleeve includes a pocket 1719 to receive the end of the front strap and a slot 1721 to allow the frame engaging end 81 of the rigidizer 80 to extend therethrough. In an embodiment, the face contacting side (not shown) is constructed of fleece and the non-face contacting side NFC is constructed of Lycra, mesh, or other high stretch fabric. In an alternative embodiment, the sock may be made of a more rigid material with extra tolerance around the front strap to ease assembly.

FIGS. 53 to 55 illustrate a front strap 1815 with a silicone strap portion 1817 adapted to engage the cheek region of the patient's face in use. As illustrated, the front strap 1815 includes top and back strap portions 1833, 1835 constructed of a fabric-type material (e.g., constructed of Breath-O-Prene™) and a front strap portion 1817 constructed of a silicone material. The top and back strap portions 1833, 1835 and the front strap portion 1817 are secured to one another by the rigidizer 80. For example, the upper end of the rigidizer is secured to the top and back strap portions by stitching 1825 and the lower end of the rigidizer is secured to the front strap portion by a snap-fit tab arrangement, e.g., silicone tabs 1827 provided to front strap portion 1817 that are adapted to interlock with respective openings 82 provided in the rigidizer 80 (see FIG. 55). However, the top and back strap portions and the front strap portion may be secured to one another in other suitable manners.

Figure 56:
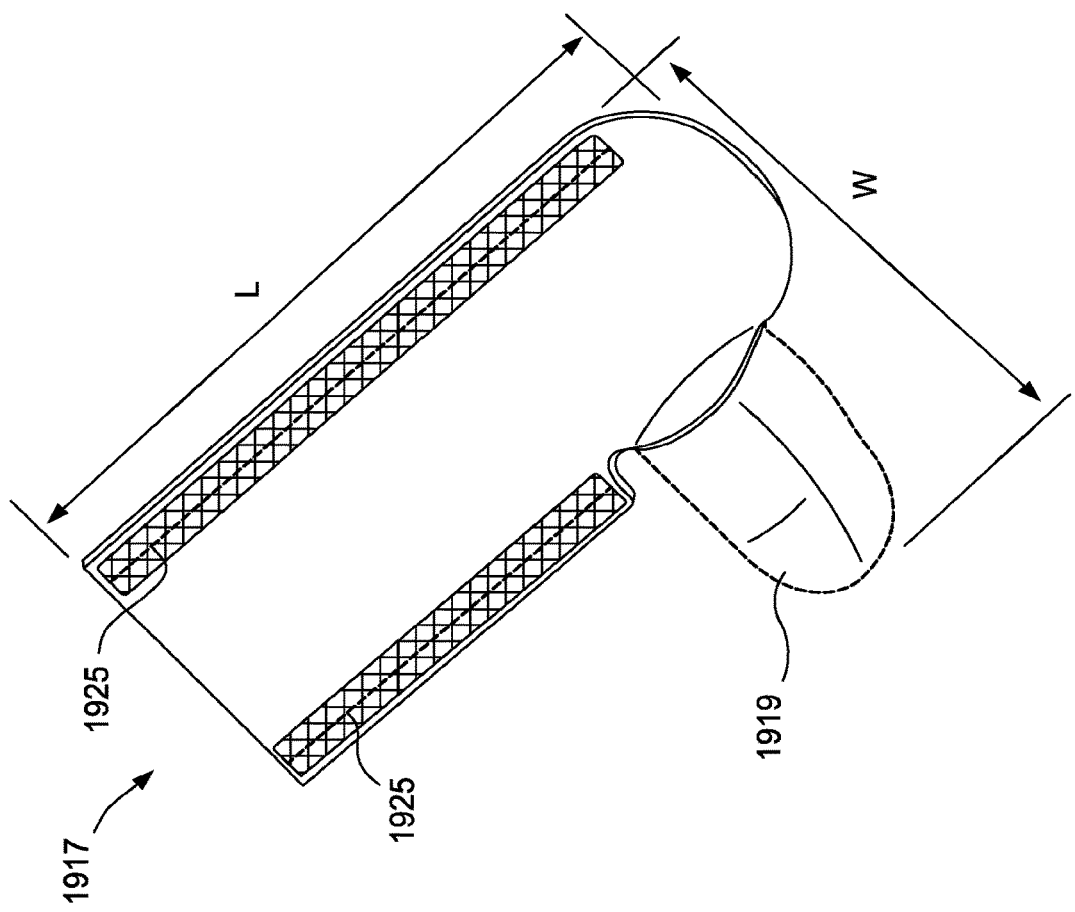
FIG. 56 is a plan view of a sock according to another embodiment of the present invention.
Figure 57:
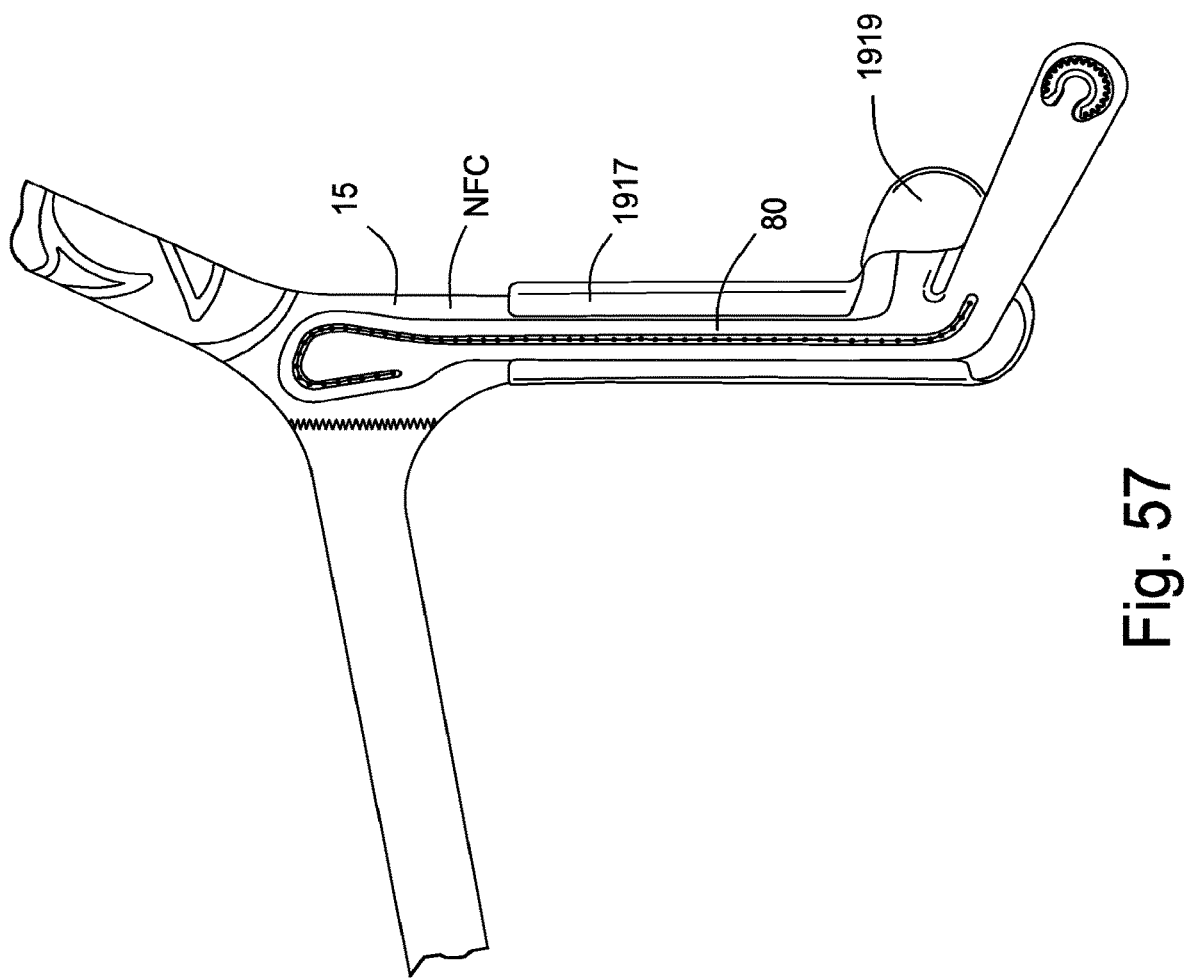
FIG. 57 is a side view of the sock of FIG. 56 attached to a front headgear strap.
Figure 58:
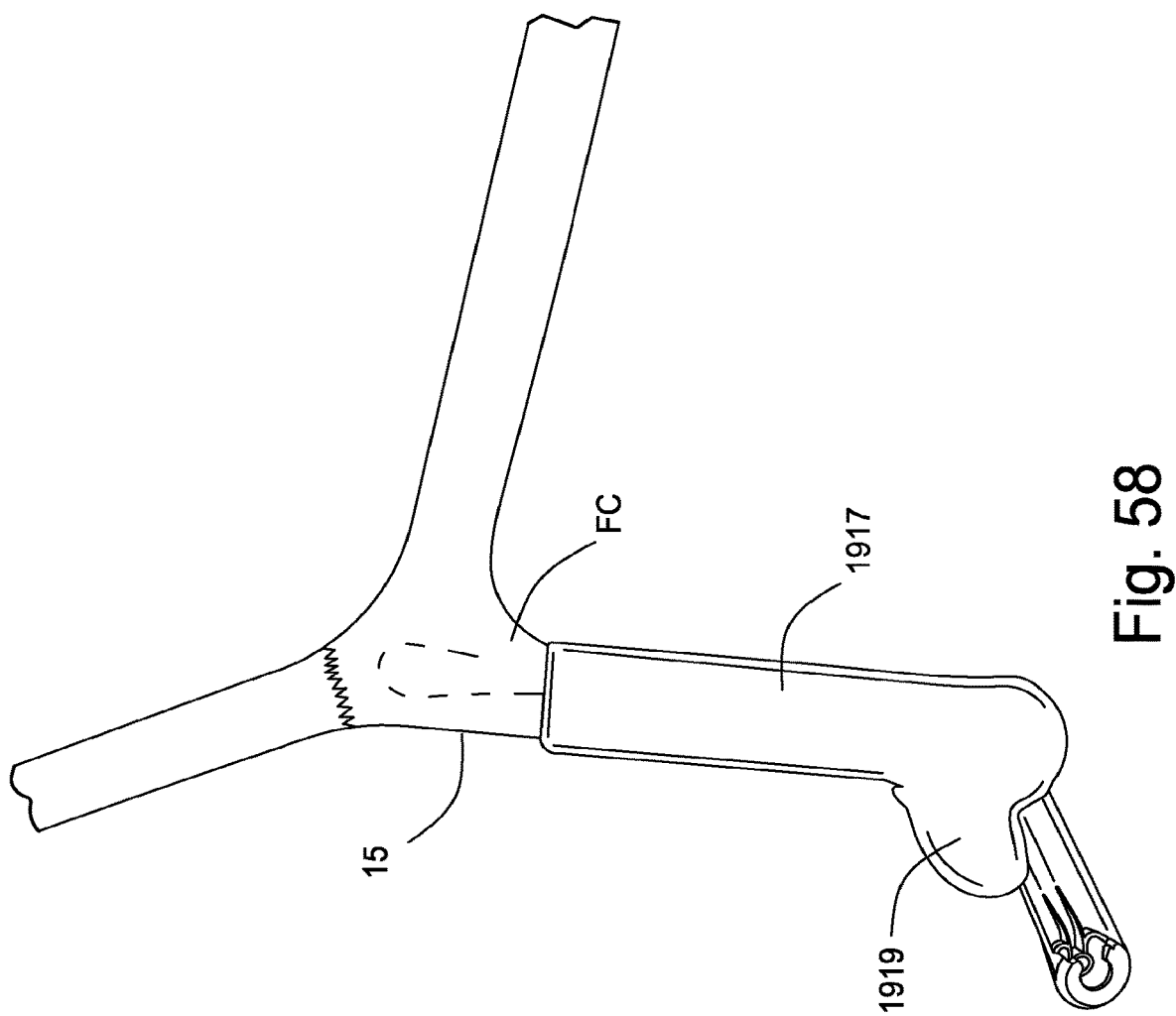
FIG. 58 is an opposing side view of the sock of FIG. 56 attached to a front headgear strap.
Figure 59:
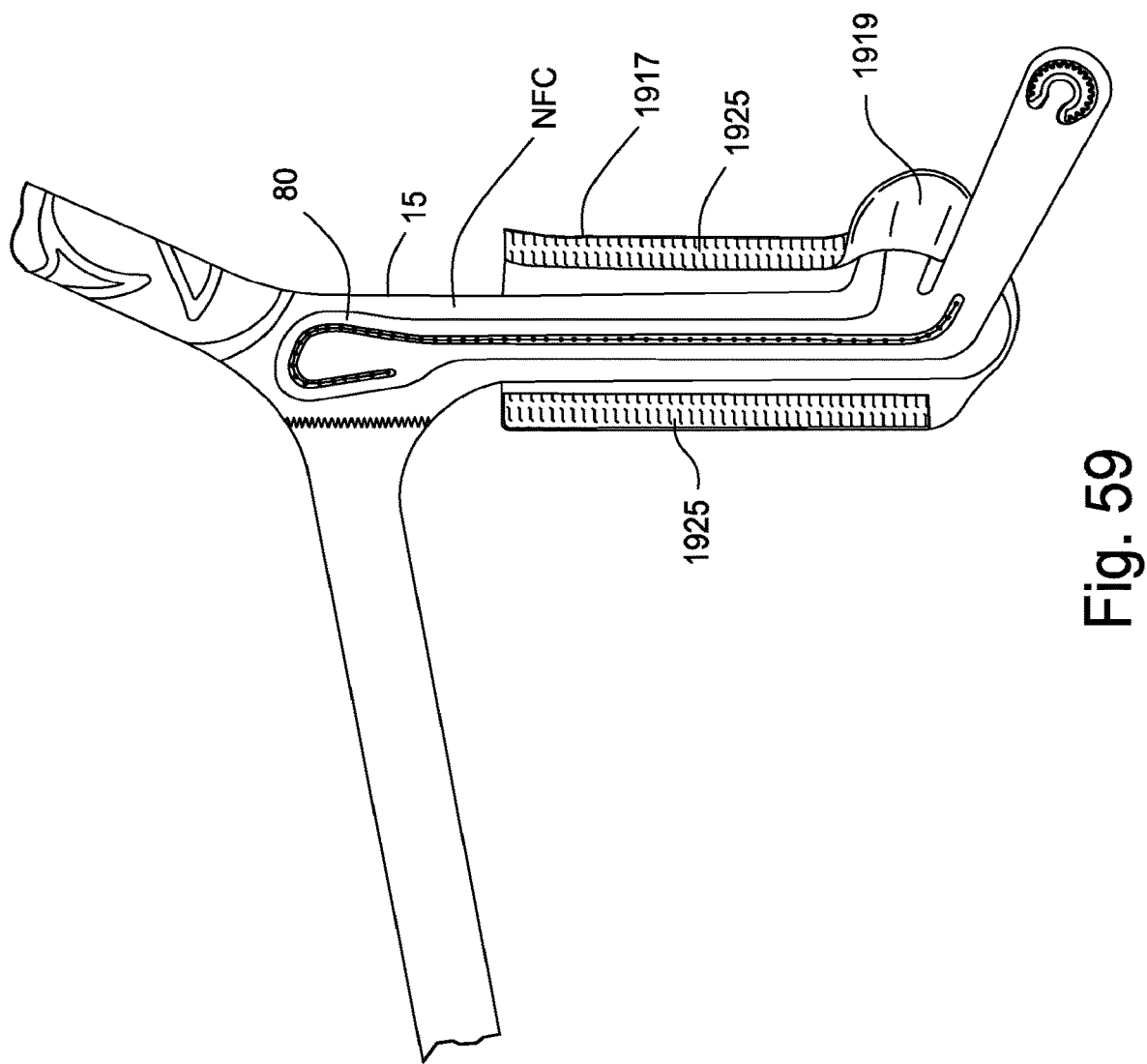
FIG. 59 is a side view of the sock of FIG. 56 assembled to a front headgear strap with the tabs of hook material detached.
Figure 60:
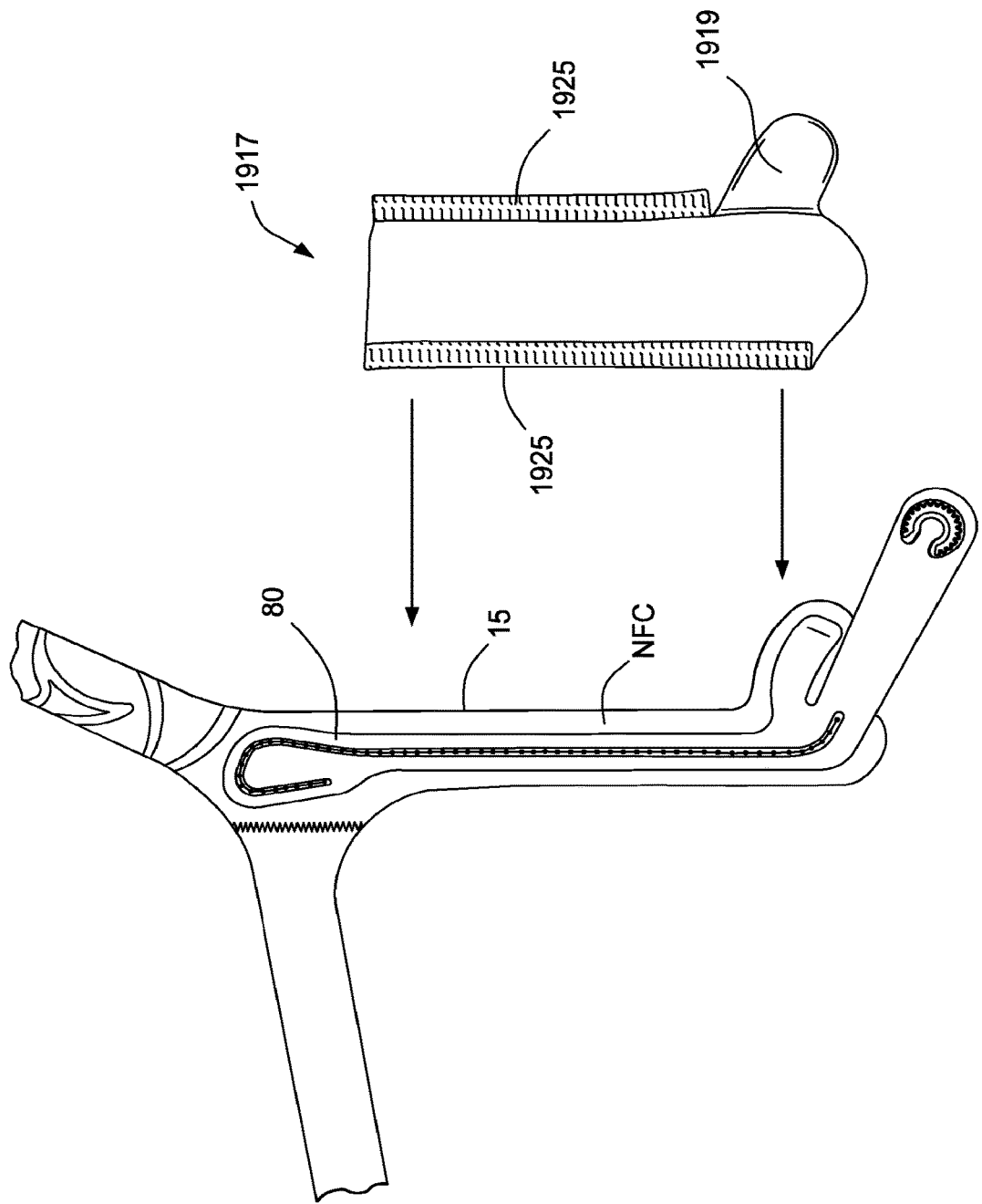
FIG. 60 is a side view of the sock of FIG. 56 disassembled from a front headgear strap.

FIGS. 56-60 illustrate a sock 1917 for a front strap 15 according to another embodiment of the present invention. In this embodiment, the sock 1917 is constructed of a fleece material and is structured to be wrapped around the face contacting side FC of the front strap so it contacts the patient's face in use. The sock 1917 includes a stitched fleece pocket 1919 which is structured to receive and surround the cheek support portion of the front strap in use. Each side of the sock includes an elongated tab of hook material 1925 (e.g., hook Velcro® attached via a straight stitch). In use, the cheek support portion of the front strap is slid into the pocket 1919 and then the sides of the sock 1917 are wrapped and fastened to the front strap by mating the tabs of hook material 1925 with the front strap 15. FIGS. 57 and 58 show the sock 1917 attached to the front strap 15, FIG. 59 shows the sock 1917 assembled to the front strap 15 with the tabs of hook material 1925 detached, and FIGS. 56 and 60 show the sock 1917 disassembled from the front strap 15.

The hook material 1925 may attach to the front strap 15 at the non-face contacting side NFC (as illustrated in FIG. 57), the face contacting side, along edges of the front strap, and/or along the width of the front strap. When the front strap is constructed of Breath-O-Prene™ material, the hook material may adjoin the lycra and/or foam portions of the material. In an alternative embodiment, the rigidizer 80 may be made from a loop material or may be retrofitted with a loop material so that the hook material on the sock may attach to the rigidizer rather than the material of the front strap.

In the embodiment, the length L of the sock may be about 50-250 mm, e.g., 70-150 mm (e.g., 110 mm), and the width W of the sock may be about 20-100 mm, e.g., 40-80 mm (e.g., 60 mm).

Figure 61:
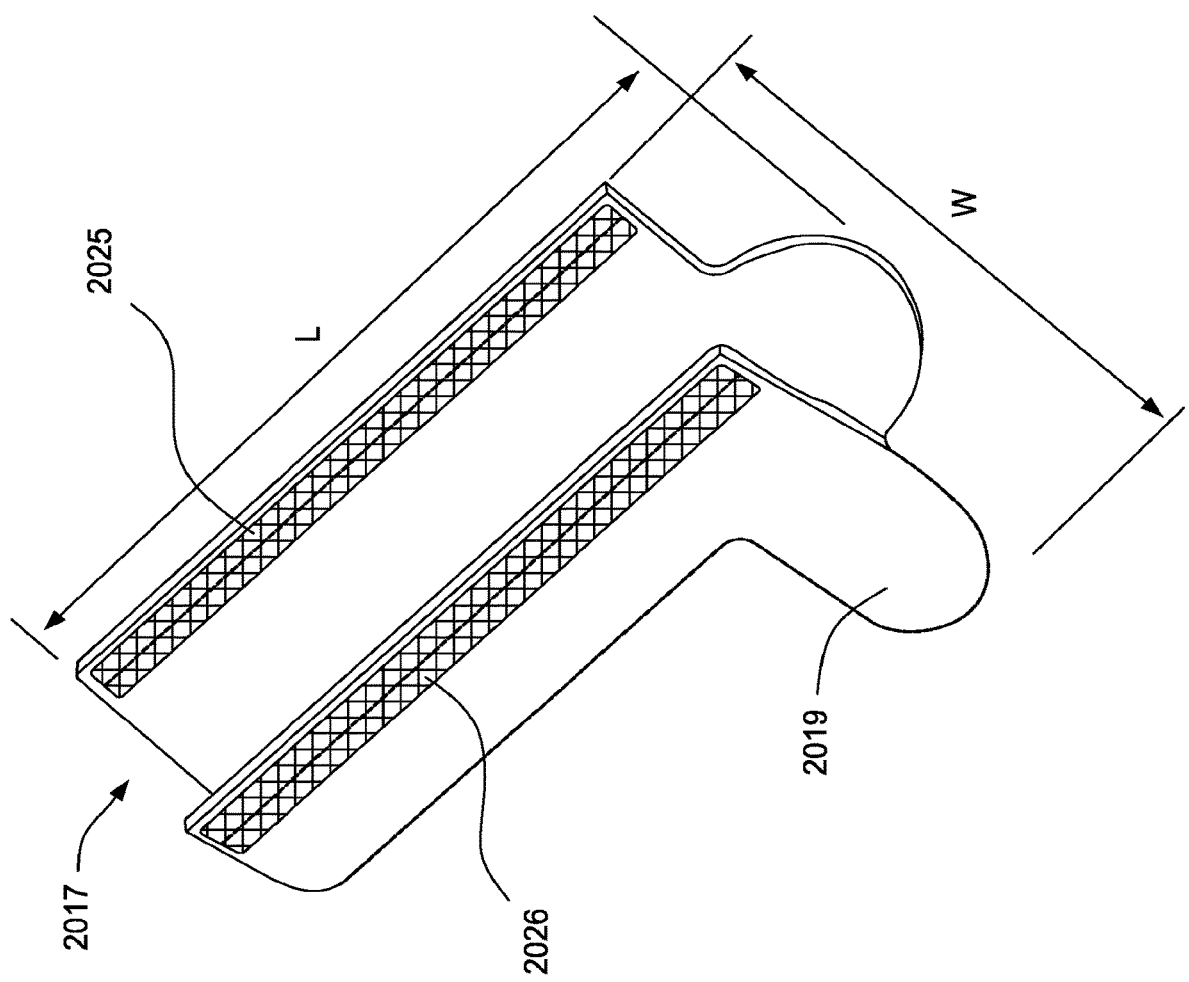
FIG. 61 is a plan view of a sock according to another embodiment of the present invention.
Figure 62:
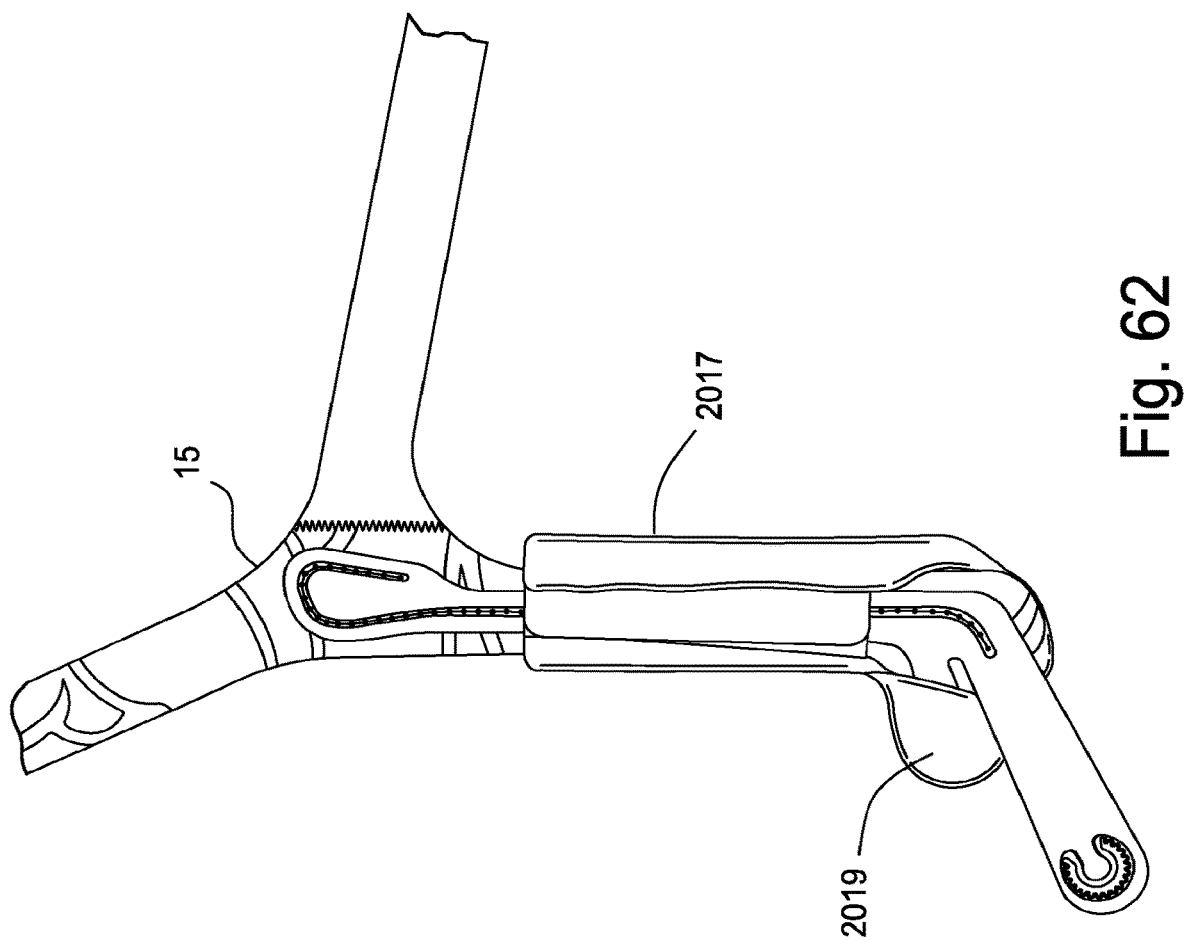
FIG. 62 is a side view of the sock of FIG. 61 attached to a front headgear strap.
Figure 63:
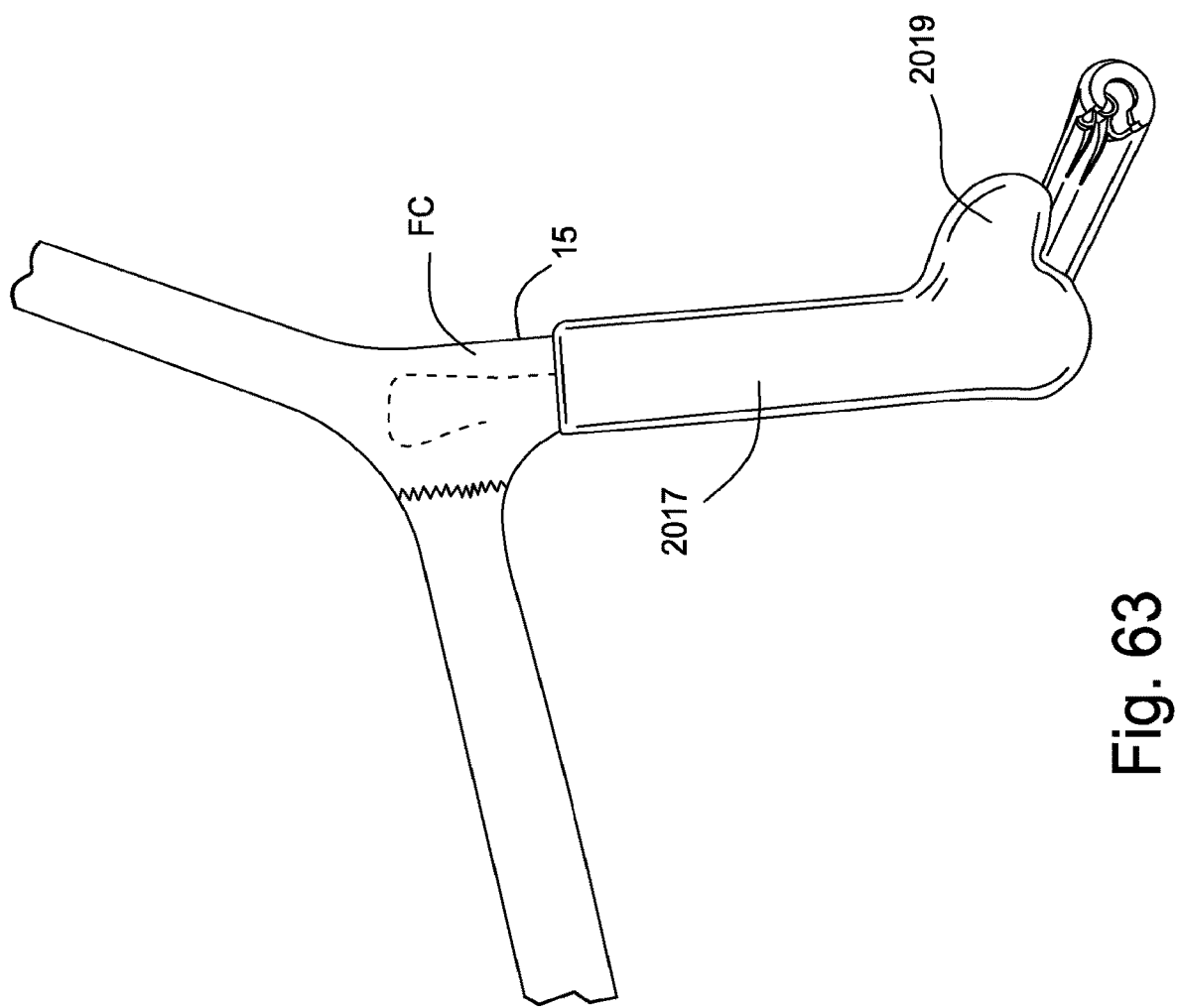
FIG. 63 is an opposing side view of the sock of FIG. 61 attached to a front headgear strap.
Figure 64:
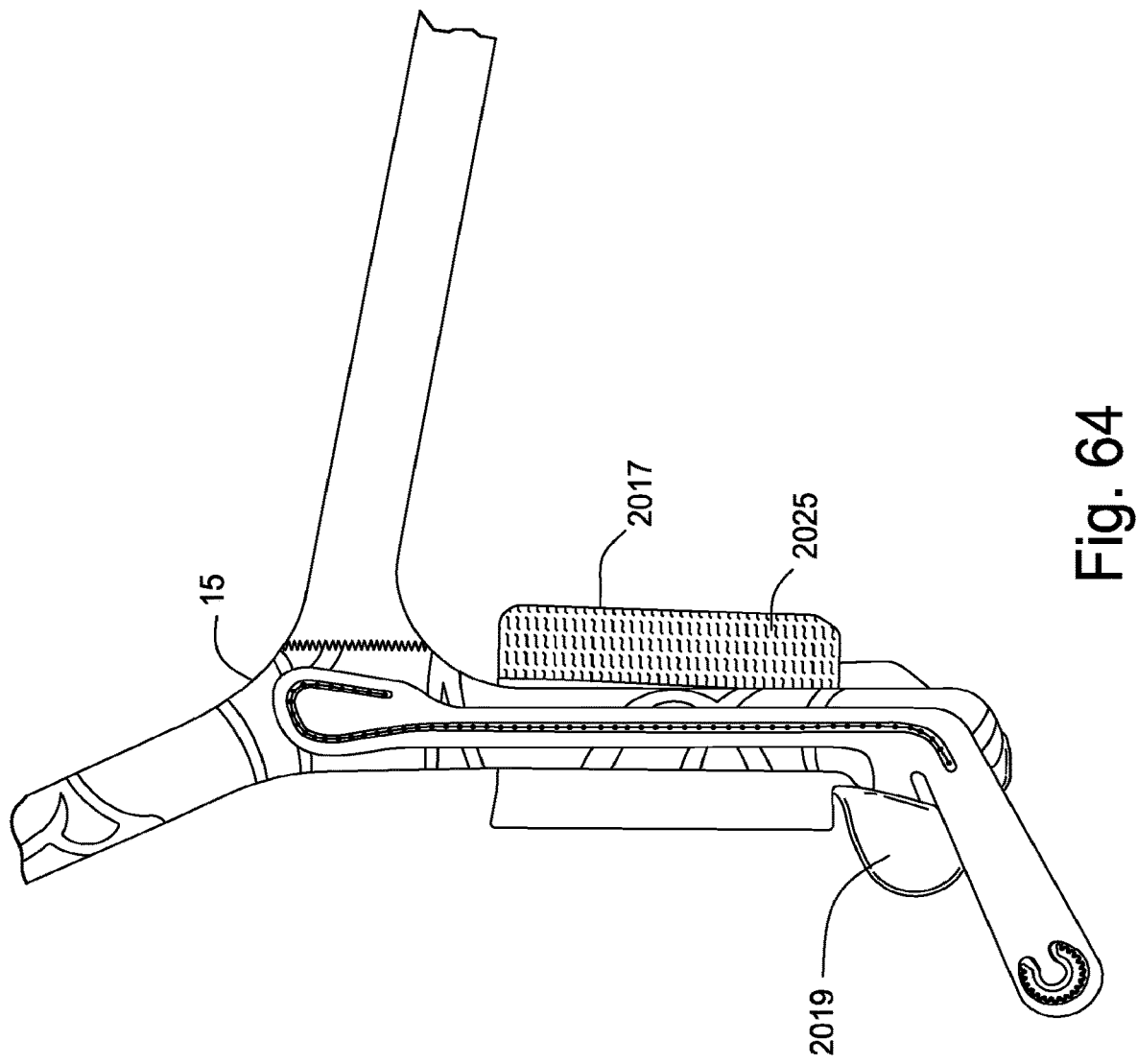
FIG. 64 is a side view of the sock of FIG. 61 assembled to a front headgear strap with the tabs unwrapped and detached.
Figure 65:
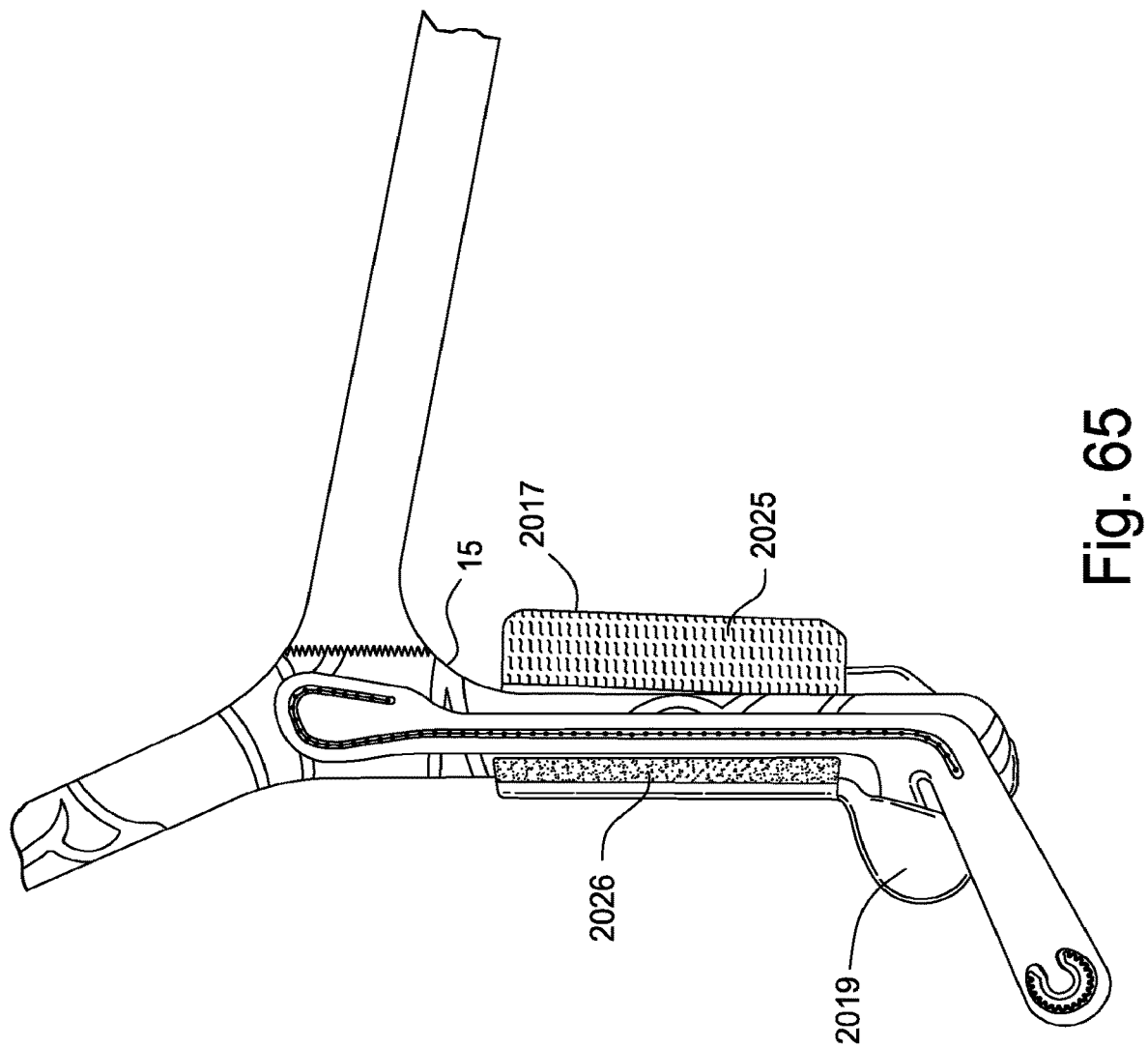
FIG. 65 is a side view of the sock of FIG. 61 assembled to a front headgear strap with the tabs detached but with the tab of loop material wrapped over the respective side of the front headgear strap.
Figure 66:
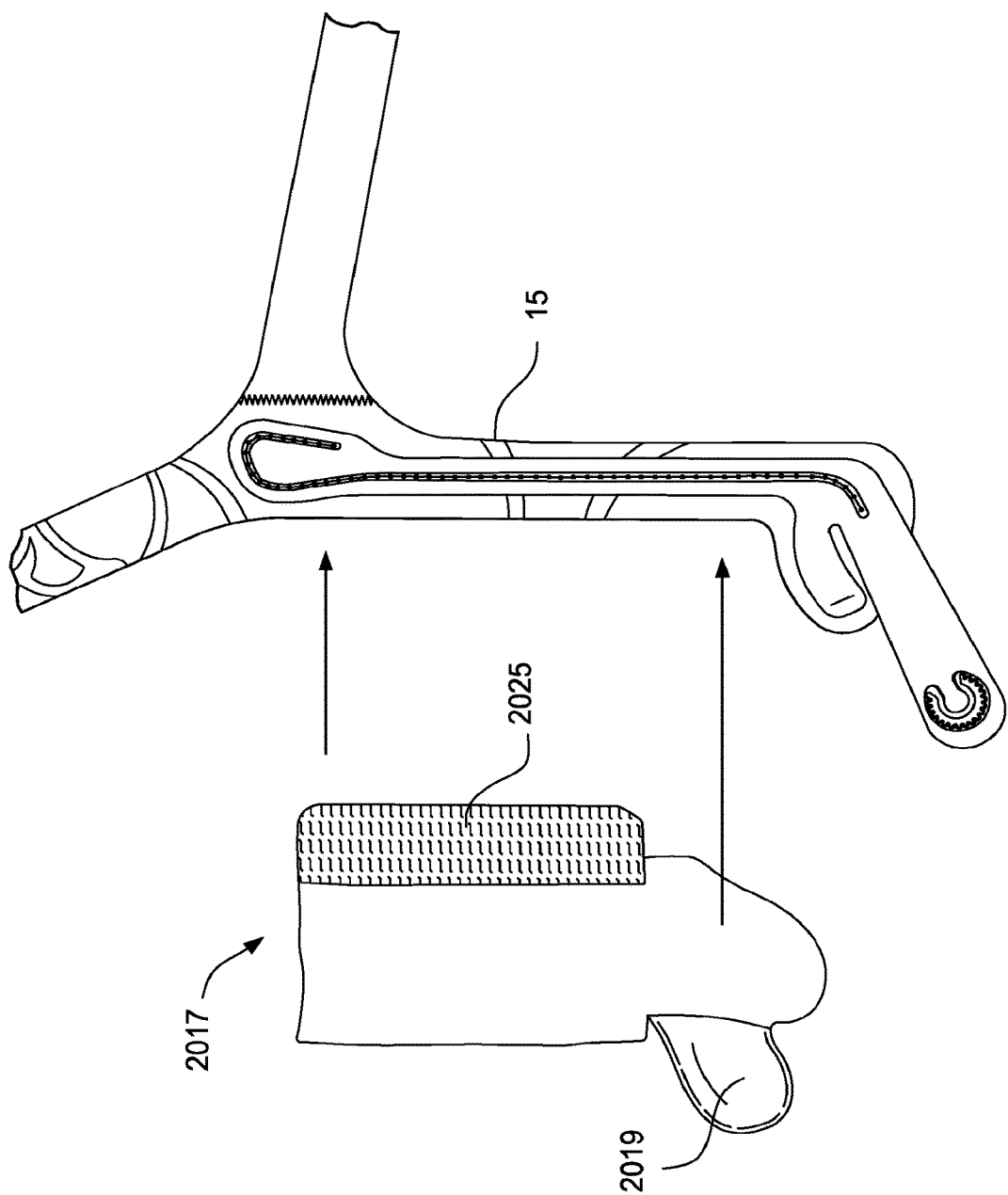
FIG. 66 is a side view of the sock of FIG. 61 disassembled from a front headgear strap.
Figure 70:
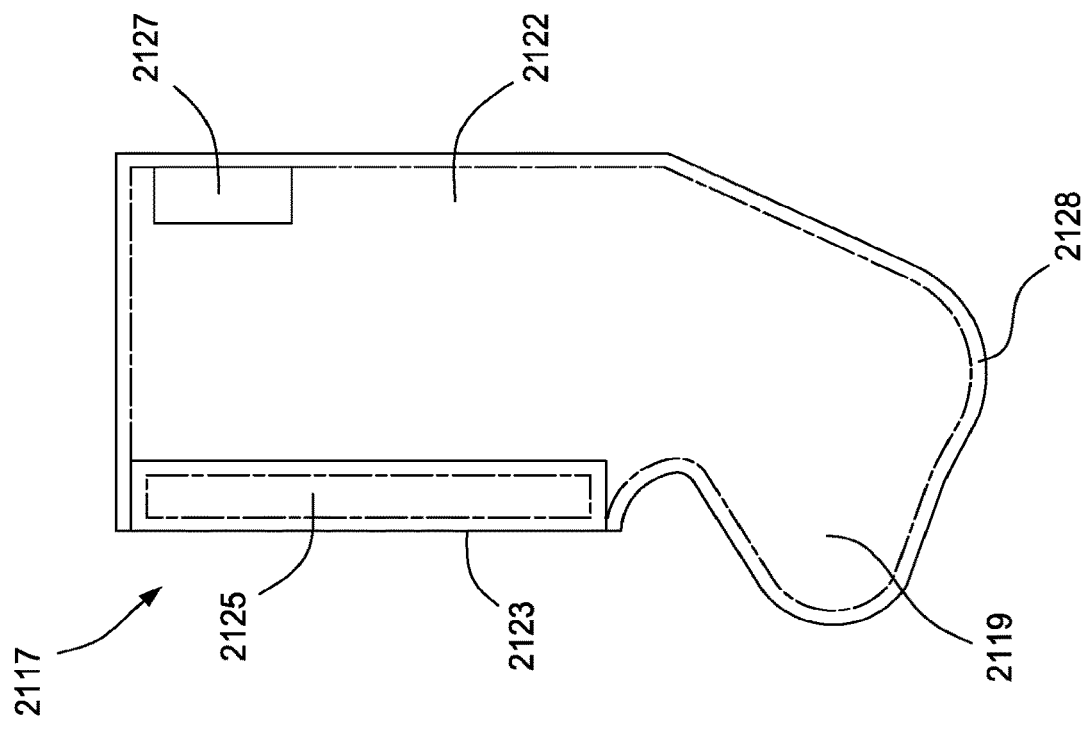
FIG. 70 is an opposing side view of the sock of FIG. 69.

FIGS. 61-66 illustrate a sock 2017 for a front strap 15 according to another embodiment of the present invention. In this embodiment, the sock 2017 is constructed of a fleece material and is structured to be wrapped around the face contacting side FC of the front strap so it contacts the patient's face in use. The sock 2017 includes a stitched fleece pocket 2019 which is structured to receive and surround the cheek support portion of the front strap in use. One side of the sock includes an elongated tab of hook material 2025 (e.g., hook Velcro® attached via a straight stitch), and the opposite side of the sock includes an elongated tab of loop material 2026 (e.g., loop Velcro® attached via a straight stitch). As illustrated, the tabs 2025, 2026 are positioned on opposing faces of the sock so that the tabs are oriented to engage one another when the sock is wrapped around the front strap. That is, the cheek support portion of the front strap is slid into the pocket 2019 and then the sides of the sock are wrapped over respective sides of the front strap and fastened to one another by mating the tab of hook material 2025 with the tab of loop material 2026. FIGS. 62 and 63 show the sock 2017 attached to the front strap 15, FIG. 64 shows the sock 2017 assembled to the front strap 15 with the tabs 2025, 2026 unwrapped and detached, FIG. 65 shows the sock 2017 assembled to the front strap 15 with the tabs 2025, 2026 detached but with the tab of loop material 2026 wrapped over the respective side of the front strap, and FIGS. 61 and 66 show the sock 2017 disassembled from the front strap 15.

In an embodiment, the length L of the sock may be about 50-250 mm, e.g., 70-150 mm (e.g., 110 mm), and the width W of the sock may be about 20-110 mm, e.g., 40-90 mm (e.g., 70 mm).

FIGS. 67-74 illustrate a sock 2117 for a front strap 15 according to another embodiment of the present invention. The sock 2117 is constructed of a single-sided fleece material and is structured to be wrapped around the face contacting side of the front strap 15 so that the fleece side of the sock 2117 contacts the patient's face in use. In this embodiment, the curvature of the sock 2117 is configured so that the front strap 15 is substantially covered without being too obtrusive with the patient's face in use. In addition, the sock 2117 allows the frame engaging end 81 of the rigidizer 80 to be exposed or uncovered so that branding on the frame engaging end 81 can be visible in use.

Figure 74:
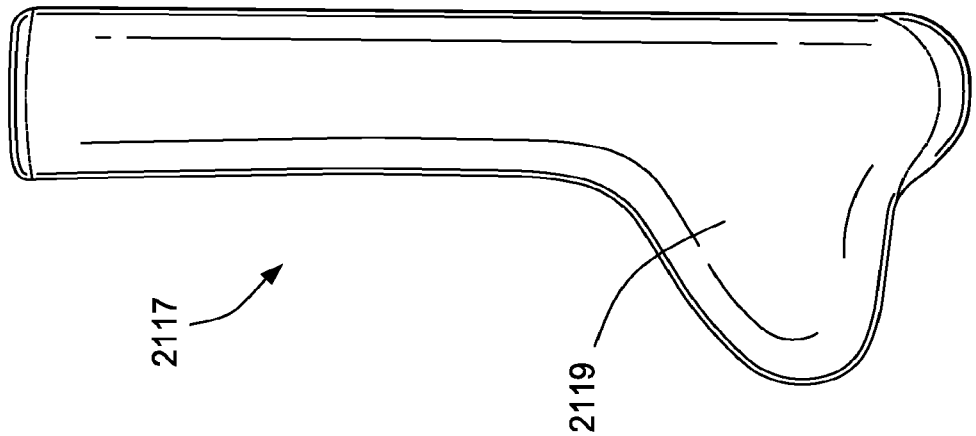
FIG. 74 is an opposing side view of the sock of FIG. 73.
Figure 73:
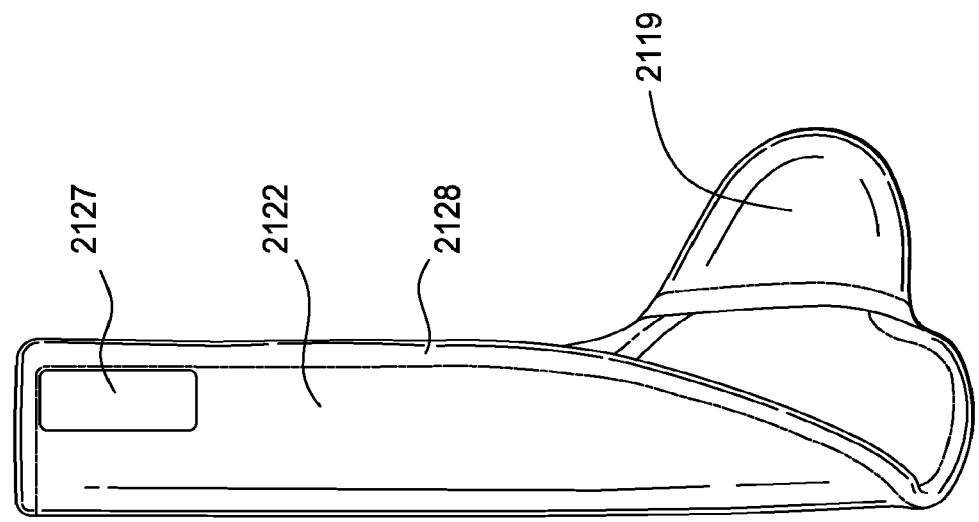
FIG. 73 is a side view of the sock of FIG. 67 disassembled from the front headgear strap with the tabs of hook material attached.

The sock 2117 includes a stitched fleece pocket 2119 which is structured to receive and surround the cheek support portion of the front strap 15 in use. One side of the sock 2117 includes an elongated tab of hook material 2125 (e.g., hook Velcro® attached via stitching), and the opposite side of the sock 2117 includes an elongated tab of loop material 2126 (e.g., loop Velcro® attached via stitching). As illustrated, the tabs 2125, 2126 are positioned on opposing faces of the sock 2117 so that the tabs are oriented to engage one another when the sock is wrapped around the front strap 15. That is, the cheek support portion of the front strap 15 is slid into the pocket 2119 and then the sides 2122, 2123 of the sock 2117 are wrapped over respective sides of the front strap 15 and fastened to one another by mating the tab of hook material 2125 with the tab of loop material 2126. FIGS. 67-68 show the sock 2117 attached to the front strap 15, FIGS. 69-72 show right hand side and left hand side versions of the sock 2117 disassembled from the front strap 15 with the tabs 2125, 2126 unwrapped and detached (in contrast to the right hand side, the left hand side may not include a company tag or label 2127), and FIGS. 73-74 show the sock 2117 disassembled from the front strap 15 with the tabs 2125, 2126 wrapped and attached.

As best shown in FIG. 68, the lower end of the front strap 15 is at least partially uncovered or visible when the sock 2117 is assembled onto the front strap 15. This allows the user to visually inspect and confirm that the sock 2117 completely covers the front strap 15. In an embodiment, it is preferable that lower edges 2118 of the sock 2117 extend about 3-5 mm from lower edges 15.5 of the front strap 15 (e.g., as shown in the circled area of FIG. 68).

In the illustrated embodiment, the hook and loop materials 2125, 2126 do not overhang the edges of the fleece material (e.g., see FIGS. 69-72). Also, all four corners of the hook and loop materials 2125, 2126 may be chamfered to remove sharp edges. In addition, the perimeter of the sock 2117 includes an overlock stitch 2128 so as to provide a soft, rolled edge. This arrangement reduces sharp edges provided by the sock to enhance comfort of the sock in use.

Figure 69:
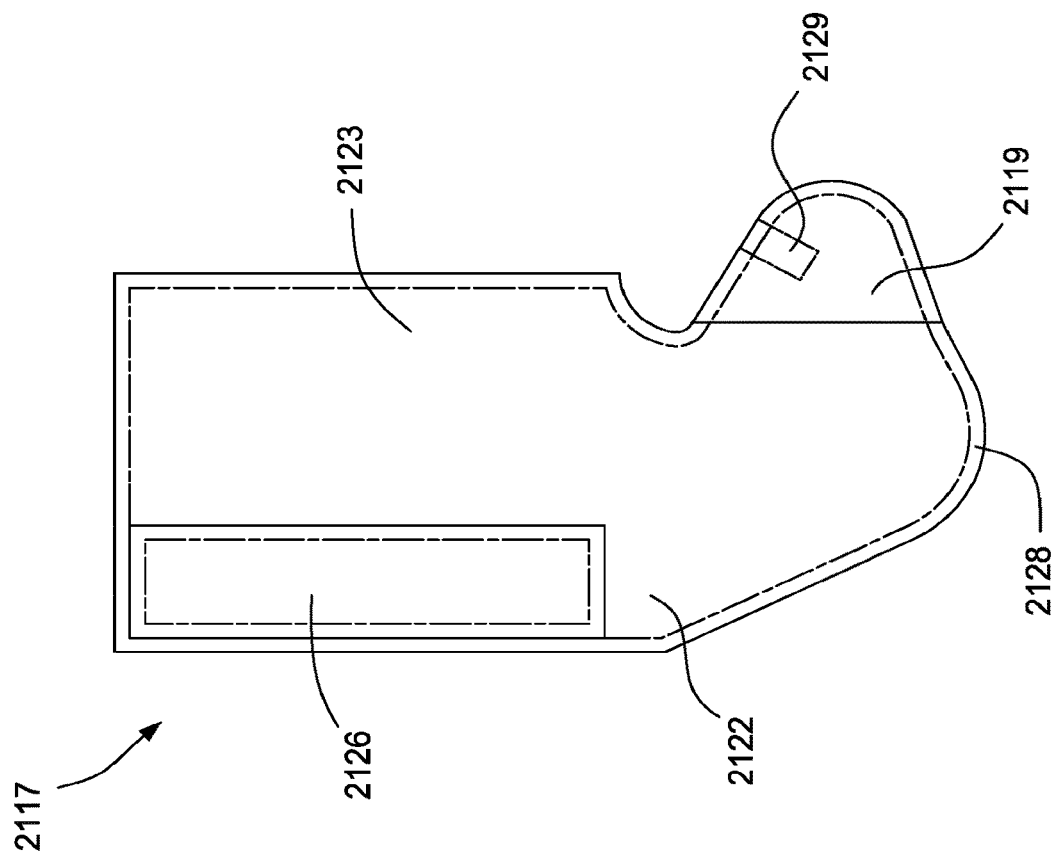
FIG. 69 is a side view of the sock of FIG. 67 disassembled from the front headgear strap with the tabs of hook material detached.
Figure 72:
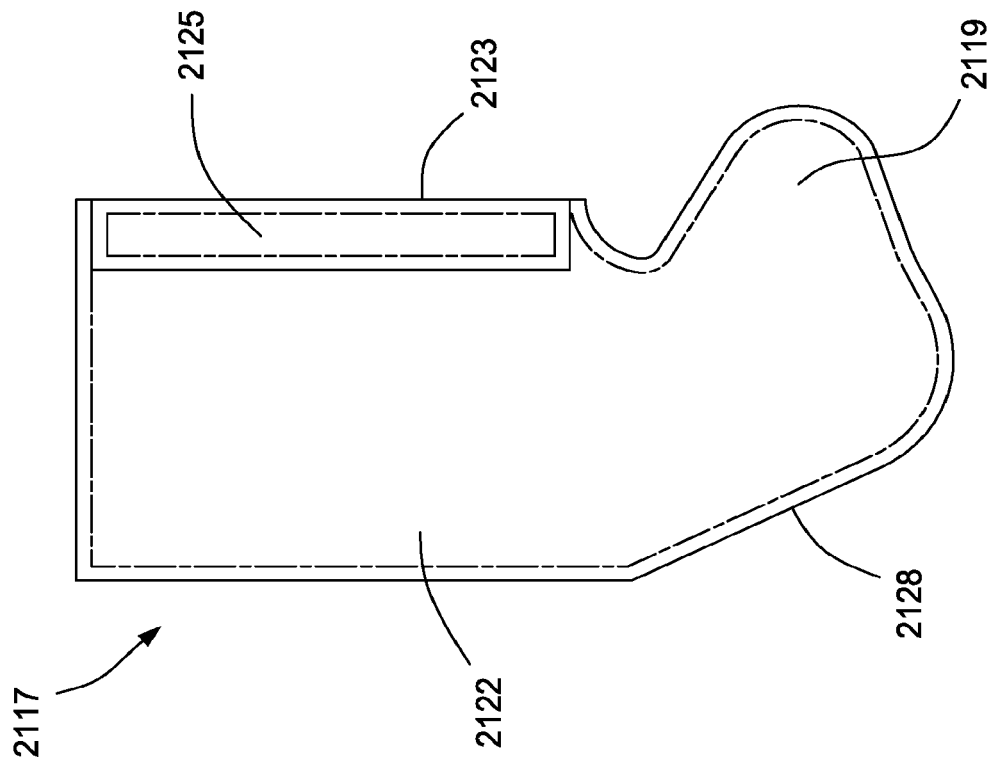
FIG. 72 is an opposing side view of the sock of FIG. 71.
Figure 71:
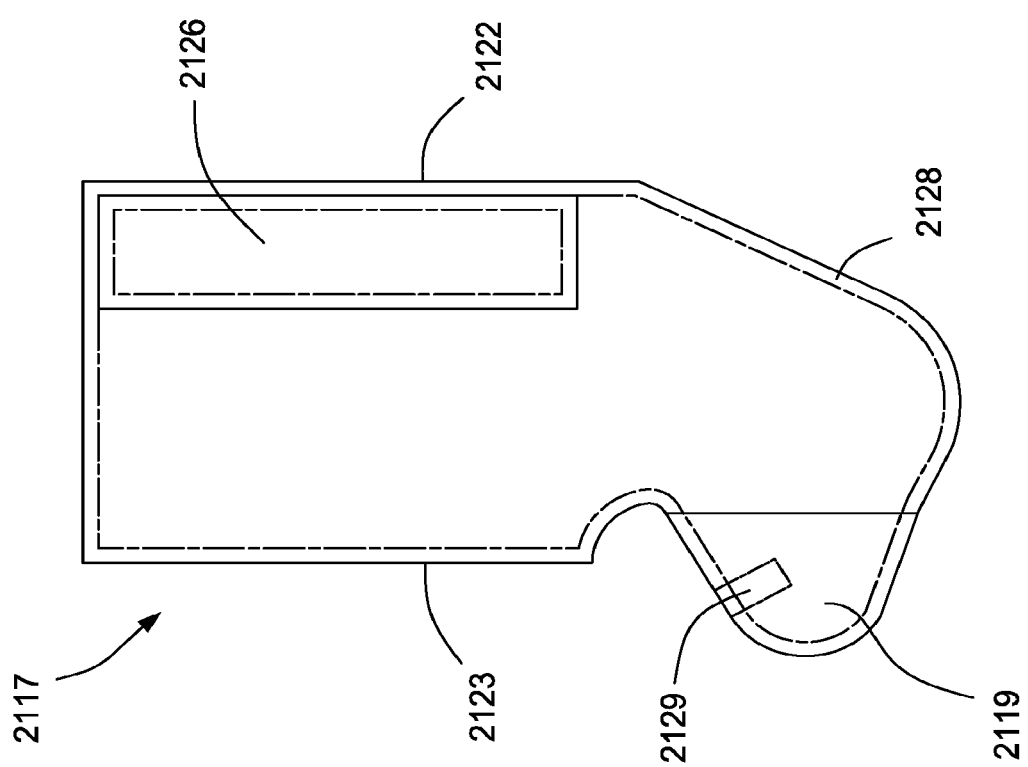
FIG. 71 is a side view of a left hand version of the sock of FIG. 67 disassembled from the front headgear strap with the tabs of hook material detached.

In an embodiment, as shown in FIGS. 69 and 71, a country of origin tag 2129 (which is optional) may be concealed inside the pocket or sleeve 2119. Also, a company tag or label 2127 may be provided on the same side as the hook material 2125 (e.g., in the upper right hand corner) so that the tag or label 2127 is visible when the sock is wrapped around the front strap 15 (i.e., tag or label faces outwardly as sown in FIG. 67). The tag or label 2127 may be stitched into position (e.g., sewn under the overlock stitch 2128).

2.5 Foam Padding and Straps

Figure 75:
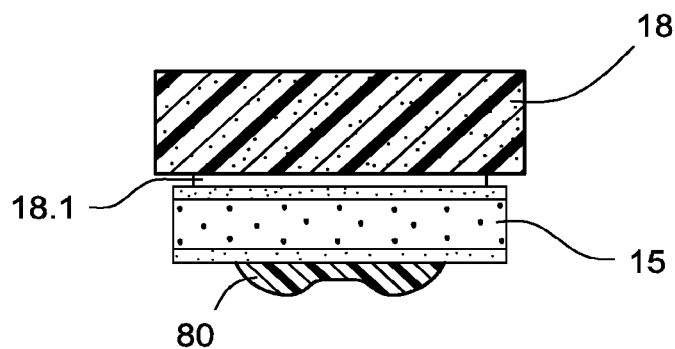
FIG. 75 is a cross-sectional view of a front headgear strap and foam pad according to an embodiment of the present invention.

FIG. 75 shows a foam pad 18 (thick soft foam, visco elastic or similar) provided to the patient contacting surface of the front strap 15 (e.g., constructed of Breath-O-Prene™). The foam pad may be secured to the front strap 15 by double sided tape 18.1 or any other suitable means. In an embodiment, the rigidiser 80 may be secured to the front strap 15 by stitching or other suitable means.

Figure 76:
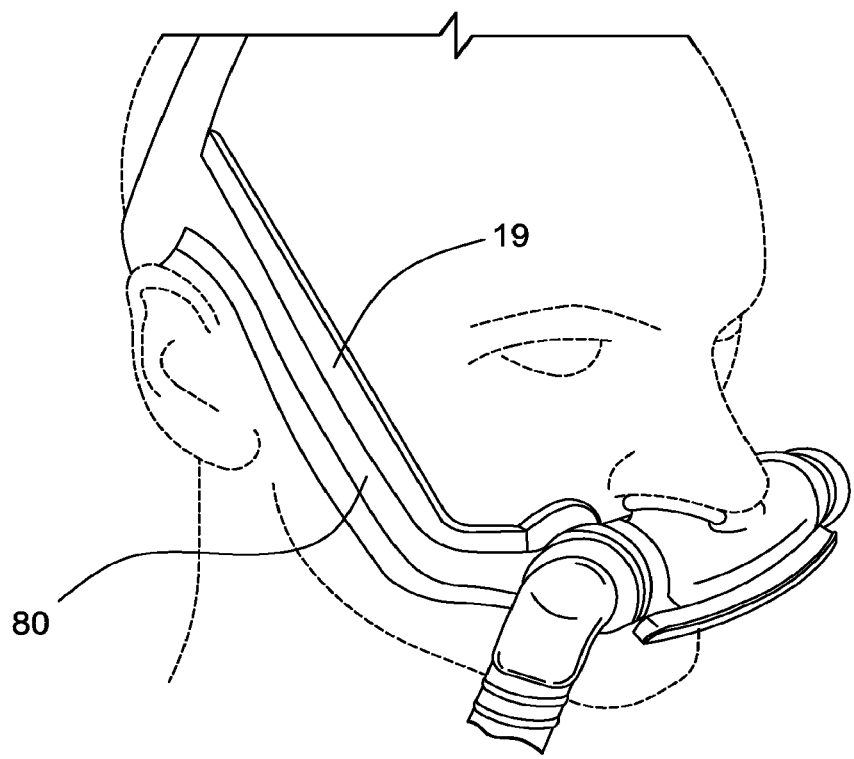
FIG. 76 is a perspective view of headgear with foam surrounding a rigidiser according to an embodiment of the present invention.
Figure 77:
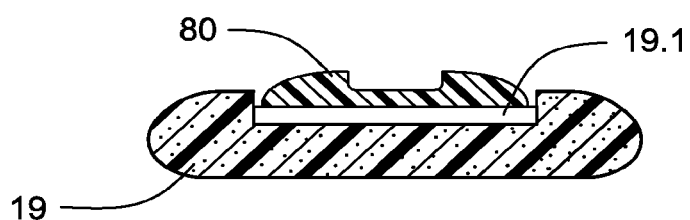
FIG. 77 is a cross-sectional view of the foam and rigidizer shown in FIG. 76.

FIGS. 76 and 77 show a thermoformed or molded foam 19 that replaces the front headgear straps and surrounds the yoke or rigidiser 80. The yoke or rigidiser 80 may be secured to the thermoformed or molded foam 19 by double sided tape 19.1 or any other reasonable means.

2.6 Silicone Padding and Straps

Figure 81:
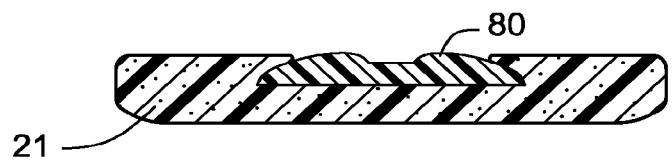
FIG. 81 is a cross-sectional view showing a rigidiser molded into a silicone cheek pad according to an embodiment of the present invention.
Figure 82:
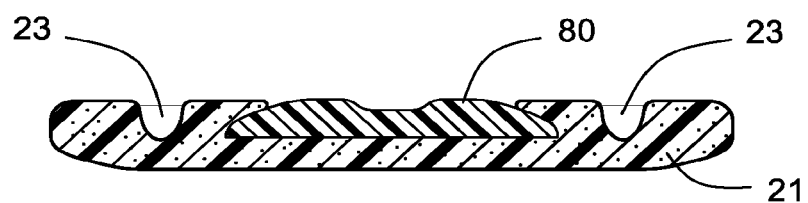
FIG. 82 is a cross-sectional view showing a silicone cheek pad with channels or ridges according to an embodiment of the present invention.

Silicone cheek pads may be provided to the front straps of the headgear to provide more comfort to the patient. For example, FIGS. 78-80 illustrate a silicone cheek pad 21 provided to a rigidiser 80. FIGS. 78 and 80 show the cheek pad 21 with a width w of about 19 mm and FIG. 79 shows the cheek pad 21 with a width w of about 15 mm. In an embodiment, the rigidiser 80 may be molded into the silicone cheek pad 21 (or vice versa) as shown in FIG. 81. For example, the molded silicone cheek pad may have a hardness of about 20-60 shore A. In another example, the cheek pad may be an overmolded TPE. In an embodiment, the rigidiser 80 may also be adhered to the cheek pad 21, e.g., by double sided tape. As shown in FIGS. 80 and 82, channels or ridges 23 may be provided to the silicone cheek pad 21 to allow the silicone to flex and contour to the patient's face in use.

Figure 83:
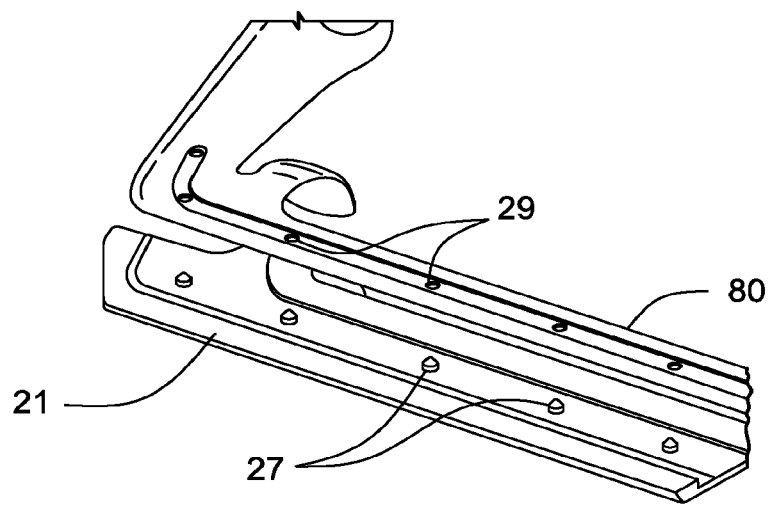
FIG. 83 is a perspective view showing a silicone cheek pad retrofit to a rigidiser according to an embodiment of the present invention.
Figure 84:
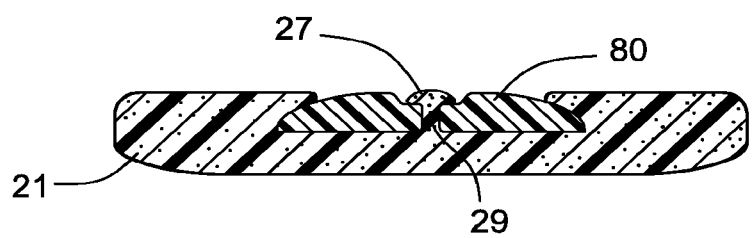
FIG. 84 is a cross-sectional view showing the silicone cheek pad and rigidiser shown in FIG. 83.
Figure 85:
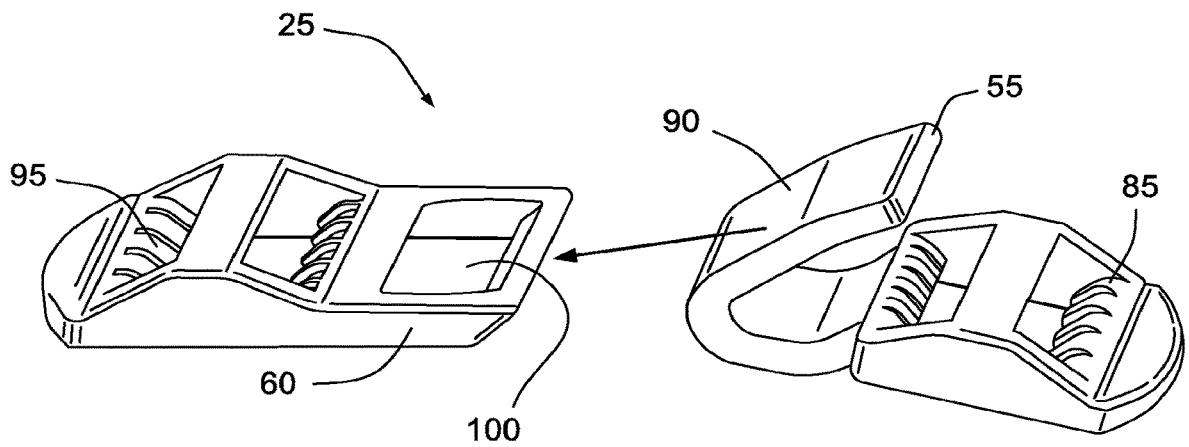
FIG. 85 shows a perspective view of a clasp of the headgear of FIG. 1 in a disconnected state.
Figure 86:
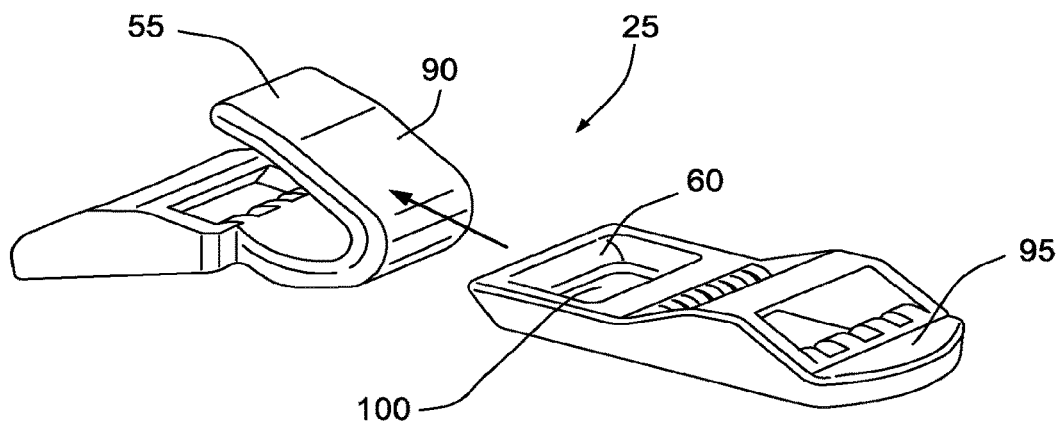
FIG. 86 shows a further perspective view of a clasp of the headgear of FIG. 1 in a disconnected state.
Figure 87:
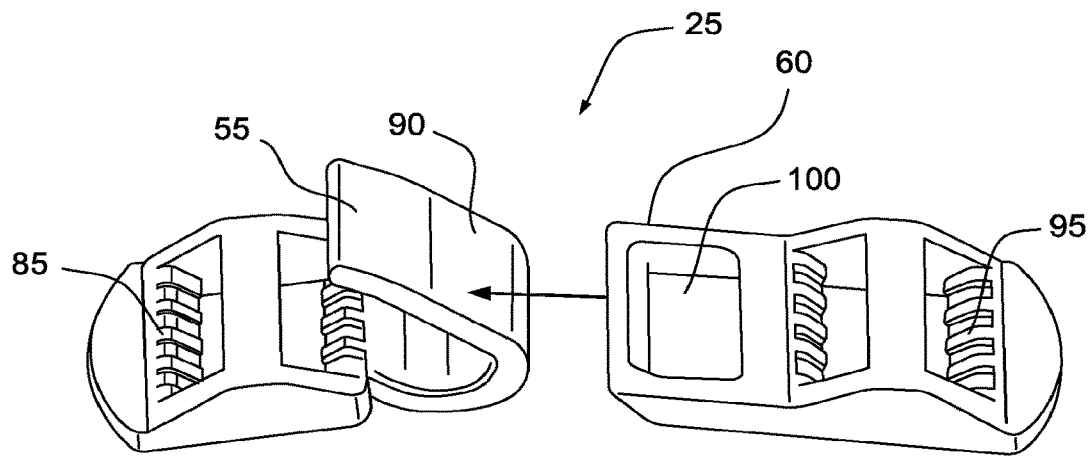
FIG. 87 shows a further perspective view of a clasp of the headgear of FIG. 1 in a disconnected state.
Figure 88:
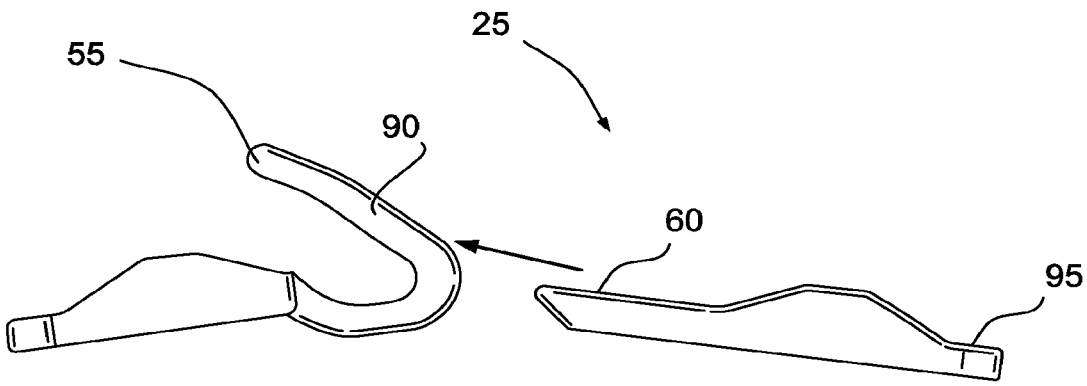
FIG. 88 shows a side view of a clasp of the headgear of FIG. 1 in a disconnected state.
Figure 89:
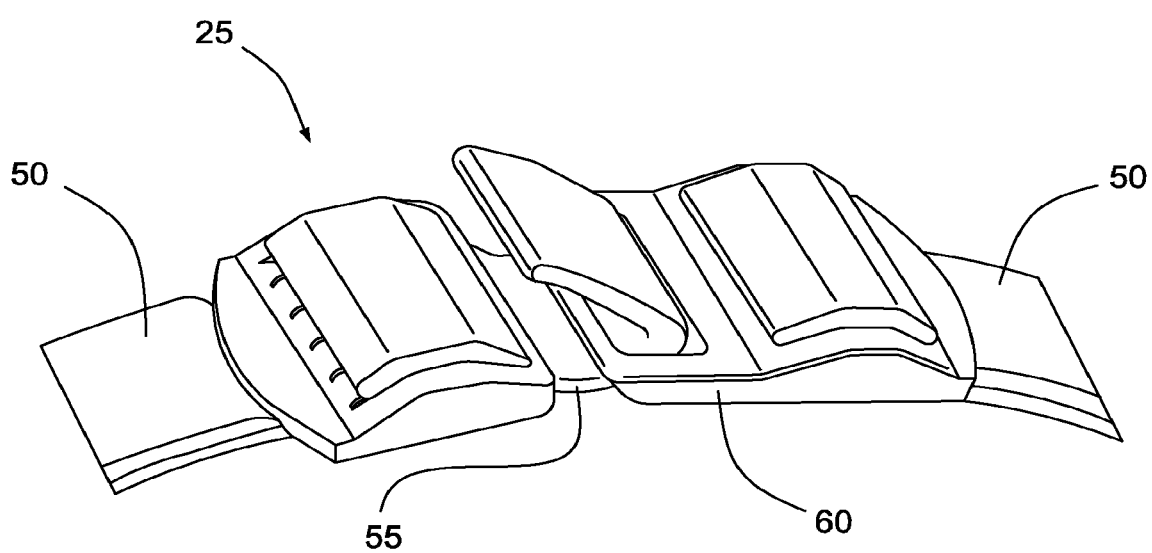
FIG. 89 shows a perspective view of a clasp of the headgear of FIG. 1 in a connected state.
Figure 90:
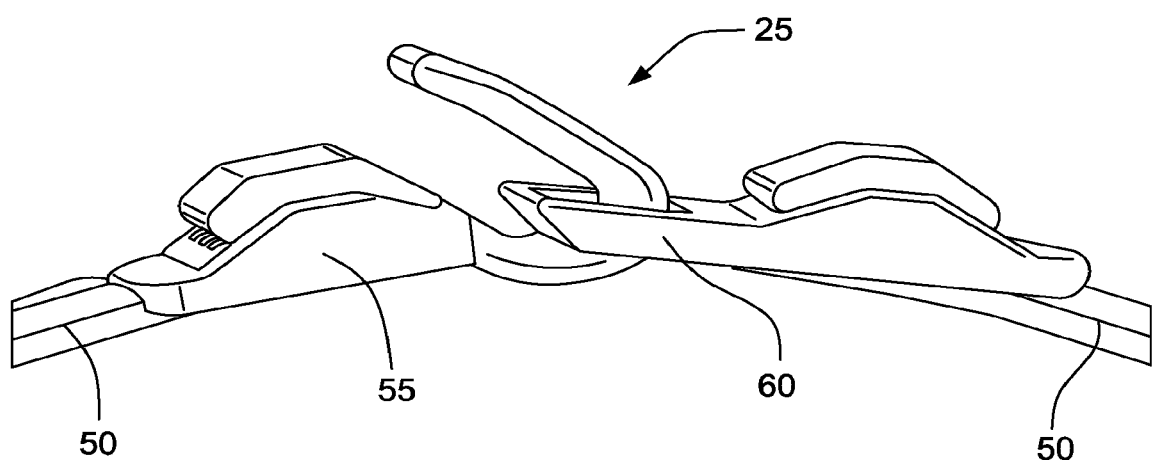
FIG. 90 shows a side view of a clasp of the headgear of FIG. 1 in a connected state.

In an alternative embodiment, the silicone cheek pad 21 may be retrofit to the rigidizer 80. For example, as shown in FIGS. 83 and 84, the silicone cheek pad 21 may include male press studs 27 along its length structured to mechanically lock with respective holes 29 along the rigidiser 80.

3. Clasp and Top Strap Adjustment

A clasp releasably connects the top straps of the headgear to facilitate donning of the mask or removal of the mask from the patient's head in use, e.g., easy fit. In addition, the clasp facilitates adjustment of the top strap in use. In the illustrated embodiments, the clasp is located at or adjacent the crown of the patient's head but may be located to one side of the patient's head in other embodiments.

3.1 Clasp Embodiments

Referring to FIGS. 85-90, the male clasp portion 55 of the clasp 25 comprises a first ladderlock portion 85 for engaging an upper end 50 of one of the top straps 20 and a hook portion 90 for engaging the female clasp portion 60. The female clasp portion 60 of the clasp 25 comprises a second ladderlock portion 95 for engaging an upper end 50 of the other of the top straps 20 and an aperture portion 100 for engaging the hook portion 90 of the male clasp portion 55.

Both the male clasp portion 55 and the female clasp portion 60 are sufficiently large to be easily gripped, and the hook portion 90 and aperture portion 100 are also sufficiently large so that they can be readily connected to one another. In one embodiment, the hook portion 90 has a radiused or chamfered end so that the hook portion can be directed or guided into the aperture portion 100. In another embodiment, the male and female clasp portions 55, 60 are adapted to sit substantially flat on the patient's head so that the force is relatively evenly distributed across the patient's head.

The aperture portion 100 provides a 'target window' for receiving the hook portion 90. To an extent, the larger the target window, the easier it is for the patient to connect the hook portion 90 to the aperture portion 100. In the illustrated embodiment, the hook portion is oriented away from the patient's head in use. Such arrangement may facilitate connection/disconnection as the hook portion is easily visible and manually accessible.

The clasp 25 may have a lateral fixed angle (i.e., the top straps 20 are maintained co-linearly or at another suitable angle with respect to each other). In one embodiment, the clasp 25 may comprise a very small hook and loop similar to that provided on bras.

Figure 2:
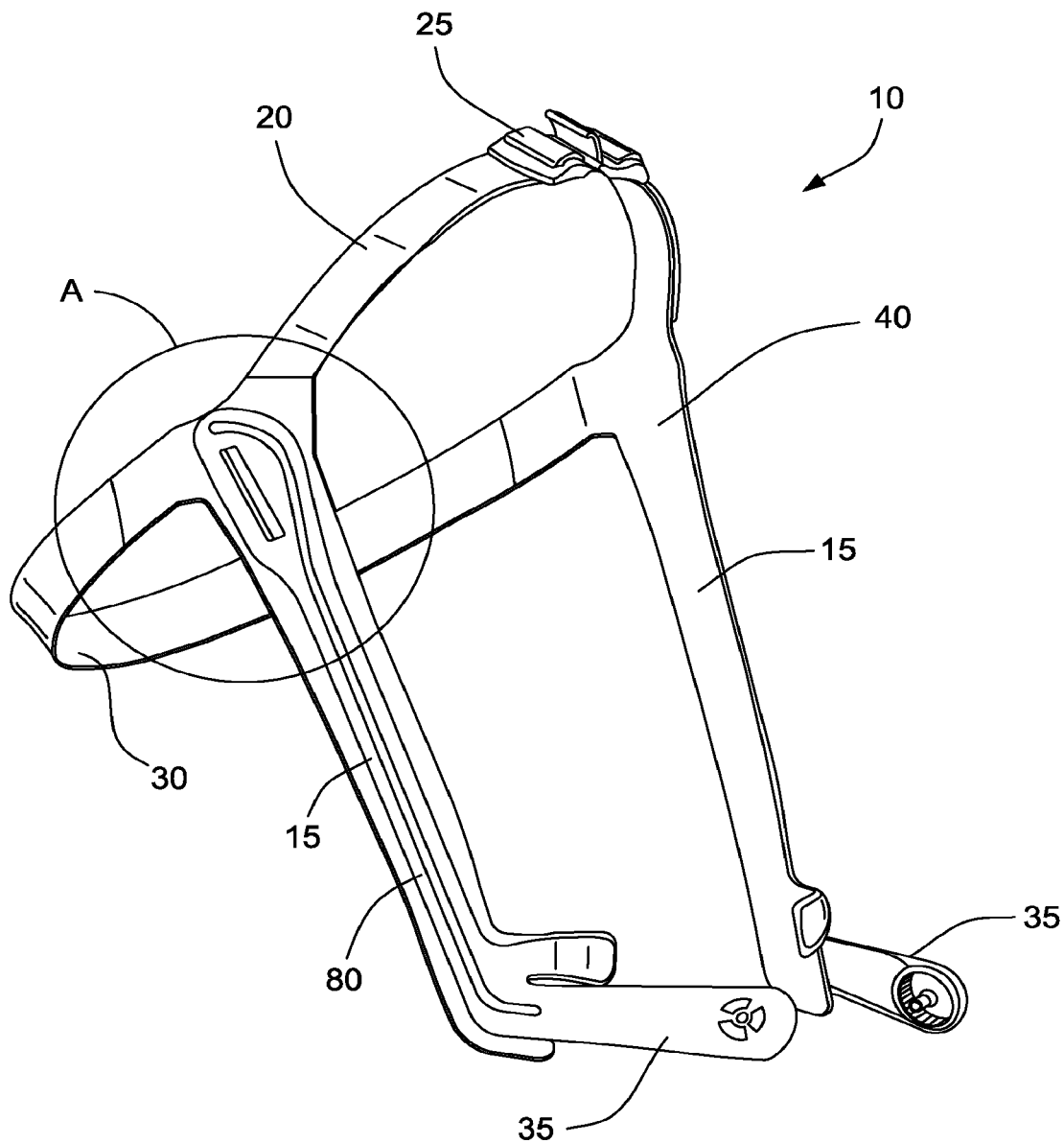
FIG. 2 shows a right-side perspective view of the headgear of FIG. 1.
Figures 1, 91:
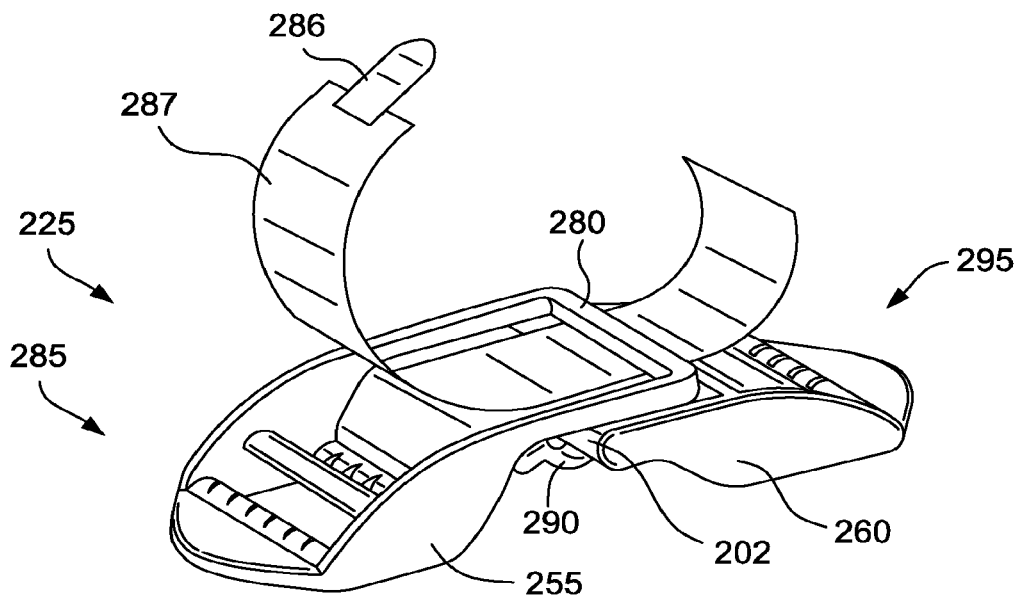
Figures 2, 91:
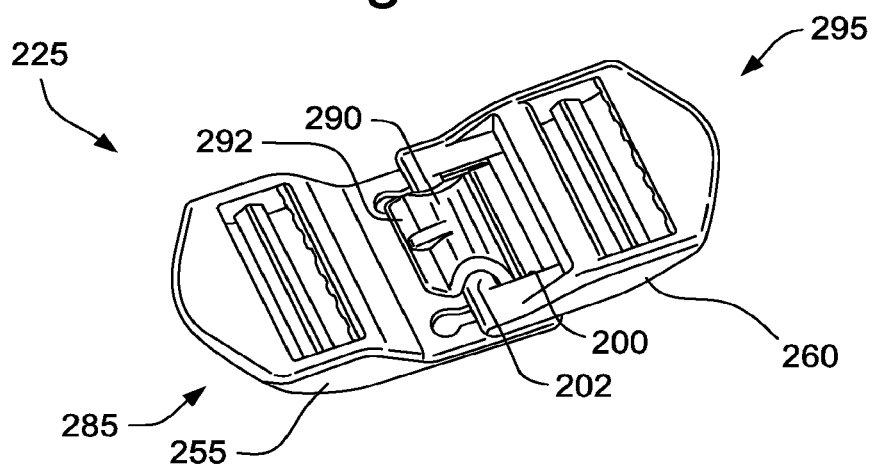
Figures 3, 91:
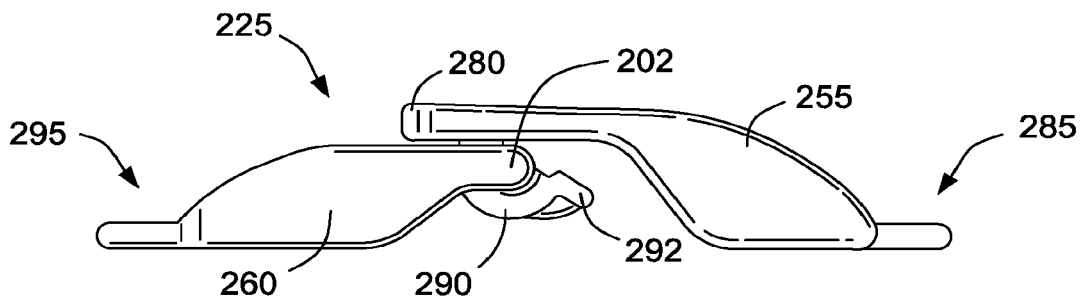
Figures 4, 91:
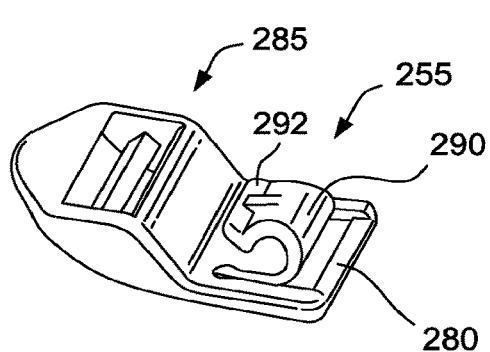
Figures 5, 91:
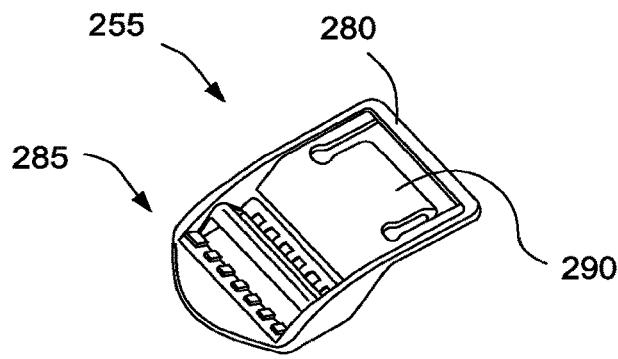
Figures 1, 92:
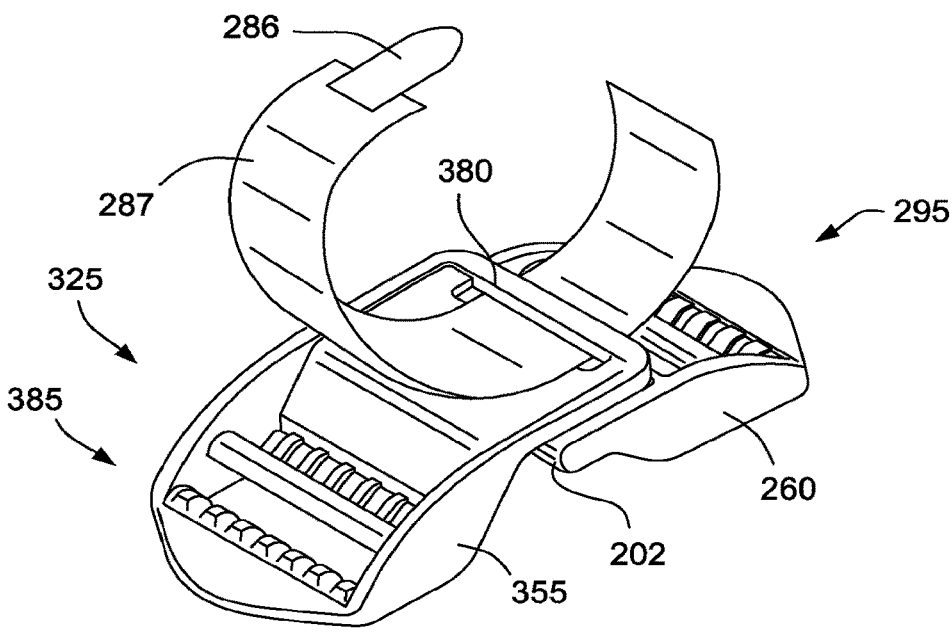
Figures 2, 92:
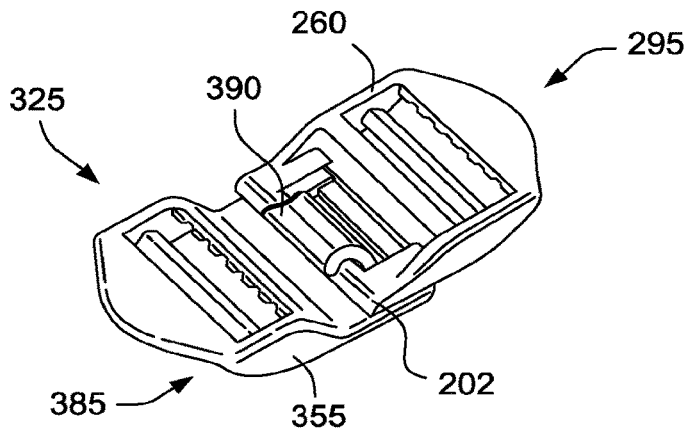
Figures 3, 92:
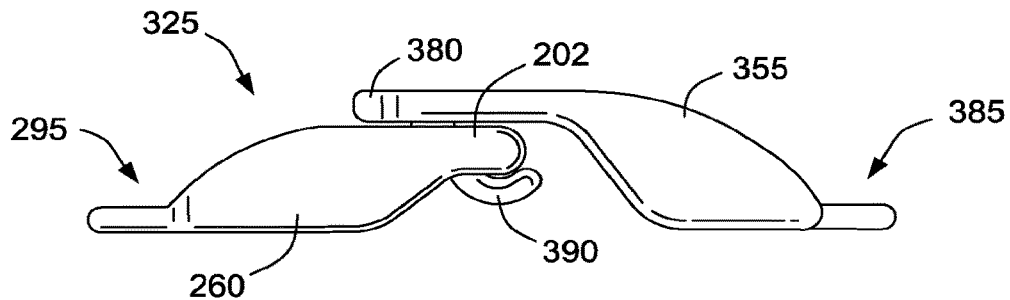
Figures 4, 5, 92:
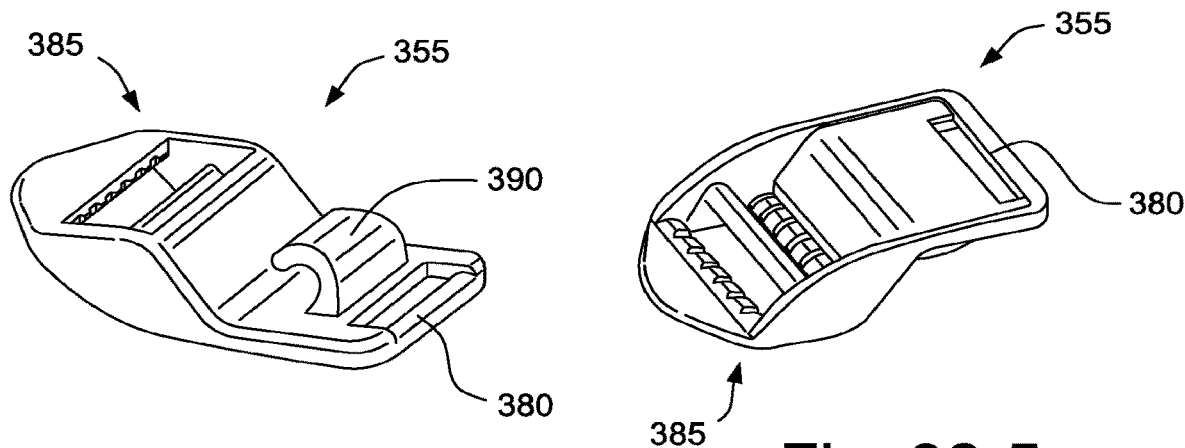
Figures 1, 2, 93:
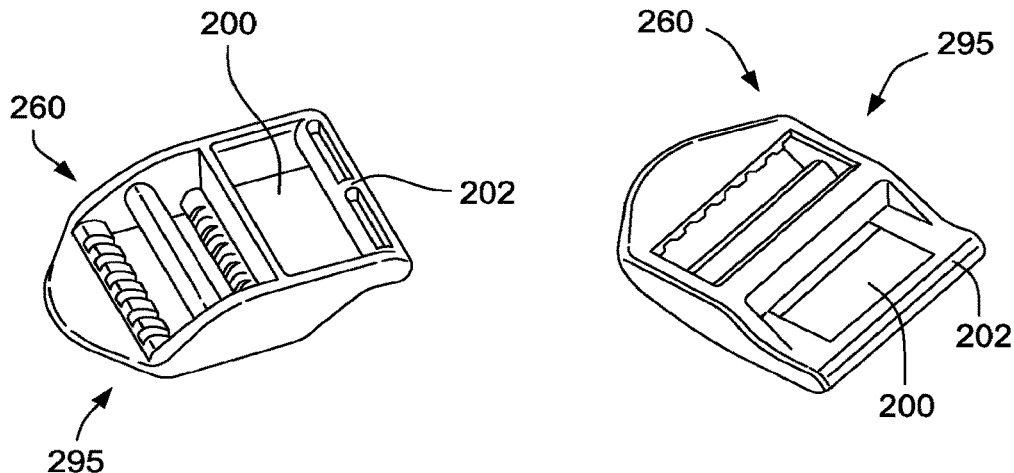
Figure 94:
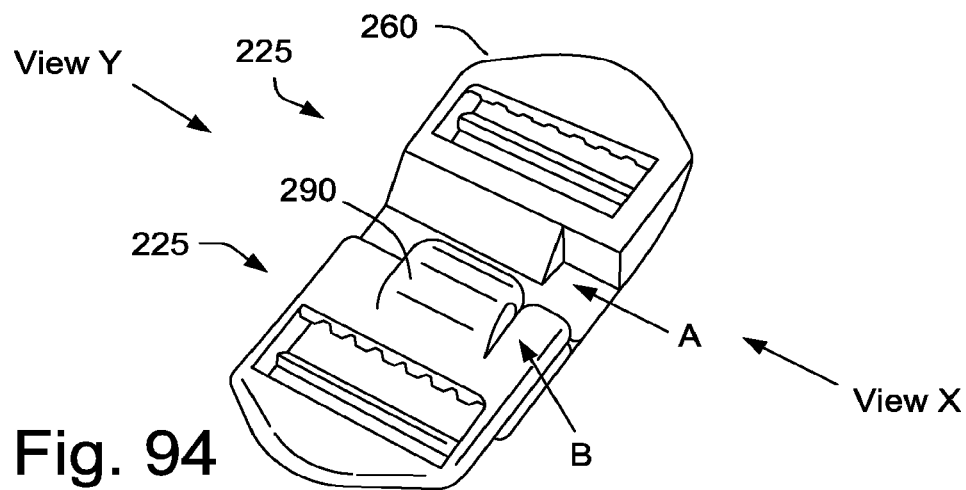
FIGS. 94 to 97 are various views of a clasp for headgear according to another embodiment of the present invention.
Figure 95:
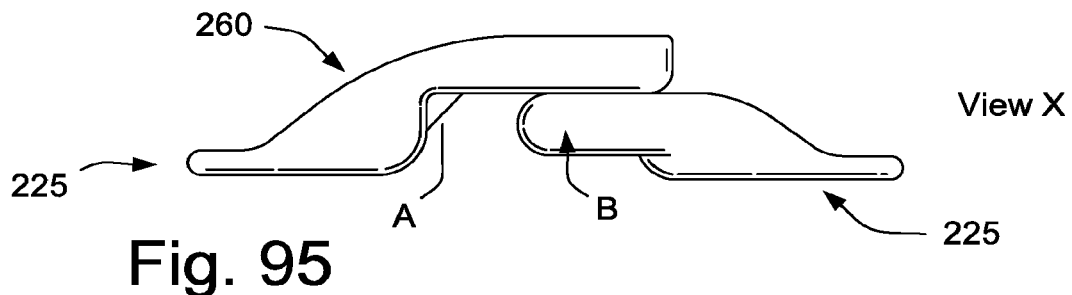
Figure 96:
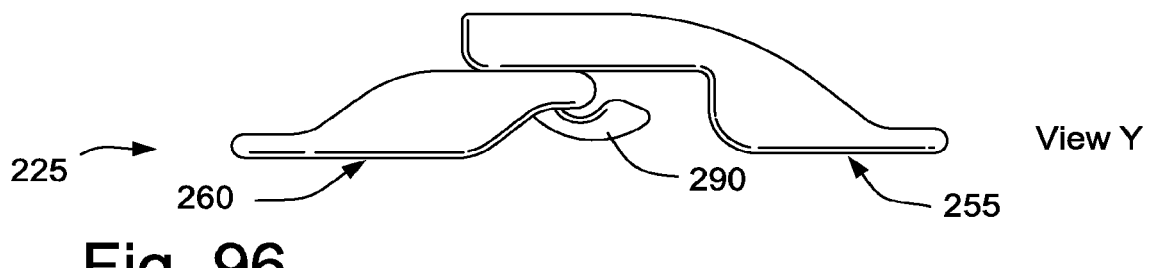
Figure 97:
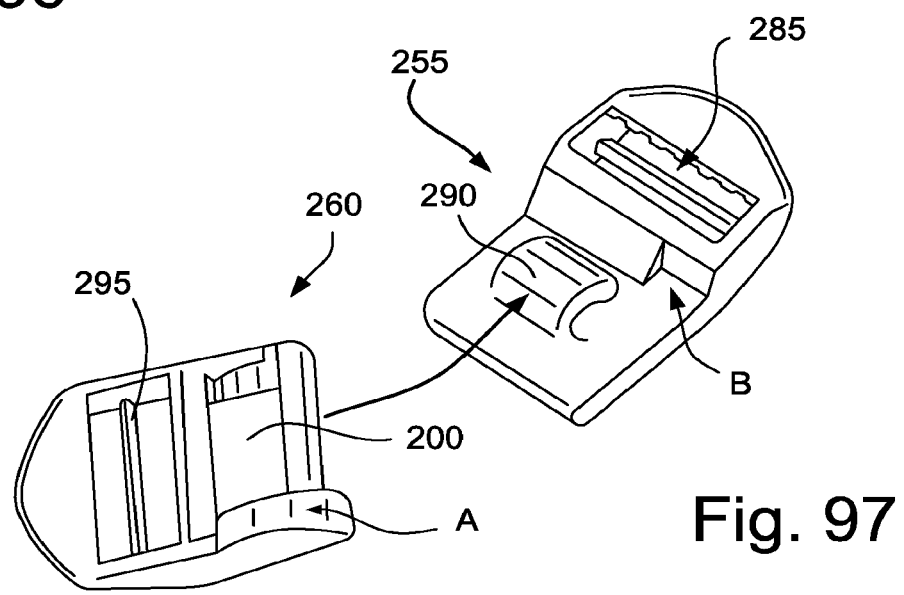

FIGS. 91-1 to 93-2 illustrate clasps according to alternative embodiments of the present invention. Specifically, FIGS. 91-1 to 91-5 illustrate clasp 225 with male and female clasp portions 255, 260, FIGS. 92-1 to 92-5 illustrate clasp 325 with male and female clasp portions 355, 260, and FIGS. 93-1 to 93-2 illustrate female clasp portion 260 which is common to both clasp 225, 325.

Figure 5:
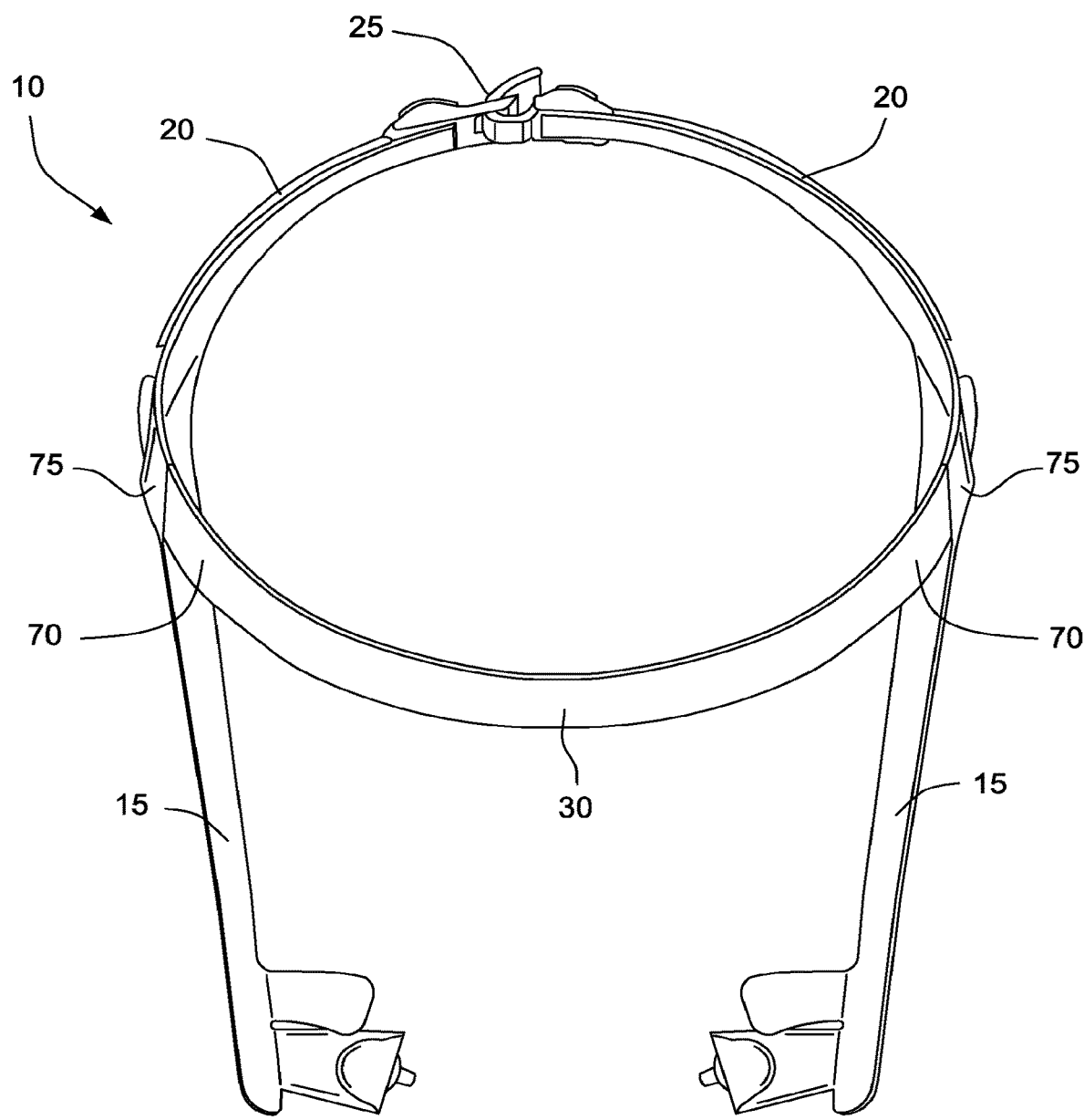
FIG. 5 shows a rear view of the headgear of FIG. 1.
Figure 6:
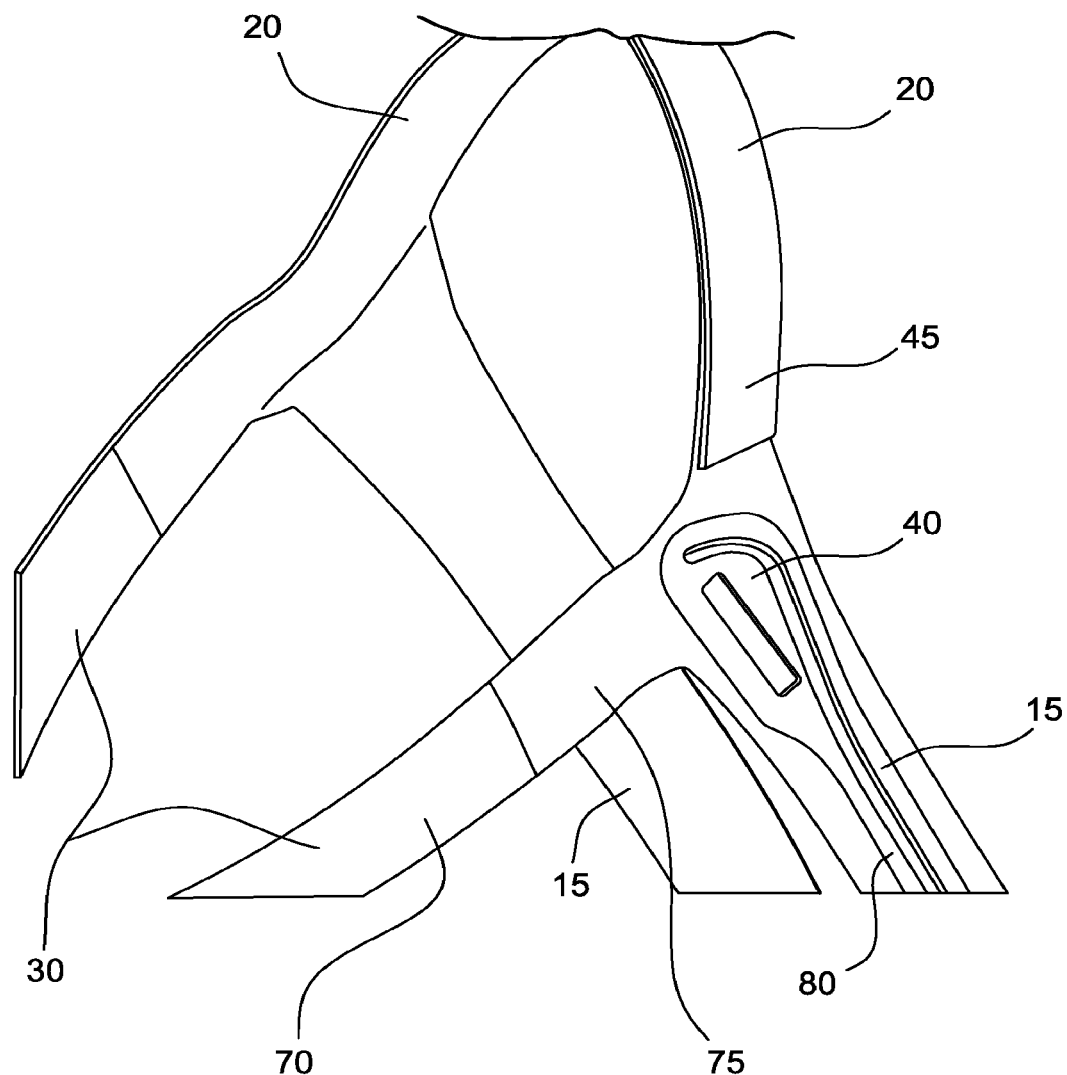
FIG. 6 shows an enlarged view of Region A of the headgear of FIG. 1 indicated in FIG. 2.

As illustrated in FIGS. 91-1 to 91-5, the male clasp portion 255 of the clasp 225 comprises a first ladderlock portion 285 for engaging an upper end 50 of one of the top straps 20 and a hook portion 290 for engaging the female clasp portion 260, and the female clasp portion 260 comprises a second ladderlock portion 295 for engaging an upper end 50 of the other of the top straps 20 and a cross-bar 202 defining an aperture portion 200 for engaging the hook portion 290 of the male clasp portion 255.

In this embodiment, the hook portion 290 is in the form of a spring clip adapted to extend through the aperture portion 200 and engage the cross-bar 202 with a snap-fit. The hook portion 290 includes a tab 292 that is oriented to engage the cross-bar 202 during connection and flex the hook portion 290 open so as to receive the cross-bar 202.

Also, in the connected state (e.g., see FIGS. 91-1 and 91-3), the clasp 225 provides a low profile with the hook portion 290 oriented towards the patient's head.

In addition, the male clasp portion 255 provides a cross-bar 280 adjacent the hook portion 290 which allows a soft tube retainer 287 to be wrapped or looped therearound. Specifically, the soft tube retainer 287 is in the form of a short strap portion including a Velcro® tab 286 adapted to secure the loop in position. The soft tube retainer 287 is adapted to wrap or loop around the cross-bar 280 and around the air delivery tube so as to retain the air delivery tube in an upward position over the top of the patient's head.

With respect to clasp 325 (shown in FIGS. 92-1 to 92-5), the male clasp portion 355 comprises a first ladderlock portion 385 for engaging an upper end 50 of one of the top straps 20 and a hook portion 390 for passing through aperture portion 200 and engaging the cross-bar 202 of the female clasp portion 260.

In this embodiment, the hook portion 390 is in the form of a C-clip adapted to extend through the aperture portion 200 and receive the cross-bar 202 therewithin. In contrast to the spring clip type hook portion 290 described above, the hook portion 390 does not releasably engage the cross-bar 202 with a snap-fit, rather the hook portion 390 provides sufficient clearance to receive the cross-bar 202 therewithin.

Figure 3:
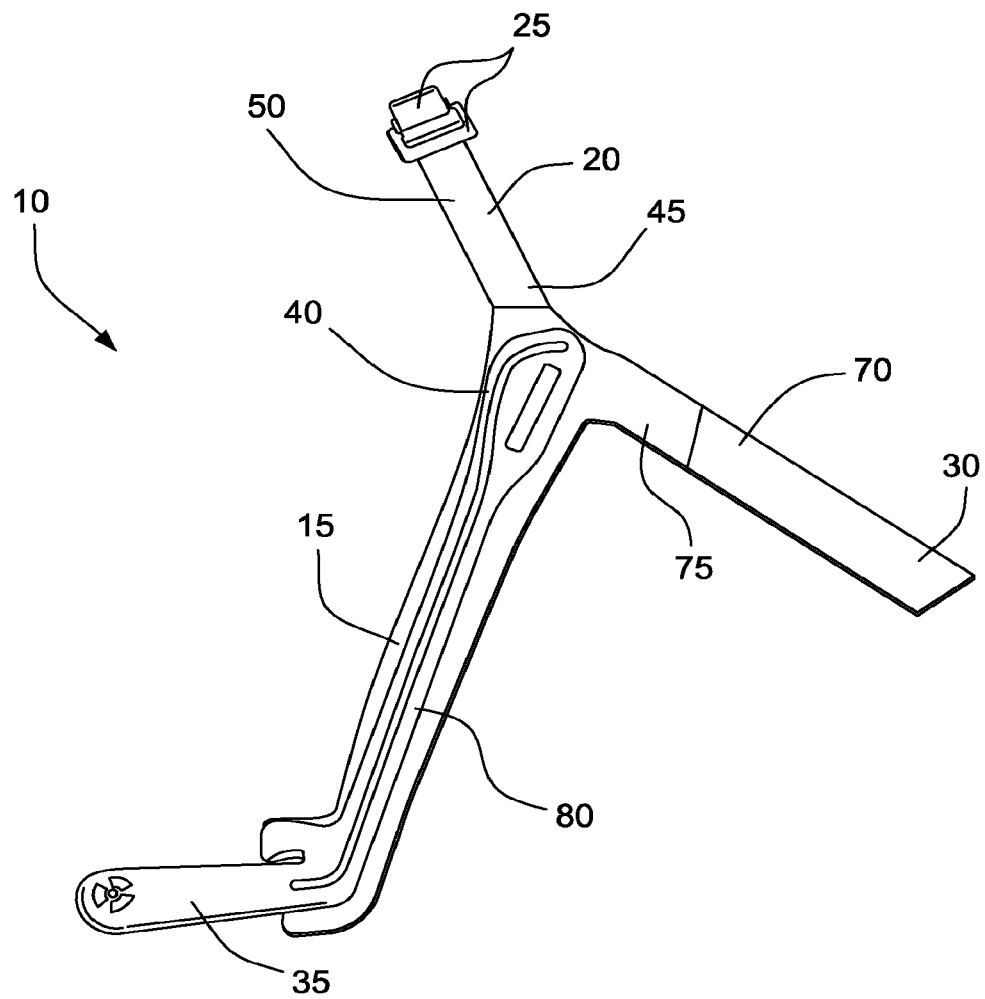
FIG. 3 shows a left side view of the headgear of FIG. 1.
Figure 4:
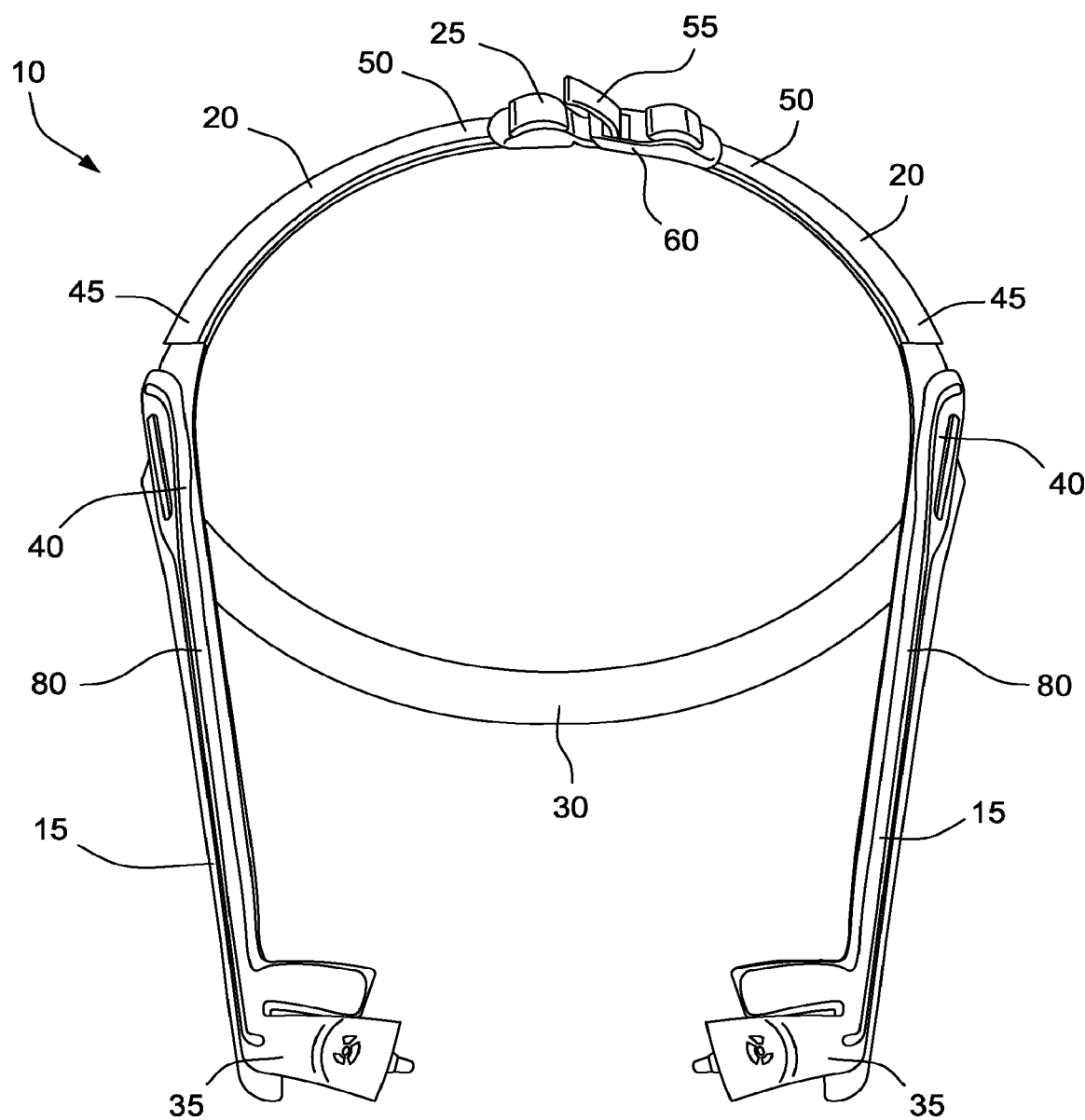
FIG. 4 shows a front view of the headgear of FIG. 1.

Similar to clasp 225, the clasp 325 provides a low profile with the hook portion 390 oriented towards the patient's head in the connected state (e.g., see FIGS. 92-1 and 92-3). In addition, the male clasp portion 355 provides a cross-bar 380 adjacent the hook portion 390 which allows a soft tube retainer 287 to be wrapped or looped therearound for retaining the air delivery tube as described above.

In one form, features may be provided to the clasp 225 so as to prevent incorrect assembly. For example, a cut out or groove A may be provided on male clasp portion 255 and a ridge or protrusion B may be provided to the female clasp portion 260, as shown in FIGS. 94 to 97.

In one embodiment, at least one of the top straps 20 further comprises an adjustment device to facilitate adjustment of its length. In another embodiment, each of the top straps 20 comprises an adjustment device to facilitate adjustment of its length. In the illustrated embodiment, the clasp 25 can be maintained centrally over the crown of the patient's head. As such, the patient may rest on either side of their head without the clasp 25 pressing against their head (which may cause discomfort). Suitable types of adjustment devices are hook and loop (e.g., Velcro®) type adjustments and ladder-lock adjustments, like those provided on bras.

Advantageously, the top straps 20 can be connected or disconnected independently of adjustment of the headgear. The clasp 25 is simpler to use than an equivalent hook and loop style attachment, which is particularly helpful since it is located out of the patient's line of sight. Sometimes hook and loop attachments can catch hair between the hook and loop portions and this problem is particularly pronounced for patients who have long hair. Another disadvantage, associated with using hook and loops attachments as the main top strap connector is that hook and loop material (e.g., Velcro®) wears out relatively quickly. Therefore, embodiments of the invention are particularly advantageous since the mask can be donned or taken off without having to use a hook and loop style attachment.

In an embodiment, the clasp 25 only includes a single hook and a single corresponding aperture to avoid the connection being done up improperly.

In one embodiment, the clasp 25 is the same width as the top straps 20 or a similar width.

FIGS. 98a to 128 illustrate clasps or buckles according to alternative embodiments of the present invention. Similar to the embodiments described above, each clasp includes male and female clasp portions that are adapted to releasably connect to each other. For example, FIGS. 98a and 98b, 99, 101, 103a and 103b, 105-107, 108, 115a and 115b, and 117 illustrate clasp embodiments with a hook and opening arrangement, FIGS. 102b, 104a and 104b, 109, 114, 118a and 118b, 121, and 122 illustrate clasp embodiments having a pin and hole arrangement, FIGS. 100a, 116, 123-125, and 127 illustrate clasp embodiments having a T-bar and hook arrangement, and FIGS. 119a and 128 illustrate clasp embodiments having a pin and hook arrangement.

In addition, the clasp may be structured to support a c-shaped tube retainer (e.g., see FIGS. 112, 113, 114, 115a and 115b, 118b, 119a, 122-125, and 127-128) or a soft tube retainer (e.g., see FIGS. 111, 117, and 121) for retaining the air delivery tube.

Figure 98A:
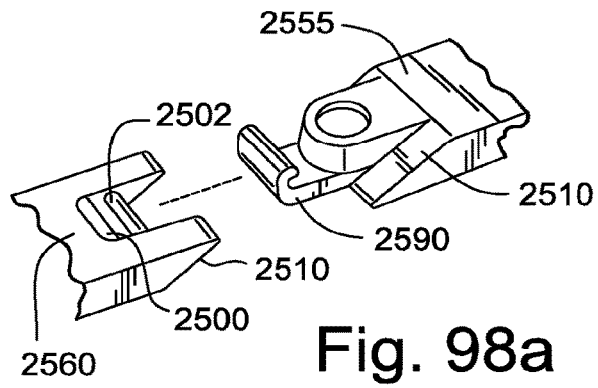
FIG. 98a is a perspective view of a clasp for headgear according to another embodiment of the present invention.
Figure 98B:
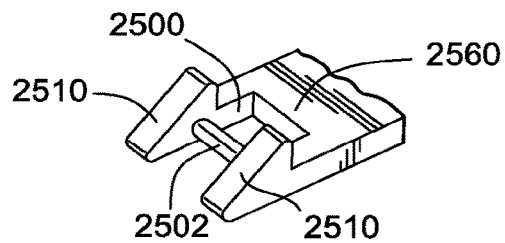
Figure 116:
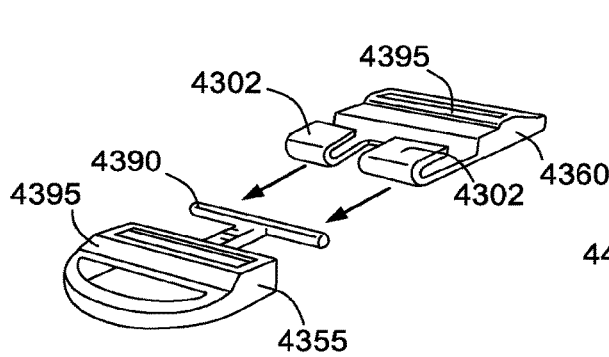
FIG. 116 is a perspective view of a clasp for headgear according to another embodiment of the present invention.

In embodiment, the clasp or buckle may be structured such that when the headgear is tightened or in tension, the clasp or buckle will not bend or flex inwards towards the patient's head. This arrangement is to avoid pressure points on the patient's head and avoid unduly messing up the patient's hair. For example, FIGS. 98a and 98b show a buckle that will not flex inwards towards the patient's head as the ramps 2510 won't allow the cross bar 2502 to flex once in a connected position. Alternatively, FIG. 116 shows a buckle that may flex towards the patient's head, e.g., no ramps.

In FIGS. 98a and 98b, the male clasp portion 2555 of the clasp includes a hook portion 2590 for passing through aperture portion 2500 and engaging the cross-bar 2502 of the female clasp portion 2560. As illustrated, the male and female clasp portions 2555, 2560 provide complementary ramps 2510 to prevent wrong assembly. Also, while not shown, the male and female clasp portions may provide ladderlock portions for engaging respective headgear straps.

Figure 99:
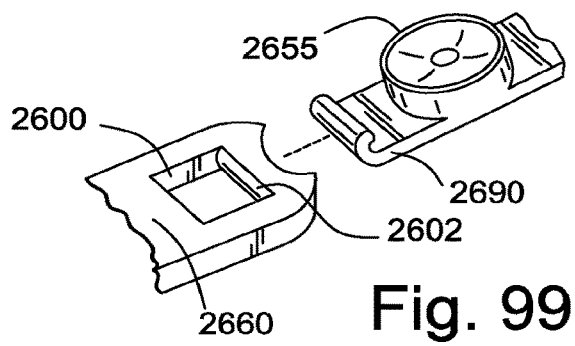
FIG. 99 is a perspective view of a clasp for headgear according to another embodiment of the present invention.

In FIG. 99, the male clasp portion 2655 of the clasp includes a hook portion 2690 for passing through aperture portion 2600 and engaging the cross-bar 2602 of the female clasp portion 2660. Also, while not shown, the male and female clasp portions may provide ladderlock portions for engaging respective headgear straps.

Figure 100A:
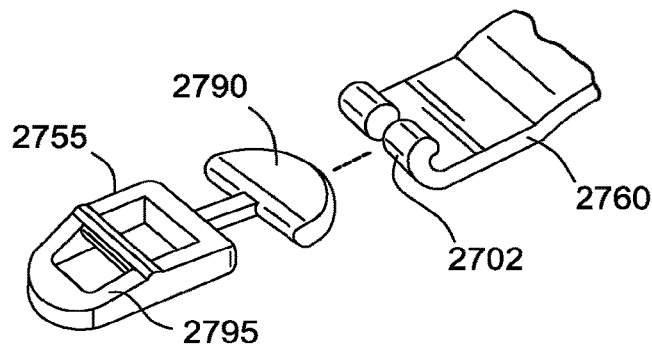
FIG. 100a is a perspective view of a clasp for headgear according to another embodiment of the present invention.
Figure 100B:
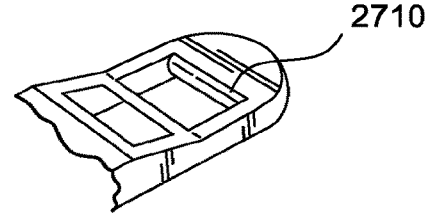
FIG. 100b is a perspective view of a female clasp portion according to another embodiment of the present invention.

In FIG. 100a, the male clasp portion 2755 of the clasp includes a T-bar portion 2790 for engaging the hook portion 2702 of the female clasp portion 2760. Alternatively, as shown in FIG. 100b, the T-bar portion may be replaced with a cross-bar 2710 for engaging the hook portion 2702. Also, the male and female clasp portions may provide ladderlock portions (e.g., such as ladderlock portion 2795 on male clasp portion 2755) for engaging respective headgear straps.

Figure 101:
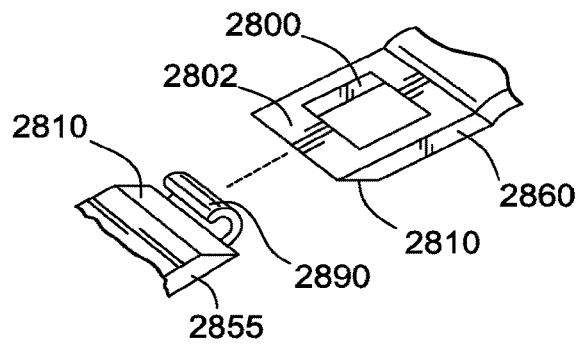
FIG. 101 is a perspective view of a clasp for headgear according to another embodiment of the present invention.

In FIG. 101, the male clasp portion 2855 of the clasp includes a hook portion 2890 for passing through aperture portion 2800 and engaging the cross-bar 2802 of the female clasp portion 2860. As illustrated, the male and female clasp portions 2855, 2860 provide complementary ramps 2810 to prevent wrong assembly. Also, while not shown, the male and female clasp portions may provide ladderlock portions for engaging respective headgear straps.

Figure 102A:
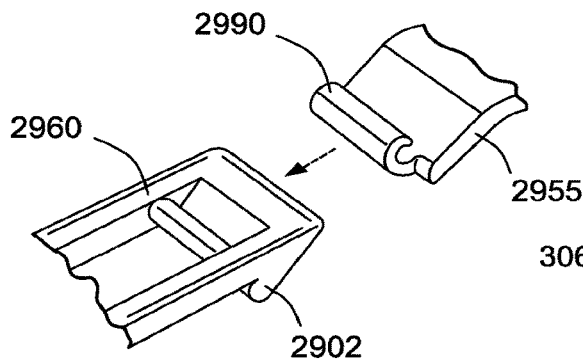
FIG. 102a is a perspective view of a clasp for headgear according to another embodiment of the present invention.
Figure 102B:
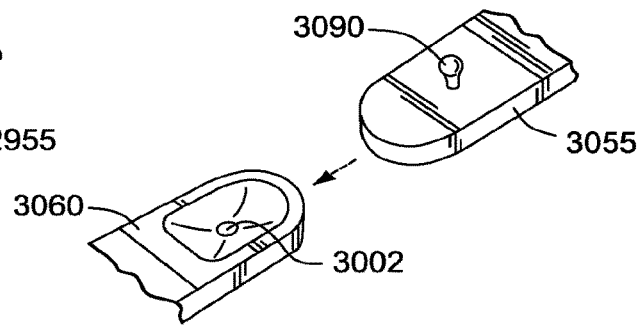
FIG. 102b is a perspective view of a clasp for headgear according to another embodiment of the present invention.

In FIG. 102a, the male clasp portion 2955 of the clasp includes a hook portion 2990 for engaging a cross-bar 2902 of the female clasp portion 2960. Alternatively, as shown in FIG. 102b, the male clasp portion 3055 of the clasp may include a pin 3090 for passing through an opening 3002 of the female clasp portion 3060. Also, while not shown, each of the male and female clasp portions may provide ladder-lock portions for engaging respective headgear straps.

Figure 103A:
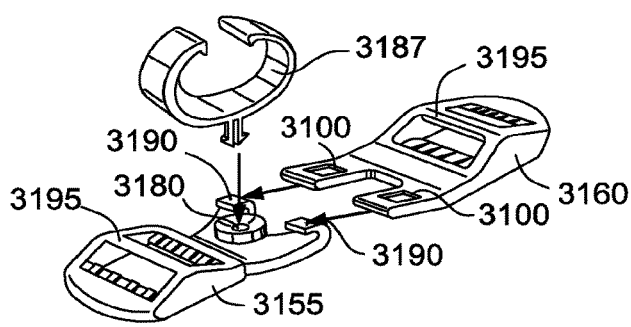
FIG. 103a is a perspective view of a clasp for headgear according to another embodiment of the present invention.
Figure 103B:
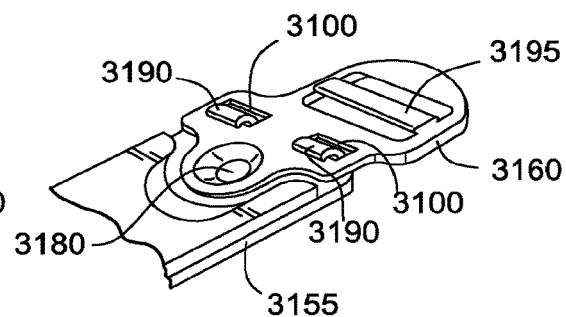
FIG. 103b is a perspective view of the clasp of FIG. 103a in a connected state.

In FIGS. 103a and 103b, the male clasp portion 3155 of the clasp includes spaced apart hook portions 3190 for passing through spaced apart apertures 3100 of the female clasp portion 3160. Also, the male and female clasp portions may provide ladderlock portions 3195 for engaging respective headgear straps. In addition, the male clasp portion 3155 provides an aperture 3180 for engagement with a c-shaped tube retainer 3187.

Figure 104A:
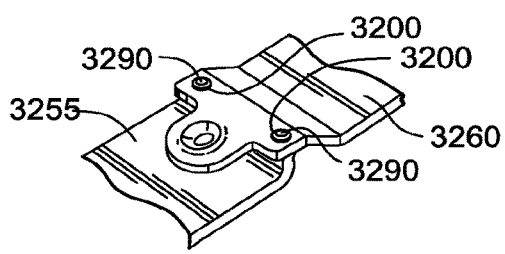
FIG. 104a is a perspective view of a clasp for headgear according to another embodiment of the present invention.
Figure 104B:
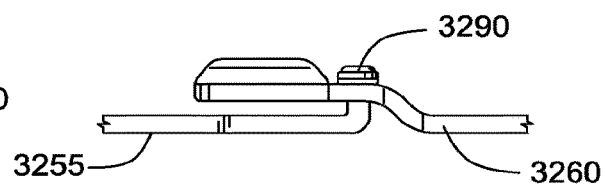

In FIGS. 104a and 104b, the male clasp portion 3255 of the clasp includes spaced apart pins 3290 for passing through spaced apart apertures 3200 of the female clasp portion 3260. Also, while not shown, each of the male and female clasp portions may provide ladderlock portions for engaging respective headgear straps.

Figure 105:
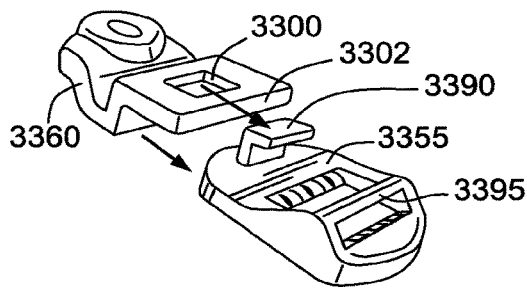
FIG. 105 is a perspective view of a clasp for headgear according to another embodiment of the present invention.

In FIG. 105, the male clasp portion 3355 of the clasp includes a hook portion 3390 for passing through aperture portion 3300 and engaging the cross-bar 3302 of the female clasp portion 3360. Also, the male and female clasp portions may provide ladderlock portions (e.g., such as ladderlock portion 3395 on male clasp portion 3355) for engaging respective headgear straps.

Figure 106:
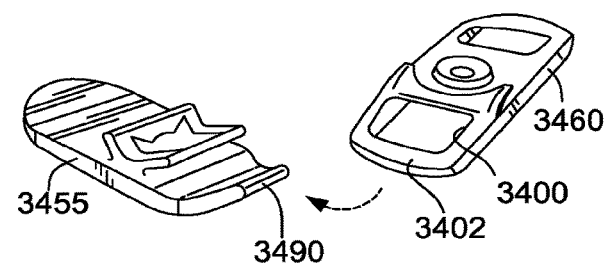
FIG. 106 is a perspective view of a clasp for headgear according to another embodiment of the present invention.

In FIG. 106, the male clasp portion 3455 of the clasp includes a hook portion 3490 for passing through aperture portion 3400 and engaging the cross-bar 3402 of the female clasp portion 3460. Also, the male and female clasp portions may provide ladderlock portions for engaging respective headgear straps.

Figure 107:
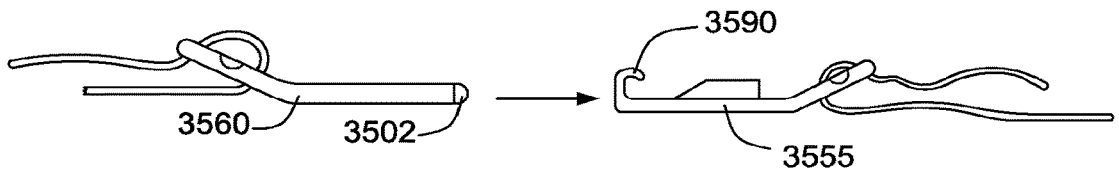
FIG. 107 is a side view of a clasp for headgear according to another embodiment of the present invention.

In FIG. 107, the male clasp portion 3555 of the clasp includes a hook portion 3590 for engaging the cross-bar 3502 of the female clasp portion 3560. Also, the male and female clasp portions may provide ladderlock portions for engaging respective headgear straps.

Figure 108:
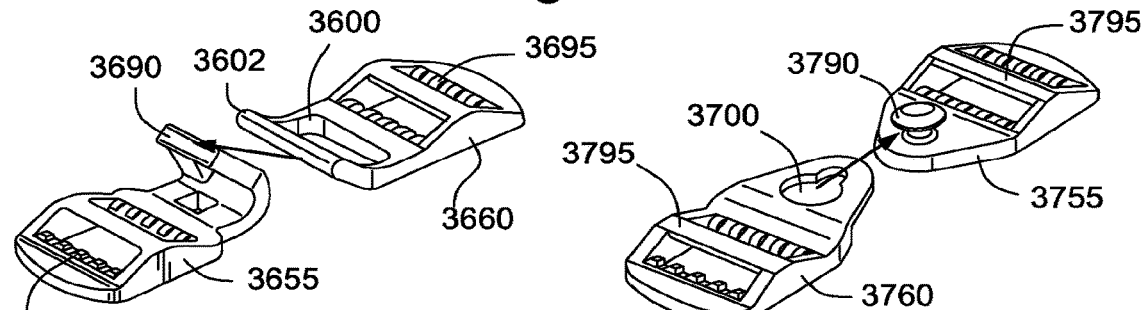
FIG. 108 is a perspective view of a clasp for headgear according to another embodiment of the present invention.

In FIG. 108, the male clasp portion 3655 of the clasp includes a hook portion 3690 for passing through aperture portion 3600 and engaging the cross-bar 3602 of the female clasp portion 3660. Also, the male and female clasp portions provide ladderlock portions 3695 for engaging respective headgear straps.

Figure 109:
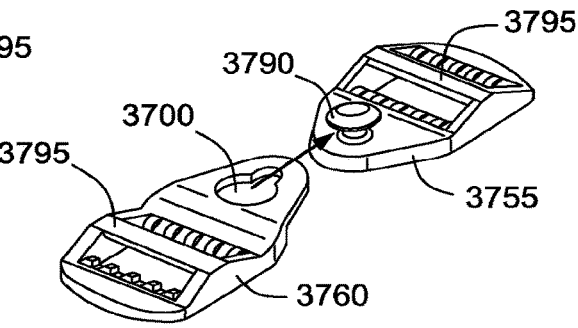
FIG. 109 is a perspective view of a clasp for headgear according to another embodiment of the present invention.

In FIG. 109, the male clasp portion 3755 of the clasp includes a pin 3790 for passing through an aperture 3700 of the female clasp portion 3760. Also, the male and female clasp portions provide ladderlock portions 3795 for engaging respective headgear straps.

Figure 110A:
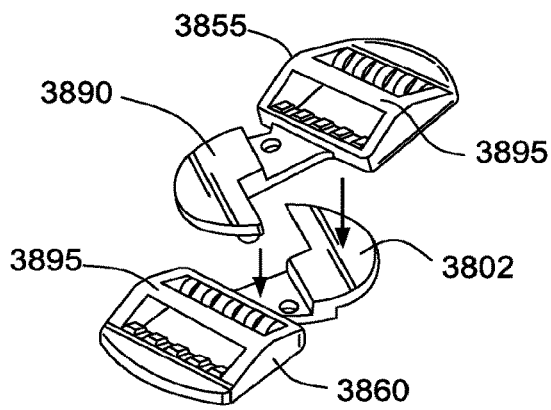
FIG. 110a is a perspective view of a clasp for headgear according to another embodiment of the present invention.
Figure 110B:
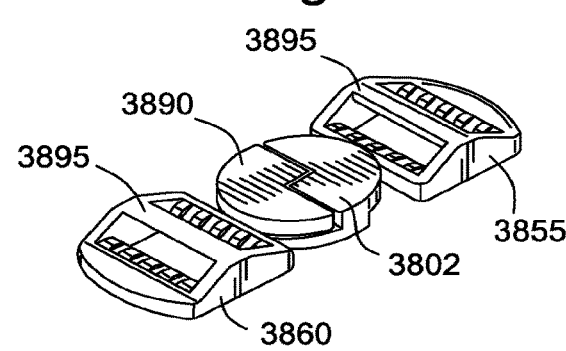
FIG. 110b is a perspective view of the clasp of FIG. 110a in a connected state.

In FIGS. 110a and 110b, one of clasp portions 3855 of the clasp includes a first interlocking structure 3890 for engaging and interlocking with a complementary second interlocking structure 3802 provided to the other of the clasp portions 3860. In the illustrated embodiment, the first and second interlocking structures provide an interlocking stair-step arrangement. Also, the male and female clasp portions provide ladderlock portions 3895 for engaging respective headgear straps.

Figure 111:
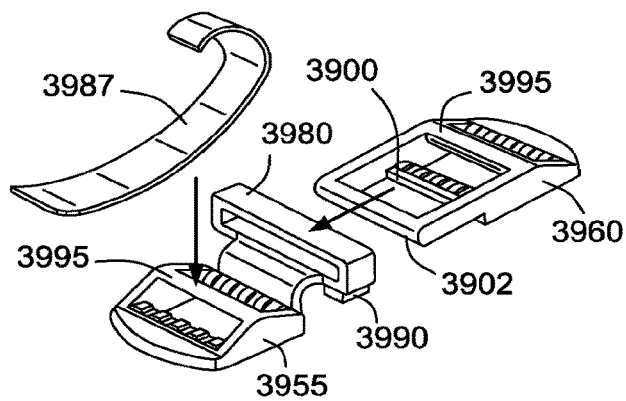
FIG. 111 is a perspective view of a clasp for headgear according to another embodiment of the present invention.

In FIG. 111, the male clasp portion 3955 of the clasp includes a hook portion 3990 for passing through aperture portion 3900 and engaging the cross-bar 3902 of the female clasp portion 3960. Also, the male and female clasp portions provide ladderlock portions 3995 for engaging respective headgear straps. In addition, the male clasp portion 3955 provides a cross-bar 3980 which allows a soft tube retainer 3987 to be wrapped or looped therearound.

Figure 112:
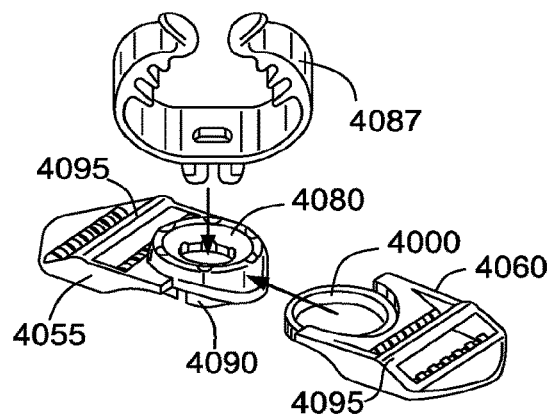
FIG. 112 is a perspective view of a clasp for headgear according to another embodiment of the present invention.

In FIG. 112, the male clasp portion 4055 of the clasp includes an annular retaining portion 4090 for passing through and engaging a ring-shaped aperture portion 4000 of the female clasp portion 4060, e.g., with a snap-fit. Also, the male and female clasp portions provide ladderlock portions 4095 for engaging respective headgear straps. In addition, the male clasp portion 4055 provides an aperture 4080 for engagement with a c-shaped tube retainer 4087.

Figure 113:
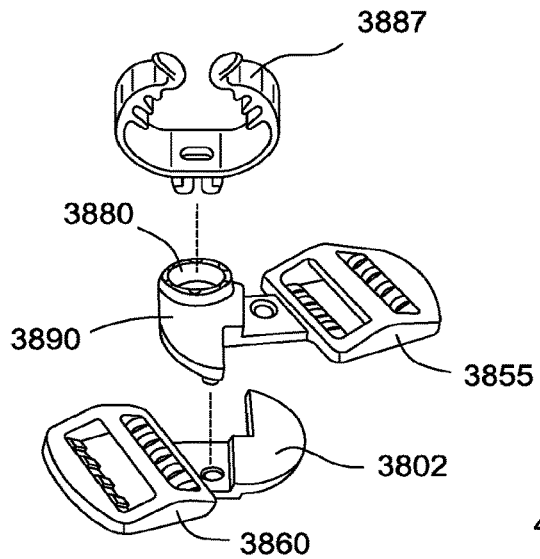
FIG. 113 is a perspective view of a clasp for headgear according to another embodiment of the present invention.

FIG. 113 shows a clasp similar to that shown in FIG. 110 and indicated with similar reference numerals, i.e., first and second complementary interlocking structures 3890, 3802. In contrast, the clasp portion 3855 in FIG. 113 provides an aperture 3880 for engagement with a c-shaped tube retainer 3887.

Figure 114:
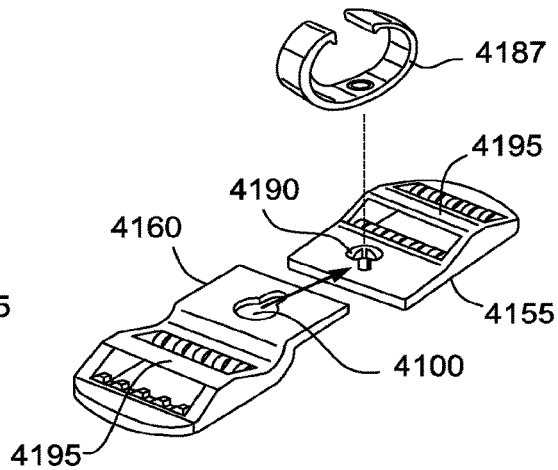
FIG. 114 is a perspective view of a clasp for headgear according to another embodiment of the present invention.

In FIG. 114, the male clasp portion 4155 of the clasp includes a pin 4190 for passing through an aperture 4100 of the female clasp portion 4160. Also, the male and female clasp portions provide ladderlock portions 4195 for engaging respective headgear straps. In addition, a c-shaped tube retainer 4187 includes an aperture for engagement with the pin 4190.

Figure 115A:
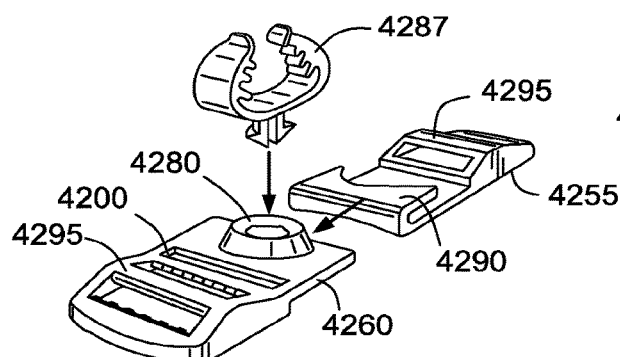
FIG. 115a is a perspective view of a clasp for headgear according to another embodiment of the present invention.
Figure 115B:
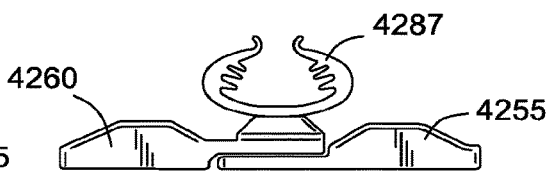

In FIGS. 115a and 115b, the male clasp portion 4255 of the clasp includes a hook portion 4290 for passing through aperture portion 4200 of the female clasp portion 4260. Also, the male and female clasp portions provide ladderlock portions 4295 for engaging respective headgear straps. In addition, the female clasp portion 4260 provides an aperture 4280 for engagement with a c-shaped tube retainer 4287.

In FIG. 116, the male clasp portion 4355 of the clasp includes a T-bar portion 4390 for engaging spaced apart hook portions 4302 of the female clasp portion 4360. Also, the male and female clasp portions provide ladderlock portions 4395 for engaging respective headgear straps.

Figure 117:
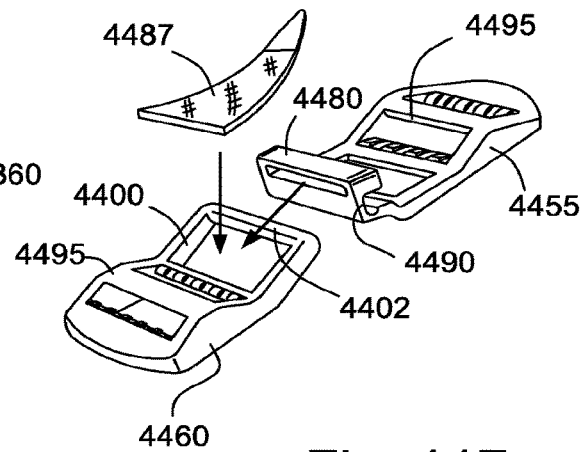

In FIG. 117, the male clasp portion 4455 of the clasp includes a hook portion 4490 for passing through aperture portion 4400 and engaging the cross-bar 4402 of the female clasp portion 4460. Also, the male and female clasp portions provide ladderlock portions 4495 for engaging respective headgear straps. In addition, the free end of the hook portion 4490 provides a cross-bar 4480 which allows a soft tube retainer 4487 to be wrapped or looped therearound.

Figure 118A:
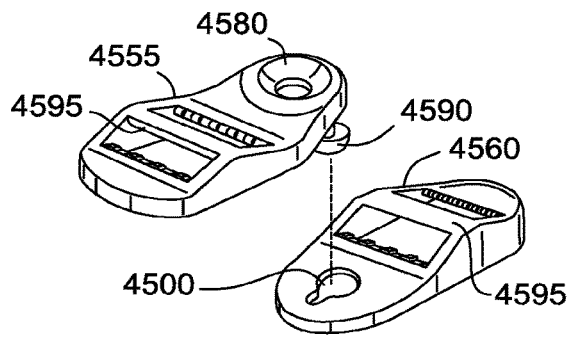
Figure 118B:
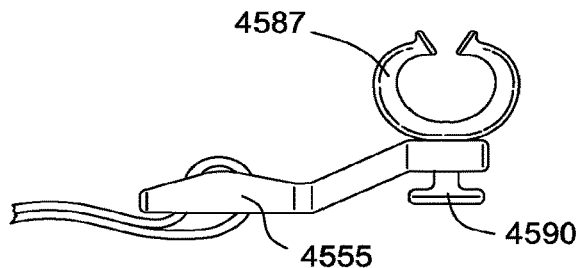
Figure 119A:
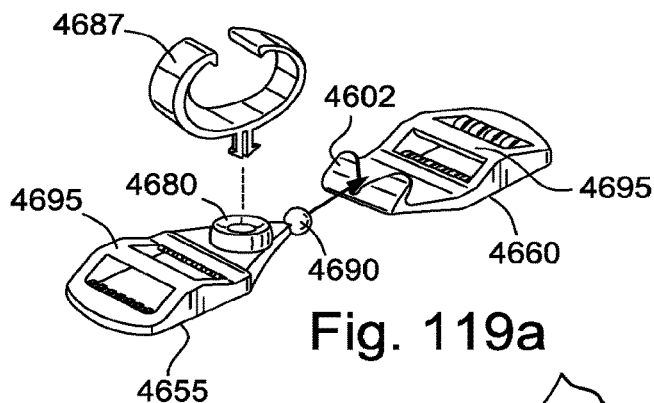

In FIGS. 118a and 118b, the male clasp portion 4555 of the clasp includes a pin 4590 for passing through an aperture 4500 of the female clasp portion 4560. Also, the male and female clasp portions provide ladderlock portions 4595 for engaging respective headgear straps. In addition, the male clasp portion 4555 provides an aperture 4580 for engagement with a c-shaped tube retainer 4587.

Figure 119B:
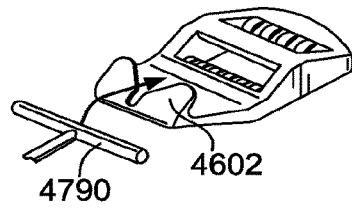

In FIG. 119a, the male clasp portion 4655 of the clasp includes a ball 4690 for engaging a hook portion 4602 of the female clasp portion 4660. Also, the male and female clasp portions provide ladderlock portions 4695 for engaging respective headgear straps. In addition, the male clasp portion 4655 provides an aperture 4680 for engagement with a c-shaped tube retainer 4687. Alternatively, as shown in FIG. 119b, the male clasp portion may include a T-bar portion 4790 for engaging the hook portions 4602.

Figure 120A:
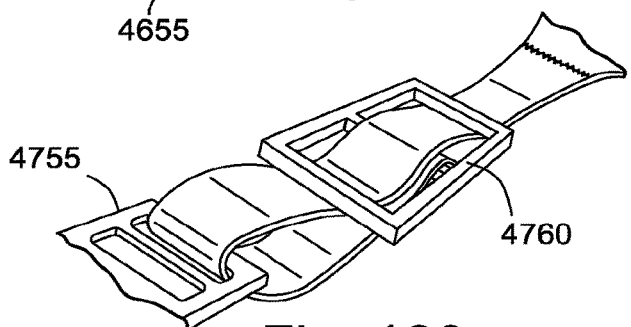
Figure 120B:
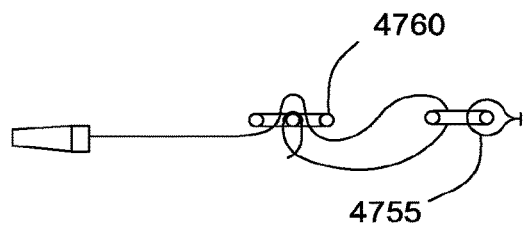

FIGS. 120a and 120b illustrate a buckle arrangement for coupling headgear straps. In this arrangement, a first buckle 4755 is provided to one headgear strap (e.g., via stitching) and a second buckle 4760 is provided to allow the other headgear strap to wrap around the first and second buckles 4755, 4760 and couple the headgear straps to one another.

Figure 121:
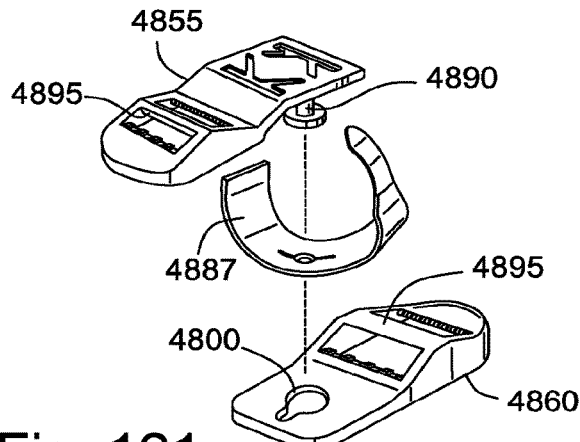

In FIG. 121, the male clasp portion 4855 of the clasp includes a pin 4890 for passing through an aperture 4800 of the female clasp portion 4860. Also, the male and female clasp portions provide ladderlock portions 4895 for engaging respective headgear straps. In addition, a soft tube retainer 4887 includes an aperture for engagement with the pin 4890.

Figure 122:
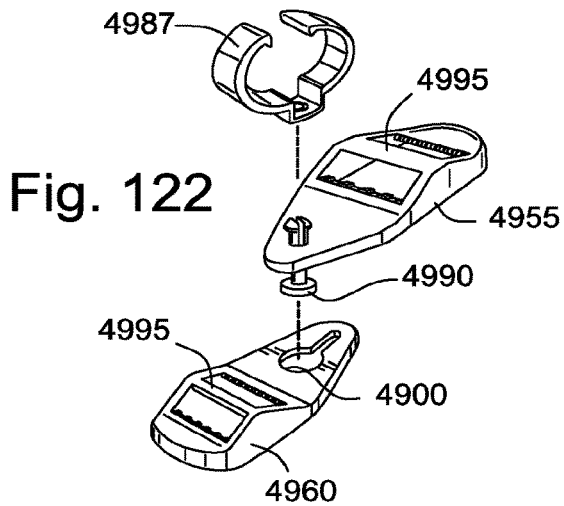

In FIG. 122, the male clasp portion 4955 of the clasp includes a pin 4990 for passing through an aperture 4900 of the female clasp portion 4960. Also, the male and female clasp portions provide ladderlock portions 4995 for engaging respective headgear straps. In addition, a c-shaped tube retainer 4987 includes an aperture for engagement with an end portion of the pin 4990, e.g., with a snap-fit.

Figure 123:
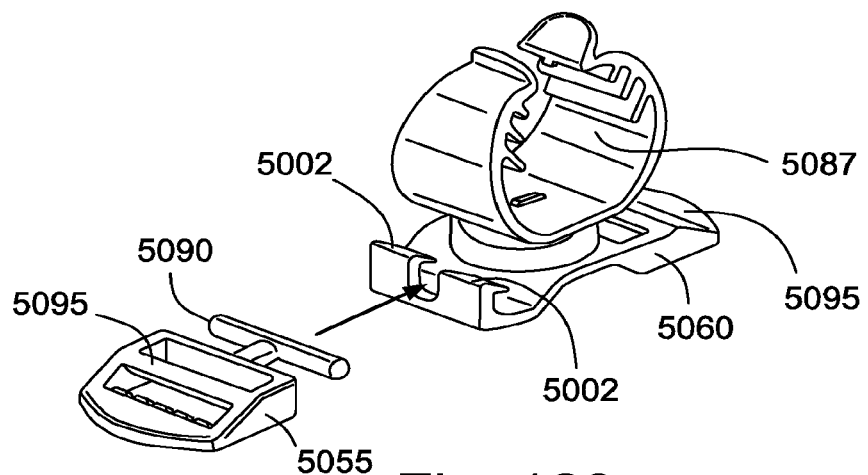

In FIG. 123, the male clasp portion 5055 of the clasp includes a T-bar portion 5090 for engaging spaced apart hook portions 5002 of the female clasp portion 5060. In the illustrated embodiment, the each hook portion provides a ramp-like configuration. Also, the male and female clasp portions provide ladderlock portions 5095 for engaging respective headgear straps. In addition, the female clasp portion 5060 provides an aperture (not visible) for engagement with a c-shaped tube retainer 5087.

Figure 124:
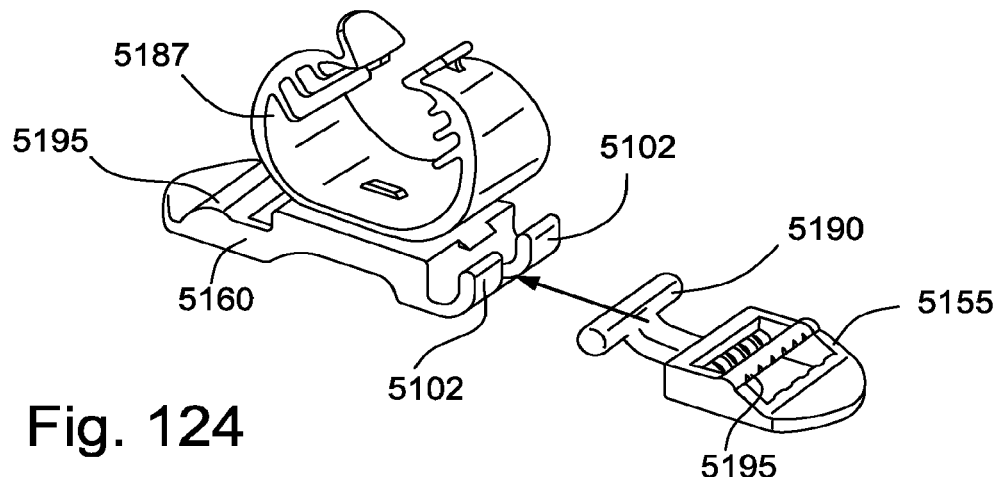

In FIG. 124, the male clasp portion 5155 of the clasp includes a T-bar portion 5190 for engaging spaced apart hook portions 5102 of the female clasp portion 5160. In the illustrated embodiment, the each hook portion provides a u-shaped configuration. Also, the male and female clasp portions provide ladderlock portions 5195 for engaging respective headgear straps. In addition, the female clasp portion 5160 provides an aperture (not visible) for engagement with a c-shaped tube retainer 5187.

Figure 125:
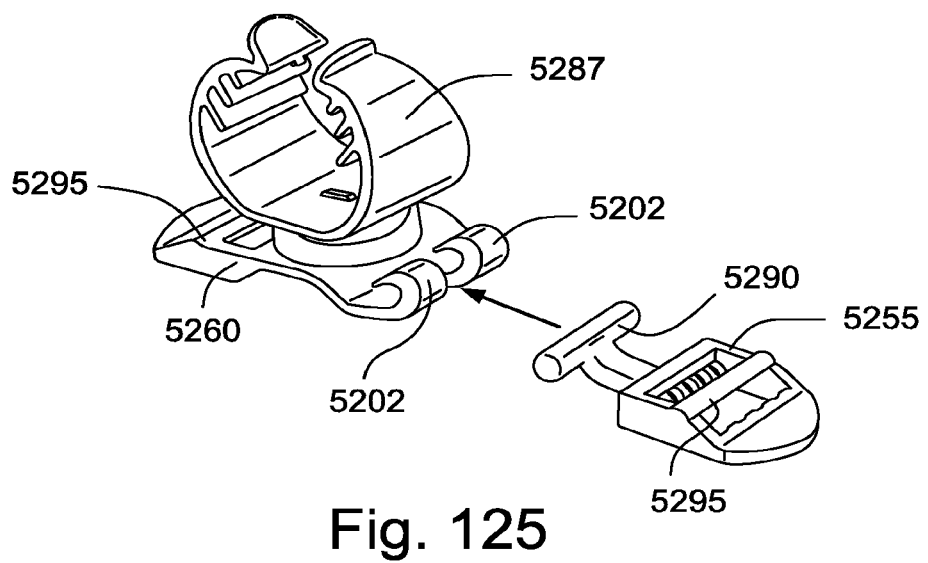

In FIG. 125, the male clasp portion 5255 of the clasp includes a T-bar portion 5290 for engaging spaced apart hook portions 5202 of the female clasp portion 5260. In the illustrated embodiment, the each hook portion provides an arcuate c-shaped configuration. Also, the male and female clasp portions provide ladderlock portions 5295 for engaging respective headgear straps. In addition, the female clasp portion 5260 provides an aperture (not visible) for engagement with a c-shaped tube retainer 5287.

FIG. 126 illustrates a buckle including ladderlock portions 5395 on each end for engaging respective headgear straps and an offset retaining portion 5397 with an aperture 5380 for engagement with a tube retainer (not shown).

In FIG. 127, the male clasp portion 5455 of the clasp includes a T-bar portion 5490 for engaging spaced apart hook portions 5402 of the female clasp portion 5460. Also, the male and female clasp portions provide ladderlock portions 5495 for engaging respective headgear straps. In addition, the female clasp portion 5460 provides an aperture 5480 for engagement with a c-shaped tube retainer 5487.

In FIG. 128, the male clasp portion 5555 of the clasp includes a pair of balls or pins 5590 for engaging hook portions 5502 of the female clasp portion 5560. Also, the male and female clasp portions provide ladderlock portions 5595 for engaging respective headgear straps. In addition, the female clasp portion 5560 provides an aperture 5580 for engagement with a c-shaped tube retainer 5587.

4. Headband and Hair Management

According to an embodiment of the present invention, a headband may be provided to the headgear to manage the patient's hair in use. Also, the headgear nay be donned to the patient's head in a particular manner to manage the patient's hair in use.

4.1 Headband

In one embodiment, the top straps 20 may include or be replaced by a headband or hair band (e.g., see headband 420 in FIGS. 129-133). In one embodiment, the top straps 20 form a substructure for the headband which takes the form of an open-ended sock positioned over at least a portion of the top straps 20. This provides the benefit that when the top strap 20 is resized, the sock headband can be slid over the surface of the top strap 20 to cover it. This provides aesthetic and tactile benefits. The headband is preferably soft, and in the case that it replaces the top straps 20 is also preferably elastic to provide adaptability for fitting a range of different sized heads.

The headband may be made from a fabric, rubberised, elastomer, elastic, woven, knitted or netted material.

In this embodiment, the top strap and front strap are about 14 mm wide which is relatively thin. This serves to minimise visual impact and impact on hair styling.

In another embodiment, loops may be provided on each of the top straps 20 to tie down loose ends of the top straps 20. The loops may be made of fabric, silicone or another soft material.

4.2 Method for Donning Headband Headgear

Referring to FIGS. 129-133, sequential steps of a method for donning headgear 410 of a respiratory mask are shown, the headgear comprising a hair band top strap 420.

Referring to FIG. 129, a first step involves the patient holding the respiratory mask by the back strap(s) 430 in front of them. This may also require the patient to detach an interfacing portion of the mask from the headgear 410.

Referring to FIG. 130, a second step involves the patient inserting their head through the loop created by the hair band 420 and the back strap(s) 430.

Referring to FIG. 131, a third step involves the patient pulling the headgear 410 down over their head.

Referring to FIG. 132, a fourth step involves the patient sliding the hair band 420 across the front of their face and up their forehead to a position between the forehead and the crown of their head.

Referring to FIG. 133, a fifth step involves locating the headgear 410 in an in-use position then reattaching the interfacing portion to the headgear 410 if it has been removed and locating it in an interfacing location for delivery of gas to the patient.

Advantageously, the mask helps keep the patient's hair out of their eyes and off their face and avoids tangling or messing up the patient's hair. It is easy and intuitive to use, particularly because many women are familiar with how to use head bands.

4.3 Method for Donning Non-Headband Headgear

Referring to FIGS. 134 to 141, sequential steps of a method for donning non-headband headgear of a respiratory mask are shown. The method is described using the headgear 10 with clasp 25 described above. That is, the respiratory mask has an interfacing portion 5 and headgear 10 comprising top straps 20 that clip together over the top of the patient's head with clasp 25.

Referring to FIG. 134, a first step of a method of donning headgear 10 of a respiratory mask involves the patient holding the respiratory mask in front of them.

Referring to FIG. 135, a second step involves the patient inserting their head through the loop formed by the back strap 30, front straps 15 and airway interfacing portion 5.

Referring to FIG. 136, a third step involves the patient pulling the respiratory mask over their head.

Referring to FIG. 137, a fourth step involves the patient pulling their hair up, out and over the top of the back strap 30 (i.e. if the patient has long hair).

Referring to FIG. 138, a fifth step involves the patient holding the front straps 15 or back strap 30 (as illustrated) and starting to lift the respiratory mask upwards by the front straps 15.

Referring to FIG. 139, a sixth step involves the respiratory mask being temporarily located over the patient's ears without the patient needing to hold it there. That is, the rear ends of the front headgear straps 15 are moved up and over the patient's ears. Top straps 20 may not be connected.

Referring to FIG. 140, a seventh step involves the patient holding one of the top straps 20 in each hand above their head and moving them towards each other.

Referring to FIG. 141, an eighth step involves the patient moving the top straps 20 to a position adjacent each other near the crown of their head and connecting the male and female clasp portions 55, 60 of the clasp 25 to one another to secure the respiratory mask to the patient's head.

Referring to FIG. 142, a conventional mask is shown where the back strap 530 has slid up the hair on the back of the patient's head and messed it up. Utilisation of the above method has the advantage that the patient's hair styling is not displaced or messed up by the back strap. This makes use of the respiratory mask more comfortable for the patient, thereby improving compliance.

5. Styling of Headgear

The headgear may be adapted to be camouflaged against the patient by being provided in a colour(s) or in a pattern(s) matching the patient's skin colour and/or hair colour. The mask may also be provided in feminine colours.

The headgear may be adapted to be camouflaged against the patient by being provided with an aesthetic surface pattern that matches or suits the facial shape of the patient.

The material pattern may also be selected such that during manufacture a headgear element may be die-cut out of any portion of the patterned fabric and still be aesthetically suitable. Advantageously, this allows left and right hand side headgear element portions of the fabric to be nested before they are cut out. This reduces material wastage and thus cost of goods.

In an embodiment where the top strap takes the form of a headband, the headband and back strap may be coloured similarly to provide a fitting cue. That is, the headband and back strap may provide a coloured loop through which the patient's head is to be inserted.

In an embodiment, the headgear is made from medium to dark coloured materials so the headgear does not show dirt significantly.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. Headgear for supporting a respiratory mask on a patient's face while breathable gas is delivered to the patient for treatment of sleep disordered breathing, the headgear comprising:
   at least one rigidizer, the at least one rigidizer being configured to extend over the patient's cheek and between the patient's eye and ear when the respiratory mask is worn; and
   a cover comprising a fabric material, the at least one rigidizer being disposed within an interior portion of the cover, the rigidizer having increased rigidity as compared to the fabric material,
   wherein the at least one rigidizer is positioned between a face contacting side and a non-face contacting side of the cover,
   wherein, in a transverse cross-sectional view of the headgear, the cover extends laterally beyond the rigidizer to form lateral edge portions of the headgear,
   wherein the face contacting side of the cover has 1) a first outer surface arranged to contact the patient's skin when the respiratory mask is worn during treatment of sleep disordered breathing and 2) a second inner surface opposite the first outer surface,
   wherein the non-face contacting side of the cover has a first inner surface that engages a surface of the rigidizer, and
   wherein, in the lateral edge portions, the second inner surface of the face-contacting side of the cover is directly adhered to the first inner surface of the non-face contacting side of the cover, and
   wherein the cover is secured in place on the rigidizer, and the cover is not configured to be slidably installed or slidably removed from the rigidizer.

2. Headgear as claimed in claim 1, wherein the at least one rigidizer has a curved form arranged to extend over the patient's cheek in an upward direction and towards a rear portion of the patient's head, in use.

3. Headgear as claimed in claim 1, further comprising a pair of top straps configured to extend from a respective side of the patient's head toward a top of the patient's head for length adjustable connection to one another when the respiratory mask is worn.

4. Headgear as claimed in claim 3, wherein each top strap has an upper end configured to be disposed on top of the patient's head when the respiratory mask is worn.

5. Headgear as claimed in claim 1, further comprising a back strap configured to extend around a rear portion of the patient's head and urge against the patient's occiput when the respiratory mask is worn.

6. Headgear as claimed in claim 5, wherein the headgear is configured to, in use, extend along the sides of the patient's face above the patient's ears and includes opposing depending portions configured to extend behind the patient's ears, the opposing depending portions terminating at a junction with the back strap such that the back strap extends rearwardly and downwardly in use.

7. Headgear as claimed in claim 6, wherein the lateral edge portions of the headgear have reduced rigidity as compared to a central portion of the headgear containing the rigidizer.

8. Headgear as claimed in claim 5, wherein the back strap comprises a middle portion having a longitudinal slit along the middle portion and defining an upper back strap portion and a lower back strap portion which splay apart in use such that the back strap grips the head and/or hair better to stabilise the headgear.

9. Headgear as claimed in claim 8, wherein the slit comprises key-hole shaped enlarged radii at its ends.

10. Headgear as claimed in claim 5, where a line of joining between the at least one rigidizer and the back strap is at an angle other than substantially perpendicular to the general axial direction of the back strap at its ends.

11. Headgear as claimed in claim 1, wherein, in the transverse cross-sectional view of the headgear, the face contacting side and the non-face contacting side of the cover are spaced apart in a central portion of the headgear.

12. Headgear as claimed in claim 11, wherein the face contacting side and the non-face contacting side of the cover are adhered to one another at the lateral edge portions of the headgear such that no space is formed between the face contacting side and the non-face contacting side of the cover at the lateral edge portions of the headgear.

13. Headgear as claimed in claim 1, wherein the at least one rigidizer comprises a pair of rigidizers, each rigidizer having a curved form configured to extend over the patient's cheek and between the patient's eye and ear on a respective side of the patient's face when the respiratory mask is worn.

14. The headgear as claimed in claim 13, further comprising a back strap configured to extend around a rear portion of the patient's head in use,
   wherein the back strap has opposing ends, each end of the back strap being configured to at least indirectly connect to a respective one of the rigidizers.

15. The headgear as claimed in claim 14, wherein each rigidizer has a slot to receive a respective end of the back strap.

16. The headgear as claimed in claim 15, wherein the back strap is adjustable to accommodate differently sized and/or differently shaped heads.

17. A respiratory mask for delivering breathable gas to a patient for treatment of sleep disordered breathing, the respiratory mask comprising:
   an airway interfacing portion configured to engage a patient's face to deliver the breathable gas to an airway of the patient; and the headgear of claim 1, the headgear being configured to position and stably hold the airway interfacing portion in an operative position with respect to the patient's face when the respiratory mask is worn.

18. The respiratory mask as claimed in claim 17, wherein the airway interfacing portion is an under-the-nose cushion configured to, in use, seal against the patient's face below the patient's nasal bridge and without sealing around the patient's mouth.

19. The respiratory mask as claimed in claim 17, said respiratory mask further comprising a frame,
   wherein the airway interfacing portion is disposed on the frame.

20. The respiratory mask as claimed in claim 17, wherein the at least one rigidizer of the headgear is at least indirectly connected to the frame.

\* \* \* \* \*

UNITED STATES PATENT AND TRADEMARK OFFICE
CERTIFICATE OF CORRECTION

PATENT NO. : 12,083,281 B2  
APPLICATION NO. : 17/868190  
DATED : September 10, 2024  
INVENTOR(S) : Joel Edward Gibson et al.

Page 1 of 1

It is certified that error appears in the above-identified patent and that said Letters Patent is hereby corrected as shown below:

In the Claims

Claim 1, Column 1, Lines 52-54, "wherein the non-face contacting side of the cover has a first inner surface that engages a surface of the rigidizer, and" --should read-- "wherein the non-face contacting side of the cover has a first inner surface that engages a surface of the rigidizer,"

Signed and Sealed this  
Sixth Day of January, 2026

John A. Squires  
*Director of the United States Patent and Trademark Office*